United States Patent
Heiser

(10) Patent No.: US 12,312,335 B1
(45) Date of Patent: *May 27, 2025

(54) CRYSTALLINE PHARMACEUTICALLY ACCEPTABLE SALT AND POLYMORPHIC FORM OF THE GLUTAMINYL CYCLASE INHIBITOR VAROGLUTAMSTAT

(71) Applicant: VIVORYON THERAPEUTICS N.V., Halle (DE)

(72) Inventor: Ulrich Heiser, Halle (DE)

(73) Assignee: Vivoryon Therapeutics N.V., Halle (DE)

( * ) Notice: Subject to any disclaimer, the term of this patent is extended or adjusted under 35 U.S.C. 154(b) by 0 days.

This patent is subject to a terminal disclaimer.

(21) Appl. No.: 19/020,776

(22) Filed: Jan. 14, 2025

Related U.S. Application Data

(63) Continuation of application No. 18/743,417, filed on Jun. 14, 2024.

(30) Foreign Application Priority Data

Jun. 16, 2023 (WO) ................ PCT/EP2023/066306

(51) Int. Cl.
  *C07D 403/04* (2006.01)
  *A61K 31/4184* (2006.01)
  *A61K 45/06* (2006.01)

(52) U.S. Cl.
  CPC ........ *C07D 403/04* (2013.01); *A61K 31/4184* (2013.01); *A61K 45/06* (2013.01)

(58) Field of Classification Search
  CPC ... C07D 403/04; A61K 31/4184; A61K 45/06
  See application file for complete search history.

(56) References Cited

U.S. PATENT DOCUMENTS 9,173,885 B2 * 11/2015 Heiser ...................... A61P 5/00

FOREIGN PATENT DOCUMENTS

WO 2011/029920 A1 3/2011

OTHER PUBLICATIONS

Hoffmann, Torsten et al: "Glutaminyl Cyclase Inhibitor PQ912 Improves Cognition in Mouse Models of Alzheimer's Disease-Studies in Relation to Effective Target Occupancy", Journal of Pharmacology and Experimental Therapeutics, vol. 362 (1), pp. 119-130 (2017).
NIH: National Library of Medicine, pq912 Hydrochloride, XP093119745, Url: https://pubchem.ncbi.nlm.nih.gov/Compound/146675108, 1-9 (2020).
Scheltens, Philip et al., Safety, Tolerability and Efficacy of the Glutaminyl Cyclase Inhibitor PQ912 in Alzheimer's Disease: Results of A Randomized, Double-Blind, Placebo-Controlled Phase 2a Study; Alzheimers Research and Therapy, vol. 10 (1), 2-14 (2018).

* cited by examiner

*Primary Examiner* — Joseph K McKane
*Assistant Examiner* — Meghan C Heasley
(74) *Attorney, Agent, or Firm* — Olson & Cepuritis, Ltd.

(57) ABSTRACT

The present invention is concerned with a crystalline pharmaceutically acceptable salt of the glutaminyl cyclase inhibitor Varoglutamstat. Varoglutamstat is chemically designated as(S)-1-(1H-benzo[d]imidazol-5-yl)-5-(4-propoxyphenyl) imidazolidin-2-one and is also known under the code PQ912. The invention further relates to a polymorphic form of the hydrochloride salt of(S)-1-(1H-benzo[d]imidazol-5-yl)-5-(4-propoxyphenyl) imidazolidin-2-one, to processes for preparing said hydrochloride salt and its polymorphic form, pharmaceutical compositions containing the same, therapeutic uses thereof and methods of treatment employing them.

30 Claims, 26 Drawing Sheets
Specification includes a Sequence Listing.

| (ppm) | Value |
|---|---|
| [0.85..99] | 2.982 |
| [1.00..1.07] | 0.111 |
| [2.06..2.10] | 0.020 |
| [3.07..3.17] | 0.999 |
| [3.48..3.53] | 0.114 |
| [3.64..3.74] | 12.508 |
| [3.77..3.95] | 3.256 |
| [5.47..5.63] | 0.900 |
| [6.82..6.87] | 9.053 |
| [6.87..6.90] | 1.271 |
| [7.22...7.30] | 2.066 |
| [7.58..7.63] | 0.987 |
| [7.54 .. 7.70] | 0.997 |
| [7.59.. 7.98] | 1.000 |
| [9.41.. 9.50] | 0.993 |

Date: 20 Oct 2010 11:53:04
Frequency (MHz): 400.13
Nucleus: 1H
Solvent: DMSO-d6
Temperature (degree C): 20.160
Pulse Sequence: zg30
Number of Transients: 16
Receiver Gain: 128.00
Spectrum Offset (Hz): 2002.0245
Sweep Width (Hz): 4789.24
Points Count: 131072

Fig. 16 (Continued)

| Magnification | Ex. 4.2 | Ex. 4.3 |
|---|---|---|
| x 325 | | |
| *Light intensity* | 12 | 5 |
| x 651 | | |
| *Light intensity* | 12 | 7 |

Fig. 32

CRYSTALLINE PHARMACEUTICALLY ACCEPTABLE SALT AND POLYMORPHIC FORM OF THE GLUTAMINYL CYCLASE INHIBITOR VAROGLUTAMSTAT

CROSS-REFERENCE TO RELATED APPLICATIONS

This application is a continuation of U.S. application Ser. No. 18/743,417, filed on Jun. 14, 2024, which is incorporated herein by reference in its entirety.

INCORPORATION OF SEQUENCE LISTING

Biological sequence information for this application is included in a XML file having the file name "MAI-244-Sequence Listing.xml", created on Jun. 12, 2024, and having a file size of 22,973 bytes, which is incorporated herein by reference.

FIELD OF THE INVENTION

The present invention is concerned with a crystalline pharmaceutically acceptable salt of the glutaminyl cyclase inhibitor Varoglutamstat. Varoglutamstat is chemically designated as(S)-1-(1H-benzo[d]imidazol-5-yl)-5-(4-propoxyphenyl) imidazolidin-2-one and is also known under the code PQ912. The invention further relates to a polymorphic form of the hydrochloride salt of(S)-1-(1H-benzo[d]imidazol-5-yl)-5-(4-propoxyphenyl) imidazolidin-2-one, to processes for preparing said hydrochloride salt and its polymorphic form, pharmaceutical compositions containing the same, therapeutic uses thereof and methods of treatment employing them.

BACKGROUND OF THE INVENTION

Glutaminyl cyclase (QC, EC 2.3.2.5) catalyzes the intramolecular cyclization of N-terminal glutamine, and, at a lower rate, also glutamate residues into pyroglutamic acid (pGlu*), liberating ammonia or water. A QC was first isolated by Messer from the latex of the tropical plant Carica papaya in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer, W. H. and Spiess, J. 1987 Proc Natl Acad Sci USA 84, 3628-3632). For the mammalian QC, the conversion of Gln into pGlu by QC could be shown for the precursors of TRH and GnRH (Busby, W. H. J. et al. 1987 J Biol Chem 262, 8532-8536; Fischer, W. H. and Spiess, J. 1987 Proc Natl Acad Sci USA 84, 3628-3632). In addition, initial localization experiments of QC revealed a co-localization with its putative products of catalysis in bovine pituitary, supporting the suggested function in peptide hormone synthesis (Bockers, T. M. et al. 1995 J Neuroendocrinol 7, 445-453). In contrast, the physiological function of the plant QC is less clear. In the case of the enzyme from C. papaya, a role in the plant defense against pathogenic microorganisms was suggested (El Moussaoui, A. et al. 2001 Cell Mol Life Sci 58, 556-570). Putative QCs from other plants were identified by sequence comparisons recently (Dahl, S. W. et al. 2000 Protein Expr Purif 20, 27-36). The physiological function of these enzymes, however, is still ambiguous.

The QCs known from plants and animals show a strict specificity for L-Glutamine (and L-Glutamate) in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from C. papaya and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

In 2010, a bacterial glutaminyl cyclase was characterized, followed by identification of insect QCs, and QC from oral pathogens Porphyromonas gingivalis, Tannerella forsythia, and Prevotella intermedia. Although QCs of all kingdoms catalyze the same reaction, they differ concerning their structure and catalytic sites: bacterial and plant QCs have been classified as type I QC enzymes, mammals and insects possess type II QCs. The physiological role and targets of type I QCs are not fully known. Such QCs from oral pathogens represent attractive target enzymes for small-molecule inhibitor development, as their action is likely to stabilize essential periplasmic and outer membrane proteins by N-terminal pyroglutamination. In contrast to other microbial type I QCs, these oral pathogens' QCs possess sequences corresponding to type II QCs (summarized in Taudte, N. et al. 2021 J Biol Chem 296. Article 100263).

Periodontitis is a widespread bacterially driven chronic inflammatory disease and has been characterized as a microbial shift-disease, where pathogenic bacteria of the oral microbiome become predominant. In particular, the keystone pathogen Porphyromonas gingivalis together with other anaerobic bacteria such as Tannerella forsythia initiates dysbiosis, resulting in disruption of tissue homeostasis and normal immune response. This inadequate inflammatory host response leads finally to degradation of periodontal tissue. Periodontitis affects not only the oral cavity; a number of studies have demonstrated links between periodontitis and systemic diseases, including cancer, cardiovascular disease, rheumatoid arthritis, and Alzheimer's disease. Following the first detection of P. gingivalis in the brain tissue of AD patients, subsequent studies have revealed a correlation between P. gingivalis infection and the etiopathogenesis of Alzheimer's disease, presumably by activation of inflammatory mechanisms, neuroinflammation and neurodegeneration (summarized in Taudte, N. et al. 2021 J Biol Chem 296. Article 100263).

It was shown that recombinant human QC as well as QC-activity from brain extracts catalyze both, the N-terminal glutaminyl as well as glutamate cyclization. Most striking is the finding, that cyclase-catalyzed $Glu_1$-conversion is favored around pH 6.0 while $Gln_1$-conversion to pGlu-derivatives occurs with a pH-optimum of around 8.0. Since the formation of pGlu-AB-related peptides can be suppressed by inhibition of recombinant human QC as well as QC-activity from pig pituitary extracts, the enzyme QC is a target in drug development for treatment of Alzheimer's disease.

The glutaminyl cyclase inhibitor, (S)-1-(1H-benzo[d]imidazol-5-yl)-5-(4-propoxyphenyl) imidazolidin-2-one can be represented by the following structural formula:

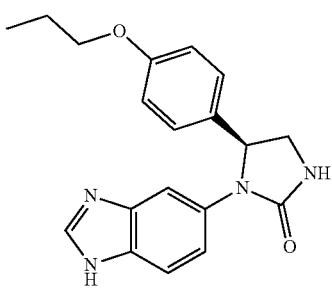 [SMILES: CCCOc1ccc([C@H]2CNC(=O)N2c2ccc3[nH]cnc3c2)cc1]

Varoglutamstat is an inhibitor of glutaminyl cyclase (QC), also named glutaminyl-peptide cyclotransferase (QPCT), and its iso-form isoQC (QPCTL). The QC metalloenzyme is upregulated in the brains of Alzheimer's disease patients. QC generates pyroglutamate Aβ (pGlu-Aβ), a modified, pathogenic form of the peptide, by catalyzing the cyclization of an exposed glutamate at the N-terminus of Aβ. The enzyme has been reported to be highly expressed in affected cortical regions in AD; the resulting pGlu-Aβ has been found to be toxic, highly aggregation-prone, and a major component of amyloid plaques in humans (Morawski M, et al., Glutaminyl cyclase in human cortex: correlation with (pGlu)-amyloid-β load and cognitive decline in Alzheimer's disease. J Alzheimers Dis. 2014; 39 (2): 385-400; Frost J L et al., Pyroglutamate-3 Amyloid-β Deposition in the Brains of Humans, Non-Human Primates, Canines, and Alzheimer Disease-Like Transgenic Mouse Models. Am J Pathol. 2013 August; 183 (2): 369-81).

Varoglutamstat represents a small-molecule approach to reducing pGlu-Aβ generation. Donanemab, an antibody targeting this pathogenic species directly, is under development as well (Demattos R B, Lu J, Tang Y, Racke M M, DeLong C A, Tzaferis J A, Hole J T, Forster B M, McDonnell P C, Liu F, Kinley R D, Jordan W H, Hutton M L. A plaque-specific antibody clears existing β-amyloid plaques in Alzheimer's disease mice. Neuron. 2012 Dec. 6; 76 (5): 908-20). Aducanumab, or BIIB037, is a monoclonal IgG1 antibody that targets extracellular amyloid-β plaques in the brain; similar to gantenerumab, bapineuzumab and solanezumab. In 2021, aducanumab, has been authorized in the US through the accelerated approval pathway. In clinical studies in early AD patients, it produced persistent reductions of Aβ deposits in a time- and dose-dependent manner and showed also improvements in other pharmacodynamic (PD) and clinical AD markers [Aduhelm USPI (United States Prescribing Information), Version of June 2021]. In January 2023, the U.S. Food and Drug Administration approved Leqembi (lecanemab-irmb) via the Accelerated Approval pathway for the treatment of Alzheimer's disease (Reardon, S. Nature 2023, 613, 227-228). Lecanemab is a humanized IgG1 monoclonal antibody which binds to Aβ soluble protofibrils with high affinity. Leqembi has been shown to reduce brain amyloid and modestly slow cognitive decline in adult patients with early Alzheimer disease. (van Dyck, C. H. et al., N. Engl. J. Med. 2023, 388, 9-21)

In preclinical work, QC inhibitors have been reported to reduce amyloid pathology and improve performance in learning and memory tests in various mouse models (Schilling S et al., Glutaminyl cyclase inhibition attenuates pyroglutamate Abeta and Alzheimer's disease-like pathology. Nat Med. 2008 October; 14 (10): 1106-11). In mice doubly transgenic for human APP and human glutaminyl cyclase, chronic oral dosing with PQ912 was reported to reduce brain pyroglutamate AB and improve recall in the Morris water maze test of spatial memory (Hoffmann T et al., Glutaminyl Cyclase Inhibitor PQ912 Improves Cognition in Mouse Models of Alzheimer's Disease-Studies on Relation to Effective Target Occupancy. J. Pharmacol. Exp. Ther. 2017, 362, 119-130.). Moreover, combination of the glutaminyl cyclase inhibitor PQ912 (Varoglutamstat) and the murine monoclonal antibody PBD-C06 (m6) targeting pGlu-Aβ species shows additive effects on brain Aβ pathology in transgenic mice (Hoffmann, T. et al., Int. J. Mol. Sci. 2021, 22, 11791).

WO2011029920A1 describes a broad range of QC inhibitors. Varoglutamstat ((S)-1-(1H-benzo[d]imidazol-5-yl)-5-(4-propoxyphenyl) imidazolidin-2-one) is disclosed therein as one of 235 example compounds. WO2011029920A1 also discloses a general synthesis description of Varoglutamstat. WO2011029920A1 mentions several pharmaceutically acceptable salts derived from addition of respective acids. These include hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4 methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable salts derived from addition of basic reagents include ammonium salts, alkali metal salts such as those of sodium and potassium, alkaline earth metal salts such as those of calcium and magnesium and salts formed with organic bases such as dicyclohexylamine and N-methyl-D-glucamine.

Synthesis of Varoglutamstat ((S)-1-(1H-benzo[d]imidazol-5-yl)-5-(4-ropoxyphenyl) imidazolidin-2-one) as free base has been generally described in WO2011029920A1. No specific salt form of Varoglutamstat is disclosed in WO2011029920A1. In preclinical and clinical studies, which are currently ongoing, the use of Varoglutamstat ((S)-1-(1H-benzo[d]imidazol-5-yl)-5-(4-propoxyphenyl) imidazolidin-2-one) freebase is not desirable, starting with its very poor solubility in water.

The choice of a particular salt form of a drug often is driven by numerous factors such as API chemistry, intended dosage form and pharmacokinetics. Choice of the appropriate salt can improve the overall therapeutic and pharmaceutical effects of an API- and choosing the incorrect salt form can have the opposite effect and can be quite detrimental for overall drug development.

SUMMARY OF THE INVENTION

In a first aspect, the invention provides a polymorph of Varoglutamstat Hydrochloride.

In a second aspect, the invention provides a hydrochloride salt of Varoglutamstat, which comprises or consist of the polymorph with the characteristics as described herein. The invention further relates to pharmaceutical compositions comprising said hydrochloride salt of Varoglutamstat.

In a third aspect, the invention relates to a process for preparing a hydrochloride salt of Varoglutamstat, said process comprising dissolving Varoglutamstat free base in a suitable organic solvent, supplementing with a certain minor quantity of water, adding a solution comprising aqueous HCl mixed into said organic solvent, and harvesting Varoglutamstat Hydrochloride crystals.

In a fourth aspect, the present invention provides the use of Varoglutamstat Hydrochloride, as described herein, for use in methods of preventing, alleviating or treating of diseases.

General Introduction

The present invention deals with the problem to provide a crystalline salt of Varoglutamstat which is suitable for drug development. A crystalline solid state is considered advantageous for the development of a solid oral dosage form and was therefore aspired to be identified for Varoglutamstat. An acceptable solid form of a Varoglutamstat salt should fulfill the following requirements:

Good aqueous solubility,
One energetically favored polymorph,
Good crystallinity (low or no amorphous content),
Good crystal habit (shape and size of crystals),
Acceptable handling (filtration behavior, low hygroscopicity etc.).

This problem is solved in this invention by the provision of the hydrochloride salt of Varoglutamstat ((S)-1-(1H-benzo[d]imidazol-5-yl)-5-(4-propoxyphenyl) imidazolidin-2-one) which comprises or consists of a polymorph as describe hereinbelow, and a process for obtaining said hydrochloride salt of Varoglutamstat comprising or consisting of said polymorph. The invention is further detailed hereinbelow.

In order to achieve a solid hydrochloride which satisfies the above-mentioned requirements, the inventors had to overcome several drawbacks. It turned out that a desired salt form could not simply be formed using conventional measures.

In a solubility screen (see Example 2), it was found that the Varoglutamstat free base is highly soluble in certain organic solvents, but is almost insoluble in water, forming a sticky/oily suspension. Moreover, despite various attempts to crystallize the free base, no crystalline sample could be obtained. Because of the latter finding and the low water solubility, the free base of Varoglutamstat was not considered appropriate for drug development. Therefore, pharmaceutically acceptable salt forms with improved features had to be developed. Finding a suitable salt form of a drug can be a difficult and unpredictable process. In many cases, the physical properties of a given salt can be quite strikingly different depending on how the salt is made, due to differences in crystal form, possible inclusion of solvents, or the presence of amorphous forms or multiple crystal forms in the obtained salt. Finding the right conditions for forming a desired salt often requires more than just routine screening, the salt formed in a simple crystallization screening protocol could exhibit undesirable properties that discourage further evaluation, even though a suitable form of the salt might be obtainable. As Varoglutamstat represents a weak base (pKa 4.55), it was expected that only a limited selection of respective pharmaceutically acceptable acids would form a salt with the free base at all.

The inventors therefore performed an initial screen for suitable counter ions in order to identify possible salt forms of Varoglutamstat (see Example 3.1). Altogether 10 pharmaceutically acceptable acids were tested for salt formation, and microcrystallization experiments were performed in 12 crystallization media. The list of the crystallization media comprised solvents such as acetonitrile, isopropyl alcohol, ethanol, acetone, tetrahydrofuran, 1-propanol, and water, which were tested as single solvents or as mixtures with water (50/50, v/v). All crystallization media were tested with each of the selected acids.

Out of the 10 acids studied within the Varoglutamstat salt screening on microplates, only 4 formed a crystalline salt. From these 4 acids, benzenesulfonic acid and camphorsulfonic acid were found to lead to well crystallized materials in these initial studied experimental conditions. Toluene sulfonic and maleic acid have only led to partially crystalline materials. The 6 other tested acids (oxalic, hydrochloric, sulfuric, aspartic, phosphoric and methanesulfonic acids) were found not to be able to form a crystalline salt with the free base of Varoglutamstat under the tested experimental conditions. As a result of this experiment, benzenesulfonic and camphorsulfonic acid were initially deemed to be promising candidates to form a salt with the free base of Varoglutamstat; however, the invention as described herein showed it was possible despite these results to crystallize and develop a HCl in form of a stable polymorph.

Based on the good solubility of the free base of Varoglutamstat in isopropanol, the inventors performed another salt screening experiment in this solvent (see Example 3.2). Again, 10 pharmaceutically acceptable acids were tested, out of which 7 were identical to those utilized in Example 3.1 as to get confirmation of the results obtained there. Out of these 10 tested potential salt compositions, the chloride, tosylate, oxalate, maleate and fumarate showed a formation of a crystalline salt with Varoglutamstat upon protonation in a clear stoichiometry.

As per definition, Varoglutamstat Hydrochloride as discussed herein has the chemical formula:

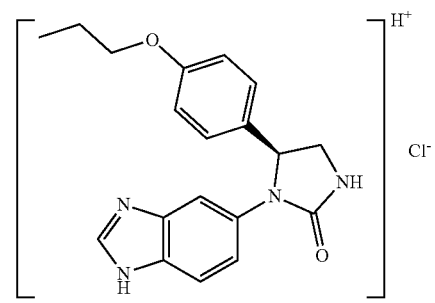

As far as Varoglutamstat Tosylate is discussed herein (as a representative of a salt formed between Varoglutamstat free base and an organic acid), Varoglutamstat Tosylate has the chemical formula:

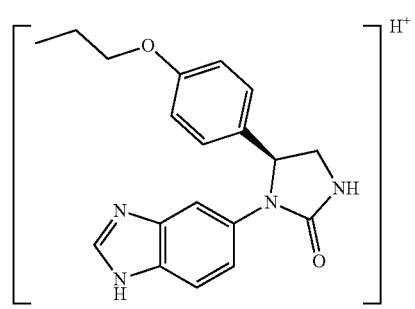

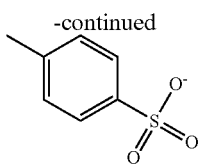

Unexpectedly, in these studies, the tosylate and the hydrochloride showed the best crystallinity and a clear melting behavior with melting points in acceptable high range in comparison to the free base. In contrast to the tosylate, the hydrochloride exhibited a substantial hygroscopicity. As a further drawback, it was found that the suspensions had to be diluted after crystallization with solvent in order to allow a filtration, which pointed towards a non-favorable proceeding with regard to crystallinity and handling of the manufacturing process of the respective salt form. In particular, crystallization experiments with aqueous HCl in isopropanol showed that addition of the HCl suddenly led to thick suspensions with slow filtration speed. The obtained suspensions either looked amorphous under the microscope or were of hair-like nature.

For both, the tosylate and the hydrochloride salts, further characterization of their respective aqueous solubilities was performed. The hydrochloride salt showed advantageous aqueous solubility as compared to the tosylate salt, as the aq. solubility of the former was two orders of magnitude higher than that of the latter.

Taken together, the hydrochloride salt of Varoglutamstat obtained in Example 3.2 showed a higher solubility in water compared to the free base and other salt forms tested. However, the salt formation in isopropanol with aqueous HCl tended to occur spontaneously, resulting in a very thick suspension and material comprising amorphous halos, and the material was deemed to be hygroscopic, which is disadvantageous for drug development.

Despite the drawbacks of the hydrochloride salt of Varoglutamstat with regard to crystal habit, crystallization behavior and hygroscopicity, its much higher solubility in water compared to the tosylate salt made it more desirable for further development as an active pharmaceutical ingredient of a drug. Furthermore, sulfonates have the potential to form esters in the presence of alcohols which may be present during manufacturing processes. Such esters represent impurities of genotoxic potential if present in the final product. In conclusion, sulfonates were considered to bear potential drawbacks for further development, and the inventors went on to further optimize the crystallization conditions of the hydrochloride salt of Varoglutamstat.

Accordingly, further attempts (described in example 4.1) were undertaken to produce crystals of a hydrochloride salt of Varoglutamstat with improved properties by eliminating the aqueous component during salt formation. The solubility of the hydrochloride salt of Varoglutamstat obtained in example 3.2 was determined in 18 solvents. A very high solubility was found in water and alcohols, which made those obsolete for salt formation processes in a single solvent. In contrast, the solubility of Varoglutamstat Hydrochloride in almost all other solvents was very low and led to spontaneous nucleation of crystals. This resulted in unstirrable and poorly filterable suspensions with the need for high dilution to get the suspensions stirrable again.

However, intensive stirring of such suspensions resulted in a sort of wet milling, leading to a deterioration of crystals by generating round edges by attrition. FIG. 8 shows microscopy pictures of such a thick suspension after stirring for more than one week in comparison to the original crystals (as seen in FIG. 7).

A first change of solvents was not successful either. In DMSO/acetone, the suspension turned almost to a block even though it was seeded. The addition of the first few drops of HCl in dioxane resulted in formation of amorphous flakes rather than needles.

The salt formation in pure isopropanol with HCl in isopropanol was found to be hardly stirrable, even upon initial seeding to trigger a controlled crystallization. The addition of HCl in isopropanol was slowed down to almost 12 hours, but still a spontaneous nucleation occurred towards the end of the addition.

In one of the follow-up experiments with extended HCl addition period, initial suspensions forming already during HCl addition were directly diluted with acetone. Unexpectedly and surprising for the inventors, a further spontaneous nucleation within the suspension as seen with pure isopropanol as solvent was clearly slowed down if not avoided. The resulting suspension from this dilution approach showed a promising crystallization behavior. This observation was used to add acetone from the beginning to the salt formation mixture, and now seeding resulted in a successful crystallization. Taken together, the addition of HCl to the seeded mixture in isopropanol did not show a clean crystallization but the addition of acetone seemed to improve it.

The yield of crystalline Varoglutamstat Hydrochloride in the experiments with acetone addition was still low. Therefore, further additional experimentation was undertaken to increase the yield. In particular, the composition of the salt formation mixture was varied. Starting with a higher amount of acetone in isopropanol (60% v/v acetone) led, however, to an almost solidification of the mixture. The use of a 1/1 (v/v) starting mixture of acetone and isopropanol followed by further addition of acetone after the salt formation occurred resulted in a much better crystallization behavior.

With the process as described in Example 4.1, and in even more detail in Example 4.2, the product Varoglutamstat Hydrochloride was obtained with 89% yield and an overall purity of 99.82% (HPLC). Disadvantageously, DVS, DSC and TGA analyses showed that the obtained material was still too hygroscopic and possibly shows the formation of a solvate or hydrate. This was demonstrated by the experiments performed according to the experimental section. The TGA experiment of Example 4.2 revealed a 4.3% mass loss at 194° C. that could correspond to loss of one water molecule/mol (4.6%) and therefore a monohydrate structure. In the DVS experiment, Varoglutamstat Hydrochloride does not show hygroscopicity up to a humidity of 55% RH. After that, between 55 and 80-85% RH, a mass gain is detected, that finally reaches 5-6% at 95% RH. This water incorporation, caused by the submission to high relative humidity (both by DVS or upon storage at 95% RH after 3 days or 1 week, respectively), then led to a change in the DSC (FIG. 13) and also the TGA (FIG. 14) profiles. The DSC of the humidity exposed form, melts at 150° C. and then changes into a form, melting at higher temperature. The melting point at the high temperature is then similar to the melting of Varoglutamstat Hydrochloride, prepared according to Example 4.1 and not exposed to elevated humidity. The TGA profile of the humidity exposed form shows an additional mass loss of 4.6%, (corresponding to one water molecule per mol) at 185° C. before the melting of the high temperature form. Surprisingly, the XRPD (FIG. 15) of the humidity exposed form shows no difference as compared to the form not exposed to elevated hygroscopicity (FIG. 10).

Crystallization in solvent mixtures comprising isopropanol led further to the disadvantage that isopropylchloride (2-chloropropane) is formed as an impurity in trace amounts. Isopropylchloride is known to be genotoxic.

Therefore, the Varoglutamstat Hydrochloride formation process was further investigated, as described in Example 4.3. In an initial experiment, it was found that an acetone/water system with a low water content led to the formation of crystalline material. A yield of 92% was obtained as an off-white solid that showed crystalline habitus (microscope, agglutinated needles). Even though the product was obtained in good yield, this protocol was still unsuitable for further investigations due to solidification of the suspension after completed HCl addition, confirming the outcome of former crystallization experiments with aqueous HCl in isopropanol, which showed that addition of HCl suddenly led to the formation of thick suspensions and thus slow filtration speed.

Eventually, an acetone/water system was used implementing additional water under changed conditions. The final experiment is described in Example 4.3. The obtained Varoglutamstat Hydrochloride crystals showed a needle-like structure (FIG. 18). The chemical structure was confirmed by NMR assay (FIG. 23). DVS and DSC analyses showed that the obtained material was no longer hygroscopic. As shown in FIG. 22, the DVS shows no mass gain over the complete range of RH. Moreover, the DSC (FIG. 20) shows only the melting of the higher melting form. The TGA (FIG. 21) does not show any meaningful mass-loss pointing towards a solvate or hydrate.

Furthermore, the crystallization process used in Example 4.3 does not make use of isopropanol. Therefore, the obtained Varoglutamstat Hydrochloride crystals were free of isopropylchloride.

Therefore, the invention provides a process for preparing a Hydrochloride salt of Varoglutamstat, said process comprising dissolving Varoglutamstat free base in a solvent mixture comprising a polar aprotic organic solvent and water, adding a solution comprising HCl, and harvesting Varoglutamstat Hydrochloride crystals.

A polar aprotic solvent is a solvent that lacks an acidic proton and is polar. Such solvents lack hydroxyl and amine groups. In contrast to protic solvents, these solvents do not serve as proton donors in hydrogen bonding, although they can be proton acceptors.

Preferably, the polar aprotic solvent used in the process of the invention is water-mixable.

Suitable examples of water-mixable polar aprotic solvents for use in the process of the present invention are acetone, acetonitrile (Me-CN), dimethyl formamide (DMF), dimethylacetamide (DMAc), dimethyl-sulfoxide (DMSO), 1,4 dioxane, tetrahydrofuran (THF), methyl-tetrahydrofuran (Me-THF), and methyl-ethyl-ketone (MEK).

In a further preferred embodiment, the HCl added to the dissolved Varoglutamstat free base is dissolved in the same water-mixable polar aprotic solvent.

A promising crystallization process was developed using an acetone/water mixture.

The ratio of acetone/water in said mixture is preferably in the range of 48/0.0 to 48/15.0 v/v, more preferably 48/1.0 to 48/5.0 v/v. Most preferably the ratio of the acetone/water in said mixture is 48/1.4 or 48/1.315 v/v, wherein an acetone/water ratio of 48/1.315 v/v is corresponding to a total water content of 221 mg/mmol Varoglutamstat free base.

The use of such an acetone/water mixture in the process of the invention provides several advantages:

Homogenous reaction mixture during the salt formation.

No potential for genotoxic byproduct formation from the used acetone/HCl mixture (in contrast to the use of sulfonates and isopropanol).

Controlled crystallization without solidification of the reaction mixture. Thereby the water amount added facilitates the crystallization process by balancing the crystallization velocity and homogenous crystal formation with the aspired maximal amount of yielded Varoglutamstat Hydrochloride salt.

Short cycle time without long stirring times.

Straightforward reaction and work-up protocol.

No issues anticipated regarding further scale up.

Reproducibility.

The resulting Varoglutamstat Hydrochloride was in an acceptable solid form which fulfilled the following desirable characteristics (as discussed herein before):

Good aqueous solubility,

Good crystallinity (low or no amorphous content),

Good crystal habit (shape and size of crystals),

Acceptable handling (filtration behavior, low hygroscopicity etc.),

Low or no hygroscopicity, and

Absence of genotoxic byproducts, such as isopropylchloride.

Polymorphism screens, as described in Example 5, the anhydrous Varoglutamstat Hydrochloride of Example 4.3 revealed the presence of just one polymorphic form of Varoglutamstat Hydrochloride (especially confirmed in Example 5.5) which did not change under the screening conditions. The XRPD pattern of the Varoglutamstat Hydrochloride obtained in Example 4.3 is shown in FIG. 19. FIGS. 28 and 29, which show an y-normalized overlay of the XRPD profiles of the material obtained in examples 4.2 and 4.3 and confirms the absence of the amorphous halo in the material from example 4.3, which was present in the material obtained in all previous experiments (see e.g. FIG. 4 and FIG. 10). As slurry experiments (Example 5.4, stirring for 5 d in several solvents) did not reveal formation of any new polymorphic form as well, the Varoglutamstat Hydrochloride seems to also fulfill the requirement of existing as just one energetically favored polymorph.

Description of the Aspects and the Embodiments of the Invention

In a first aspect, the invention provides a polymorph of Varoglutamstat Hydrochloride.

Varoglutamstat is designated as(S)-1-(1H-benzo[d]imidazol-5-yl)-5-(4-propoxyphenyl) imidazolidin-2-one. Accordingly, the invention provides(S)-1-(1H-benzo[d]imidazol-5-yl)-5-(4-propoxyphenyl) imidazolidin-2-one hydrochloride, herein also named Varoglutamstat Hydrochloride.

In some embodiments, said polymorph of Varoglutamstat Hydrochloride is characterized by X-ray powder diffraction peaks (2 [Theta]) selected from one or more of the following: 9.5±0.2°, and 24.8±0.2°.

In further embodiments, said polymorph of Varoglutamstat Hydrochloride is characterized by X-ray powder diffraction peaks (2 [Theta]) selected from one or more of the following: 9.5±0.2°, 21.3±0.2°, 22.6±0.2°, and 24.8±0.2°.

In further embodiments, said polymorph of Varoglutamstat Hydrochloride is characterized by X-ray powder diffraction peaks (2 [Theta]) selected from one or more of the following: 5.8±0.2°, 9.5±0.2°, 16.9±0.2°, 17.2±0.2°, 18.9±0.2°, 20.7±0.2°, 21.3±0.2°, 21.7±0.2°, 22.6±0.2°, and 24.8-0.2°.

In further embodiments, said polymorph of Varoglutamstat Hydrochloride is characterized by X-ray powder diffraction peaks (2 [Theta]) selected from one or more of the following: 5.8±0.2°, 9.5±0.2°, 11.3±0.2°, 12.4±0.2°, 15.8±0.2°, 16.9±0.2°, 17.2±0.2°, 18.9±0.2°, 20.2±0.2°, 20.7±0.2°, 21.3±0.2°, 21.7±0.2°, 22.6±0.2°, 23.8±0.2°, 24.8±0.2°, 26.3±0.2°, 27.2±0.2°, 28.3±0.2°, 28.8±0.2°, 29.4±0.2°, 30.1±0.2°, 31.2±0.2° and 33.8±0.2°.

In further embodiments, said polymorph of Varoglutamstat Hydrochloride is characterized by additional X-ray powder diffraction peaks (2 [Theta]) selected from one or more of the following: 17.9±0.2°, 18.4±0.2°, 22.0±0.2°, 24.1±0.2°, 31.1±0.2°, 31.3±0.2°, 34.6±0.2°, 35.4±0.2°, 36.2±0.2°, 37.0±0.2°, 38.6±0.2°, and 39.3±0.2°. Said polymorph of Varoglutamstat Hydrochloride is preferably further characterized by an X-ray diffraction spectrum as shown in FIG. 19.

Said polymorph of Varoglutamstat Hydrochloride is further characterized by a differential scanning calorimetry (DSC) thermogram as shown in FIG. 20.

Said polymorph of Varoglutamstat Hydrochloride is further characterized by a DSC endotherm with an onset temperature of 243° C. and with a peak at 251° C.

In a further embodiment, said polymorph of Varoglutamstat Hydrochloride is characterized by a dynamic vapor sorption (DVS) curve as shown in FIG. 22.

In a further embodiment, said polymorph of Varoglutamstat Hydrochloride is characterized by a thermogravimetric analysis (TGA) thermogram as shown in FIG. 21. Said polymorph of Varoglutamstat Hydrochloride is characterized by one mass loss of 3.0% with onset/endset temperatures of 190/215° C. before the main thermal decomposition of the compound (with an onset temperature of 326° C.).

In a further embodiment, said polymorph of Varoglutamstat Hydrochloride is characterized by a 1H-NMR spectrum as shown in FIG. 23.

In a further embodiment, said polymorph of Varoglutamstat Hydrochloride has an achiral purity of >95%, preferably >96% or >97%, more preferably >98% or >99%, most preferably >99.5% or >99.8%.

In a further embodiment, said polymorph of Varoglutamstat Hydrochloride is substantially free, preferably free of isopropylchloride (2-chloropropanole). More preferably, the content of isopropylchloride is in the range between 0 ppm and 20 ppm, more preferably <20 ppm, <10 ppm, or <5 ppm. Most preferably, the content of isopropylchloride is 0 ppm.

For an API consisting of one amorphous fraction and one crystalline fraction, as it is the case for Varoglutamstat Hydrochloride of the present invention, the relative degree of crystallinity can be comparatively estimated between two batches by comparing the following "crystallinity factor" according to Formula I (USP harmonized method (941), Characterization of crystalline and partially crystalline solids by X-ray powder diffraction (XRPD), Stage 4, Harmonization, May 2022):

% Crystallinity=100×A/(A+B−C)  (Formula I)

wherein
- A is the sum of the net areas of all the peaks arising from the diffraction of the crystalline fraction of the sample;
- B is the area under the diffractogram generated by the sample itself (excluding area A); and
- C is the area of the background noise (due to air scattering, fluorescence, equipment, etc.) which is measured by recording the diffractograms of the (empty) sample holder that was used for recording the diffractograms of the tested samples.

In a further embodiment, the degree of crystallinity of the polymorph of Varoglutamstat Hydrochloride of the present invention is >50%, when calculated according to formula I. Preferably, the degree of crystallinity of the polymorph of Varoglutamstat Hydrochloride of the present invention is >50%, >55, or >60%. More preferably, the degree of crystallinity of said polymorph of Varoglutamstat Hydrochloride is >65%. Most preferably, the degree of crystallinity of said polymorph of Varoglutamstat Hydrochloride is >70%, or even higher. Preferably, the polymorph of the Hydrochloride salt of Varoglutamstat of the invention is substantially free of amorphous material. Amorphous material in the sense of the invention means material that shows no crystals structured regularly.

In a second aspect, the invention provides a Hydrochloride salt of Varoglutamstat, which comprises or consist of the polymorph with the characteristics as described herein before. Per definition, "Hydrochloride salt of Varoglutamstat" as used herein means the Hydrochloride salt of Varoglutamstat which comprises or consist of the polymorph with the characteristics as described herein before and with the characteristics further described herein below.

In one embodiment, the Hydrochloride salt of Varoglutamstat of the invention is non-hygroscopic.

In a further embodiment the Hydrochloride salt of Varoglutamstat of the invention shows a water uptake <6.0% at 95% RH, Preferably the water uptake is <5.0, <2.5, <1.3 or <0.6 at 95% RH. Most preferably the water uptake at 95% RH is 0.0%.

In a further embodiment, the Hydrochloride salt of Varoglutamstat of the invention is not a solvate.

In a further embodiment, the Hydrochloride salt of Varoglutamstat of the invention is not a hydrate.

In a further embodiment, the TGA shows a mass loss <9.20% corresponding to <2 water molecules per mol or any other solvate related substance. Preferably, the TGA profile corresponds to the loss of <4.60% (<1 water molecule or any other solvate related substance), <2.30% (<0.5 water molecule per mol or any other solvate related substance). Most preferably the TGA does not show any loss of water or any other solvate related substance. The Hydrochloride salt of Varoglutamstat of the invention forms crystals. Said crystals preferably comprise or consist of needles, more preferably of needles as shown in FIG. 18.

The Hydrochloride salt of Varoglutamstat of the invention has a very good solubility in water, which means that said Hydrochloride salt of Varoglutamstat has a solubility in water at 20° C. of ≥0.10 M, preferably ≥0.11 M, more preferably >0.12 M, most preferably ≥0.13 M or ≥0.14 M.

In a third aspect, the invention relates to a process for preparing a Hydrochloride salt of Varoglutamstat, said process comprising dissolving Varoglutamstat free base in a polar aprotic water-mixable organic solvent, supplementing with a certain minor quantity of water, adding a solution comprising aqueous HCl mixed into said organic solvent, and harvesting Varoglutamstat Hydrochloride crystals.

In particular, said process of the invention comprises the steps of:
  i. Dissolving Varoglutamstat free base in a polar aprotic water-mixable organic solvent;
  ii. Addition of water to adjust a definite total water content in the reaction mixture;
  iii. Addition of a solution comprising aqueous HCl mixed into the organic solvent to the solution of step ii.;

iv. Optionally adding seed crystals to the solution of step iii.;

V. Ripening the resulting mixture of step iii. and/or step iv. for a time period suitable to form Varoglutamstat Hydrochloride crystals;

vi. Further addition of polar aprotic water-mixable organic solvent;

vii. Cooling of the suspension obtained in step vi.; and viii. Harvesting the Varoglutamstat Hydrochloride crystals.

The organic solvent used in the process of the invention is preferably an organic solvent which facilitates the crystal formation of Varoglutamstat Hydrochloride. Crystal formation of Varoglutamstat Hydrochloride has been shown herein with isopropanol as well as with aqueous acetone as organic solvent. So, the organic solvent used in the process of the invention is more preferably selected from the group consisting of isopropanol and acetone. Varoglutamstat Hydrochloride crystals with favorable characteristics for drug development were obtained when a polar aprotic water-mixable organic solvent, such as acetone was used as organic solvent containing a small amount of water. So, in a more preferred embodiment, the organic solvent is acetone. Most preferably, said acetone is aqueous acetone, i.e. contains small amounts of water, e.g. 221 mg of water per mmol Varoglutamstat free base.

Suitably, in step i, 1.0 eq. of Varoglutamstat free base are dissolved in 3 to 7 vol., preferably 4 to 6 vol., most preferably 5 vol. acetone. (for a definition of vol., cf. Example 4.2)

In some embodiments, in step ii, water is added to the solution of step i in order to adjust a final water content of 150 to 300 mg, preferably 200 to 250 mg, most preferably 221 mg per mmol Varoglutamstat free base.

In some embodiments of the process of the invention, the solution of step i. is heated to a temperature within the range of 35 to 55° C., preferably 40° C., and steps ii. to v. are performed within a temperature range of 35 to 55° C., preferably 45±5° C.

In a further embodiment, 0.6 to 1.2 eq., preferably 0.7 to 1.1 eq. of HCl, more preferably 0.8 to 1.0 eq., most preferably 0.95 eq of HCl (aqueous 32-37% w/w) in acetone are added in step iii. to the solution of step ii.

The time period suitable to form Varoglutamstat Hydrochloride crystals in step v. is at least 30 min, preferably between 30 to 60 min, more preferably 30 min, 40 min, 50 min or 60 min.

The process of the invention further comprises step vi., in which further amounts of the polar aprotic water-mixable organic solvent, most preferably acetone, are added to the suspension of step v. followed by stirring of the suspension at a temperature of 30° C. to 55° C., most preferably 45±5° C. for at least 45 min., preferably 45 to 90 min, more preferably 45 min, 60 min, 75 min or 90 min.

After step vi., the process of the invention suitably comprises the further step vii. of cooling the suspension of step vi. to a temperature of 15° C. to 25° C., preferably 20±5° C., over a time period of at least 45 min, preferably 45 min. to 90 min, more preferably more preferably 45 min, 60 min, 75 min or 90 min.

After cooling down to 15° C. to 25° C., preferably 20±5° C., the suspension is suitably further stirred for a time period of at least 1 h, preferably 60 min to 120 min, more preferably 60 min, 70 min, 80 min, 90 min, 100 min, 110 min or 120 min.

The harvesting of step viii. is suitably performed by filtration and drying of said Varoglutamstat Hydrochloride crystals. Step viii. of harvesting may include further rinsing of the solids obtained by filtration, e.g. rinsing once or twice, with a suitable solvent. Best results were achieved when the solids obtained by filtration were first rinsed with an acetone/water mixture, and rinsed for a second and third time with pure acetone.

The ratio of acetone/water used in said rinsing step is preferably in the range of 48/0.0 to 48/15.0 v/v, more preferably 48/1.0 to 48/5.0 v/v. Most preferably the ratio of the acetone/water in said rinsing step is 48/1.4 or 48/1.315 v/v, wherein an acetone/water ratio of 48/1.315 is corresponding to a total water content of 221 mg/mmol.

In general terms, the invention provides a process for preparing a crystalline Hydrochloride salt of Varoglutamstat, said process comprising dissolving Varoglutamstat free base in aqueous acetone, supplementing with a certain quantity of water, adding a solution comprising aqueous HCl mixed into said organic solvent, and harvesting Varoglutamstat Hydrochloride crystals.

The highest reproducibility of Varoglutamstat Hydrochloride crystallization was achieved under the following conditions:

Use of 0.95 eq of HCl (aqueous 32-37% w/w) in acetone were found optimal regarding the purity.

Addition of a suspension of seeds in acetone directly after completed dosage of HCl/acetone.

A ripening period of at least 30 min before the dosage of acetone is started.

The optimal amount of total water within the reaction mixture was found to be 221 mg per mmol free base in a setting of acetone (8 vol) and 0.95 eq of HCl (aqueous 32% w/w) procedure.

The use of 16 vol of acetone to complete the crystallization.

The final crystallization temperature is to be set to 20±5° C. and the optimal final stirring time is 1 h.

The optimal suction filter regime consists of a 3-fold rinse: 1st rinse. with acetone/water mixture in the mixture ratio of the solvent used for the salt formation followed by two rinses with pure acetone.

After checking three different grades of free base containing typical production related impurities (e.g., HCl consuming organic bases) the exact determination of the total water content as well as the determination of the total HCl consumption and the assay of the free base PQ912 was identified to be important to ensure a controlled nucleation.

In a most preferred embodiment of the third aspect of the invention, the process of the invention comprises the steps of:

i. Dissolving 1 eq. Varoglutamstat free base per 5 vol. acetone and heating the solution to 45±5° C.;

ii Addition of water to reach a final amount of 221 mg water per mmol free base and keeping the solution at 45±5° C.;

iii. Addition of a solution comprising 3 vol. acetone and 0.95 eq of aqueous HCl (32-37% w/w) to the solution of step ii;

iv. Adding seed crystals to the solution of step iii;

v. Incubating the resulting suspension of step iii. and/or step iv. for a time period suitable to form Varoglutamstat Hydrochloride crystals (ripening period);

vi. Further addition of 16 vol. acetone and keeping the temp. of the suspension at 45±5° C.;

vii. Cooling of the suspension obtained in step vi. to 20±5° C.; and viii. Stirring the suspension of step vii;

ix. Harvesting the Varoglutamstat Hydrochloride crystals by filtration;

x. Rinsing the solids obtained by filtration in step ix. with an acetone/water mixture of 48:1.6 v/v;

xi. Rinsing the solids of step x. twice with pure acetone; and xii. Drying the Varoglutamstat Hydrochloride crystals.

Step xii. is suitably performed until the weight of the product is constant.

The invention further provides the Hydrochloride salt of Varoglutamstat according to the invention as described herein, which has been obtained by the process of the third aspect of the invention.

Varoglutamstat Hydrochloride, as provided by the present invention, is an inhibitor of glutaminyl cyclase (QC, EC 2.3.2.5, also named glutaminyl-peptide cyclotransferase, QPCT) and isoenzymes thereof and is suitable for use in treating conditions in which inhibition of QC and isoenzymes thereof is indicated. A preferred isoenzyme is isoQC, also named glutaminyl-peptide cyclotransferase-like protein (QPCTL). QC and isoQC catalyze the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

BRIEF DESCRIPTION OF THE DRAWINGS

The following drawings are provided to illustrate certain aspects and features of inventions claimed herein.

FIG. 32: Comparative optical microscopy observation (with cross-polarized light) of Varoglutamstat HCl obtained in example 4.2 and example 4.3.

DETAILED DESCRIPTION OF THE INVENTION

Therapeutic Uses

Figure 1:
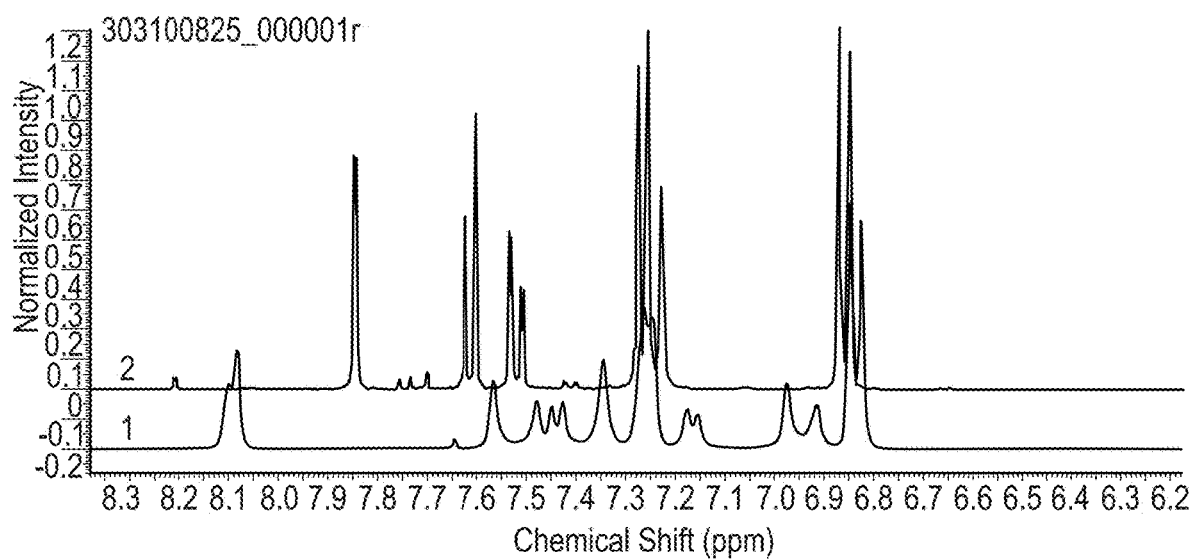
FIG. 1: Example for the proof of free-base and counter-ion interaction shown by NMR overlay of the aromatic region from free base (bottom) and the protonated form taken from an experiment with hydrochloric acid in isopropyl acetate (recorded in DMSO-d6).

In a fourth aspect, the present invention provides the use of Varoglutamstat Hydrochloride, as described herein, for use in methods of preventing, alleviating or treating of various diseases.

Physiological substrates of QC (EC) and/or isoQC in mammals are, e.g. amyloid beta-peptides (3-40), (3-42), (11-40) and (11-42), ABri, ADan, Gastrin, Neurotensin, FPP, CCL2, CCL7, CCL8, CCL16, CCL18, Fractalkine, Orexin A, [Gln$^3$]-glucagon (3-29), [Gln$^5$]-substance P(5-11) and the peptide QYNAD (SEQ ID NO: 20). For further details see table 1.

TABLE 1

Amino acid sequences of physiological active peptides with an N-terminal glutamine or glutamate residue, which are prone to be cyclized to final pGlu - and precursors thereof, which are cleaved under physiological conditions to liberate a glutamate at the N-terminus

| Peptide (SEQ ID NO) | Amino acid sequence | Function |
| --- | --- | --- |
| Abeta(1-42) (SEQ ID NO: 1) | Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g., in Alzheimer's Disease, Familial British Dementia, Familial Danish Dementia, Down Syndrome |
| Abeta(1-40) (SEQ ID NO: 2) | Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g., in Alzheimer's Disease, Familial British Dementia, Familial Danish Dementia, Down Syndrome |
| Abeta(3-42) (SEQ ID NO: 3) | Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g., in Alzheimer's Disease, Familial British Dementia, Familial Danish Dementia, Down Syndrome |
| Abeta(3-40) (SEQ ID NO: 4) | Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g., in Alzheimer's Disease, Familial British Dementia, Familial Danish Dementia, Down Syndrome |
| Abeta(11-42) (SEQ ID NO: 16) | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g., in Alzheimer's Disease, Familial British Dementia, Familial Danish Dementia, Down Syndrome |
| Abeta(11-40) (SEQ ID NO: 17) | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g., in Alzheimer's Disease, Familial British Dementia, Familial Danish Dementia, Down Syndrome |
| Abri (SEQ ID NO: 18) | EASNCFA IRHFENKFAV ETLIC SRTVKKNIIEEN | Pyroglutamated form plays a role in Familial British Dementia |
| Adan (SEQ ID NO: 19) | EASNCFA IRHFENKFAV ETLIC FNLFLNSQEKHY | Pyroglutamated form plays a role in Familial Danish Dementia |
| Gastrin 17 SWISS-PROT: P01350 (SEQ ID NO: 5) | QGPWL EEEEEAYGWM DF (amide) | Gastrin stimulates the stomach mucosa to produce and secrete hydrochloric acid and the pancreas to secrete its digestive enzymes. It also stimulates smooth muscle contraction and increases blood circulation and water secretion in the stomach and intestine. |
| Neurotensin SWISS-PROT: P30990 (SEQ ID NO: 6) | QLYENKPRRP YIL | Neurotensin plays an endocrine or paracrine role in the regulation of fat metabolism. It causes contraction of smooth muscle. |
| FPP | QEP amide | A tripeptide related to thyrotrophin releasing hormone (TRH), is found in seminal plasma. Recent evidence obtained in vitro and |

TABLE 1-continued

Amino acid sequences of physiological active peptides with an N-terminal glutamine or glutamate residue, which are prone to be cyclized to final pGlu - and precursors thereof, which are cleaved under physiological conditions to liberate a glutamate at the N-terminus

| Peptide (SEQ ID NO) | Amino acid sequence | Function |
|---|---|---|
| | | in vivo showed that FPP plays an important role in regulating sperm fertility. |
| TRH SWISS-PROT: P20396 | QHP amide | TRH functions as a regulator of the biosynthesis of TSH in the anterior pituitary gland and as a neurotransmitter/neuromodulator in the central and peripheral nervous systems. |
| GnRH SWISS-PROT: P01148 (SEQ ID NO: 7) | QHWSYGL RP(G) amide | Stimulates the secretion of gonadotropins; it stimulates the secretion of both luteinizing and follicle-stimulating hormones. |
| CCL16 (small inducible cytokine A16) SWISS-PROT: O15467 (SEQ ID NO: 8) | QPKVPEW VNTPSTCCLK YYEKVLPRRL VVGYRKALNC HLPAIIFVTK RNREVCTNPN DDWVQEYIKD PNLPLLPTRN LSTVKIITAK NGQPQLLNSQ | Shows chemotactic activity for lymphocytes and monocytes but not neutrophils. Also shows potent myelosuppressive activity, suppresses proliferation of myeloid progenitor cells. Recombinant SCYA16 shows chemotactic activity for monocytes and THP-1 monocytes, but not for resting lymphocytes and neutrophils. Induces a calcium flux in THP-1 cells that were desensitized by prior expression to RANTES. |
| CCL8 (small inducible cytokine A8) SWISS-PROT: P80075 (SEQ ID NO: 9) | QPDSVSI PITCCFNVIN RKIPIQRLES YTRITNIQCP KEAVIFKTKR GKEVCADPKE RWVRDSMKHL DQIFQNLKP | Chemotactic factor that attracts monocytes, lymphocytes, basophils, and eosinophils. May play a role in neoplasia and inflammatory host responses. This protein can bind heparin. |
| CCL2 (MCP-1, small inducible cytokine A2) SWISS-PROT: P13500 (SEQ ID NO: 10) | QPDAINA PVTCCYNFTN RKISVQRLAS YRRITSSKCP KEAVIFKTIV AKEICADPKQ KWVQDSMDHL DKQTQTPKT | Chemotactic factor that attracts monocytes and basophils but not neutrophils or eosinophils. Augments monocyte anti-tumor activity. Has been implicated in the pathogenesis of diseases characterized by monocytic infiltrates, like psoriasis, rheumatoid arthritis, or atherosclerosis. May be involved in the recruitment of monocytes into the arterial wall during the disease process of atherosclerosis. Binds to CCR2 and CCR4. |
| CCL18 (small inducible cytokine A18) SWISS-PROT: P55774 (SEQ ID NO: 11) | QVGTNKELC CLVYTSWQIP QKFIVDYSET SPQCPKPGVI LLTKRGRQIC ADPNKKWVQK YISDLKLNA | Chemotactic factor that attracts lymphocytes but not monocytes or granulocytes. May be involved in B cell migration into B cell follicles in lymph nodes. Attracts naive T lymphocytes toward dendritic cells and activated macrophages in lymph nodes, has chemotactic activity for naive T cells, CD4+ and CD8+ |

TABLE 1-continued

Amino acid sequences of physiological active peptides with an N-terminal glutamine or glutamate residue, which are prone to be cyclized to final pGlu - and precursors thereof, which are cleaved under physiological conditions to liberate a glutamate at the N-terminus

| Peptide (SEQ ID NO) | Amino acid sequence | Function |
|---|---|---|
| | | T cells and thus may play a role in both humoral and cell-mediated immunity responses. |
| Fractalkine (neurotactin) SWISS-PROT: P78423 (SEQ ID NO: 12) | QHHGVT KCNITCSKMT SKIPVALLIH YQQNQASCGK RAIILETROH RLFCADPKEQ WVKDAMQHLD RQAAALTRNG GTFEKQIGEV KPRTTPAAGG MDESVVLEPE ATGESSSLEP TPSSQEAQRA LGTSPELPTG VTGSSGTRLP PTPKAQDGGP VGTELFRVPP VSTAATWQSS APHQPGPSLW AEAKTSEAPS TQDPSTQAST ASSPAPEENA PSEGQRVWGQ GQSPRPENSL EREEMGPVPA HTDAFQDWGP GSMAHVSVVP VSSEGTPSRE PVASGSWTPK AEEPIHATMD PQRLGVLITP VPDAQAATRR QAVGLLAFLG LLFCLGVAMF TYQSLQGCPR KMAGEMAEGL RYIPRSCGSN SYVLVPV | The soluble form is chemotactic for T cells and monocytes, but not for neutrophils. The membrane-bound form promotes adhesion of those leukocytes to endothelial cells. May play a role in regulating leukocyte adhesion and migration processes at the endothelium binds to CX3CR1. |
| CCL7 (small inducible cytokine A7) SWISS-PROT: P80098 (SEQ ID NO: 13) | QPVGINT STTCCYRFIN KKIPKQRLES YRRTTSSHCP REAVIFKTKL DKEICADPTQ KWVQDFMKHL DKKTQTPKL | Chemotactic factor that attracts monocytes and eosinophils, but not neutrophils. Augments monocyte anti-tumor activity. Also induces the release of gelatinase B. This protein can bind heparin. Binds to CCR1, CCR2 and CCR3. |
| Orexin A (Hypocretin-1) SWISS-PROT O43612 (SEQ ID NO: 14) | QPLPDCCRQK TCSCRLYELL HGAGNHAAGI LTL | Neuropeptide that plays a significant role in the regulation of food intake and sleep-wakefulness, possibly by coordinating the complex behavioural and physiologic responses of these complementary homeostatic functions. It plays also a broader role in the homeostatic regulation of energy metabolism, autonomic function, hormonal balance and the regulation of body fluids. Orexin-A binds to both OX1R and OX2R with a high affinity. |
| Substance P (SEQ ID NO: 15) | RPK PQQFFGLM | Belongs to the tachykinins. Tachykinins are active peptides which excite neurons, evoke behavioural responses, are potent vasodilators and secretagogues, and contract (directly or indirectly) many smooth muscles. |
| QYNAD (SEQ ID NO: 20) | Gln-Tyr-Asn-Ala-Asp | Acts on voltage-gated sodium channels. |
| CD47 UNIPROT: Q08722 (SEQ ID NO: 21) | MWPLVAALLLGSACCGS AQLLFNKTKSVEFTFCNDTVVIP CFVTNMEAQNTTEVYVKWKFK GRDIYTFDGALNKSTVPTDFSSA KIEVSQLLKGDASLKMDKSDAV SHTGNYTCEVTELTREGETIIELK YRVVSWFSPNENILIVIFPIFAILL | Part of the CD47-SIRPα signalling system, involved in cancer, proliferative disorders, atherosclerosis, fibrotic disease, and infectious disease |

TABLE 1-continued

Amino acid sequences of physiological active peptides with an N-terminal glutamine or glutamate residue, which are prone to be cyclized to final pGlu - and precursors thereof, which are cleaved under physiological conditions to liberate a glutamate at the N-terminus

| Peptide (SEQ ID NO) | Amino acid sequence | Function |
|---|---|---|
| | FWGQFGIKTLKYRSGGMDEKTI ALLVAGLVITVIVIVGAILFVPGE YSLKNATGLGLIVTSTGILILLHY YVFSTAIGLTSFVIAILVIQVIAYI LAVVGLSLCIAACIPMHGPLLISG LSILALAQLLGLVYMKFVASNQ KTIQPPRKAVEEPLNAFKESKGM MNDE | |

Glutamate is found in positions 3, 11 and 22 of the amyloid beta-peptide. Among them the mutation from glutamic acid (E) to glutamine (Q) in position 22 (corresponding to amyloid precursor protein APP 693, SWISS-PROT P05067) has been described as the so-called Dutch type cerebroarterial amyloidosis mutation.

The beta-amyloid peptides with a then terminal pyroglutamic acid residue resulting from conversion of residues in position 3, 11 and/or 22 upon N-terminal cleavage up to the respective amino acid have been described to be more cytotoxic and hydrophobic than the amyloid beta-peptides 1-40 (42/43) (Saido T. C. 2000 Medical Hypotheses 54 (3): 427-429).

The multiple N-terminal variations, e.g. Abeta (3-40), Abeta (3-42), Abeta (11-40) and Abeta (11-42), can be generated from the full length peptides Abeta (1-40) and Abeta (1-42) by the beta-secretase enzyme beta-site amyloid precursor protein-cleaving enzyme (BACE) by proteolysis at different sites (Huse J. T. et al. 2002 J. Biol. Chem. 277 (18): 16278-16284), and/or by aminopeptidase or dipeptidylaminopeptidase processing. In all cases, cyclization of the then N-terminally occurring glutamic acid residue is catalyzed by QC.

Transepithelial transducing cells, particularly the gastrin (G) cell, co-ordinate gastric acid secretion with the arrival of food in the stomach. Recent work showed that multiple active products are generated from the gastrin precursor, and that there are multiple control points in gastrin biosynthesis. Biosynthetic precursors and intermediates (progastrin and Gly-gastrins) are putative growth factors; their products, the amidated gastrins, regulate epithelial cell proliferation, the differentiation of acid-producing parietal cells and histamine-secreting enterochromaffin-like (ECL) cells, and the expression of genes associated with histamine synthesis and storage in ECL cells, as well as acutely stimulating acid secretion. Gastrin also stimulates the production of members of the epidermal growth factor (EGF) family, which in turn inhibit parietal cell function but stimulate the growth of surface epithelial cells. Plasma gastrin concentrations are elevated in subjects with *Helicobacter pylori*, who are known to have increased risk of duodenal ulcer disease and gastric cancer (Dockray, G. J. 1999 J Physiol 15 315-324).

The peptide hormone gastrin, released from antral G cells, is known to stimulate the synthesis and release of histamine from ECL cells in the oxyntic mucosa via CCK-2 receptors. The mobilized histamine induces acid secretion by binding to the H (2) receptors located on parietal cells. Recent studies suggest that gastrin, in both its fully amidated and less processed forms (progastrin and glycine-extended gastrin), is also a growth factor for the gastrointestinal tract. It has been established that the major trophic effect of amidated gastrin is for the oxyntic mucosa of stomach, where it causes increased proliferation of gastric stem cells and ECL cells, resulting in increased parietal and ECL cell mass. On the other hand, the major trophic target of the less processed gastrin (e.g., glycine-extended gastrin) appears to be the colonic mucosa (Koh, T. J. and Chen, D. 2000 Regul Pept 9337-44).

Neurotensin (NT) is a neuropeptide implicated in the pathophysiology of schizophrenia that specifically modulates neurotransmitter systems previously demonstrated to be misregulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioral and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 Biol Psychiatry 50 856-872).

Fertilization promoting peptide (FPP), a tripeptide related to thyrotrophin releasing hormone (TRH), is found in seminal plasma. Recent evidence obtained in vitro and in vivo showed that FPP plays an important role in regulating sperm fertility. Specifically, FPP initially stimulates nonfertilizing (uncapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in uncapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on", others possibly being involved in the acrosome reaction itself. Calcitonin and angiotensin II, also found in seminal plasma, have similar effects in vitro on uncapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 Vitam Horm 63, 1-28).

CCL2 (MCP-1), CCL7, CCL8, CCL16, CCL18 and fractalkine play an important role in pathophysiological conditions, such as suppression of proliferation of myeloid progenitor cells, neoplasia, inflammatory host responses, cancer, psoriasis, rheumatoid arthritis, atherosclerosis, vasculitis, humoral and cell-mediated immunity responses, leukocyte adhesion and migration processes at the endothelium, inflammatory bowel disease, restenosis, pulmonary fibrosis, pulmonary hypertension, liver fibrosis, liver cirrhosis, nephrosclerosis, ventricular remodeling, heart failure, arteriopathy after organ transplantations and failure of vein grafts.

A number of studies have underlined in particular the crucial role of MCP-1 for the development of atherosclerosis (Gu, L., et al., (1998) Mol. Cell 2, 275-281; Gosling, J., et al., (1999) J Clin. Invest 103, 773-778); rheumatoid arthritis (Gong, J. H., et al., (1997) J Exp. Med 186, 131-137; Ogata, H., et al., (1997) J Pathol. 182, 106-114); pancreatitis (Bhatia, M., et al., (2005) Am. J Physiol Gastrointest. Liver Physiol 288, G1259-G1265); Alzheimer's disease (Yamamoto, M., et al., (2005) Am. J Pathol. 166, 1475-1485); lung fibrosis (Inoshima, I., et al., (2004) Am. J Physiol Lung Cell Mol. Physiol 286, L1038-L1044); and graft rejection (Saiura, A., et al., (2004) Arterioscler. Thromb. Vasc. Biol. 24, 1886-1890). Furthermore, MCP-1 might also play a role in gestosis (Katabuchi, H., et al., (2003) Med Electron Microsc. 36, 253-262), as a paracrine factor in tumor development (Ohta, M., et al., (2003) Int. J Oncol. 22, 773-778; Li, S., et al., (2005) J Exp. Med 202, 617-624), neuropathic pain (White, F. A., et al., (2005) Proc. Natl. Acad. Sci. U.S.A) and AIDS (Park, I. W., Wang, J. F., and Groopman, J. E. (2001) Blood 97, 352-358; Coll, B., et al., (2006) Cytokine 34, 51-55).

MCP-1 levels are increased in CSF of AD patients and patients showing mild cognitive impairment (MCI) (Galimberti, D., et al., (2006) Arch. Neurol. 63, 538-543). Furthermore, MCP-1 shows an increased level in serum of patients with MCI and early AD (Clerici, F., et al., (2006) Neurobiol. Aging 27, 1763-1768).

Several cytotoxic T lymphocyte peptide-based vaccines against hepatitis B, human immunodeficiency virus and melanoma were studied in clinical trials. One interesting melanoma vaccine candidate alone or in combination with other tumor antigens, is the decapeptide ELA. This peptide is a Melan-A/MART-1 antigen immunodominant peptide analog, with an N-terminal glutamic acid. It has been reported that the amino group and gamma-carboxylic group of glutamic acids, as well as the amino group and gamma-carboxamide group of glutamines, condense easily to form pyroglutamic derivatives. To overcome this stability problem, several peptides of pharmaceutical interest have been developed with a pyroglutamic acid instead of N-terminal glutamine or glutamic acid, without loss of pharmacological properties. Unfortunately compared with ELA, the pyroglutamic acid derivative (PyrELA) and also the N-terminal acetyl-capped derivative (AcELA) failed to elicit cytotoxic T lymphocyte (CTL) activity. Despite the apparent minor modifications introduced in PyrELA and AcELA, these two derivatives probably have lower affinity than ELA for the specific class I major histocompatibility complex. Consequently, in order to conserve full activity of ELA, the formation of PyrELA must be avoided (Beck A. et al. 2001, J Pept Res 57 (6): 528-38.).

Orexin A is a neuropeptide that plays a significant role in the regulation of food intake and sleep-wakefulness, possibly by coordinating the complex behavioral and physiologic responses of these complementary homeostatic functions. It plays also a role in the homeostatic regulation of energy metabolism, autonomic function, hormonal balance and the regulation of body fluids.

Moreover, increased levels of the pentapeptide QYNAD (SEQ ID NO. 20) were identified in the cerebrospinal fluid (CSF) of patients suffering from multiple sclerosis or Guillain-Barré syndrome compared to healthy individuals (Brinkmeier H. et al. 2000, Nature Medicine 6, 808-811). There is a big controversy in the literature about the mechanism of action of the pentapeptide Gln-Tyr-Asn-Ala-Asp (QYNAD; SEQ ID NO. 20), especially its efficacy to interact with and block sodium channels resulting in the promotion of axonal dysfunction, which are involved in inflammatory autoimmune diseases of the central nervous system. But recently, it could be demonstrated that not QYNAD (SEQ ID NO. 20), but its cyclized, pyroglutamated form, pEYNAD, is the active form, which blocks sodium channels resulting in the promotion of axonal dysfunction. Sodium channels are expressed at high density in myelinated axons and play an obligatory role in conducting action potentials along axons within the mammalian brain and spinal cord. Therefore, it is speculated that they are involved in several aspects of the pathophysiology of inflammatory autoimmune diseases, especially multiple sclerosis, the Guillain-Barré syndrome and chronic inflammatory demyelinizing polyradiculoneuropathy.

Furthermore, QYNAD (SEQ ID NO. 20) is a substrate of the enzyme glutaminyl cyclase (QC, EC 2.3.2.5), which is also present in the brain of mammals, especially in human brain. Glutaminyl cyclase effectively catalyzes the formation of pEYNAD from its precursor QYNAD (SEQ ID NO. 20).

Hatherly et al. discovered that CD47 contains a glutamine residue at the N-terminus ("Paired Receptor Specificity Explained by Structures of Signal Regulatory Proteins Alone and Complexed with CD47". Molecular Cell 31, 266-277, Jul. 25, 2008). CD47 is therefore a potential substrate of QPCT/QPCTL upon cleavage of the CD47 signal sequence, which has been confirmed as such. Furthermore, Murata et al. reported in 2014 on the CD47-SIRPα signaling system and its physiological roles and therapeutic application (*The Journal of Biochemistry*, Volume 155, Issue 6, June 2014, Pages 335-344). CD47, an immunoglobulin superfamily protein, is a ligand for SIRPα, with the two proteins constituting a cell-cell communication system (the CD47-SIRPα signaling system). SIRPα is particularly abundant in the myeloid lineage of hematopoietic cells such as macrophages or dendritic cells (DCs), whereas CD47 is expressed ubiquitously. For example, interaction of CD47 on red blood cells with SIRPα on macrophages is thought to prevent the phagocytosis of the former cells by the latter cells, determining the lifespan of red blood cells. Recent studies further indicate that this signaling system plays important roles in engraftment of hematopoietic stem cells as well as in tumor immune surveillance through regulation of the phagocytic activity of macrophages. In the immune system, the CD47-SIRPα interaction is also important for the development of a subset of CD11c[+] DCs as well as organization of secondary lymphoid organs. Finally, the CD47-SIRPα signaling system likely regulates bone homeostasis by osteoclast development. Such emerged functions of the CD47-SIRPα signaling system thus nourish multiple therapeutic strategies for the treatment of cancer, autoimmune diseases and bone disorders. Inhibitors of QC or isoQC may interfere with the CD47-SIRPα signaling system in decreasing the amount of CD47 binding to SIRPα, and therefore may be useful in the treatment or prevention of cancer, proliferative disorders, atherosclerosis, fibrotic diseases, and infectious diseases.

The concept that glutaminyl cyclase (and its isoenzyme) is an enzymatic modifier of the CD47-SIRPα axis and a target for cancer immunotherapy has been described in detail within respective recent literature and is here incorporated by reference (Logtenberg, M. E. W. et al., Nature Med. 2019, 25, 612-619; Wu, Z. et al., Cell Res. 2019, 29, 502-505; Logtenberg, M. E. W. et al., Immunity 2020, 52, 742; Bresser, K. et al., Oncoimmunology 2022, 11, e2049486; Raaben, M. et al., EP 3 747 438 A1). Likewise, combinations of a QPCT/QPCTL inhibitor with antibodies targeting a tumor-associated antigen has been described for treatment of solid as well as hematologic tumors (Raaben, M. et al., EP 3 747 437 A1).

Furthermore, other substrates of QPCT and QPCTL described above, like CCL2 and CCL7, have likewise been described to contribute to the fate of tumors, and inhibition of their N-terminal conversion by glutaminyl cyclases to exhibit anti-tumoral potential (da Silva, R. B. et al., Nature Immunol 2022, 23, 568).

An indication for the involvement of QC/isoQC in kidney diseases was recently published by Kanemitsu et al. (Kanemitsu et al., Naunyn-Schmiedeberg's Archives of Pharmacology 2020, 394, 751-761), who reported that the chronic treatment with the (iso-) glutaminyl cyclase inhibitor PQ529 is a novel and effective approach for treating glomerulonephritis in chronic kidney disease. Three-week repeated administration of PQ529 (30 and 100 mg/kg, twice daily) significantly reduced the serum and urine CCL2 and urinary protein excretion in a dose-dependent manner. It was suggested that PQ529 suppresses the progression of inflammation-induced renal dysfunction by inhibiting the CCL2/CCR2 axis.

Accordingly, the present invention provides the use of Varoglutamstat Hydrochloride, as described herein, for the preparation of a medicament for the prevention or alleviation or treatment of a neurodegenerative disease selected from the group consisting of mild cognitive impairment, Alzheimer's disease, Familial British Dementia, Familial Danish Dementia, neurodegeneration in Down Syndrome, and Huntington's disease, or a diseases selected from Kennedy's disease, ulcer disease, duodenal cancer with or w/o *Helicobacter pylori* infections, colorectal cancer, Zolliger-Ellison syndrome, gastric cancer with or without *Helicobacter pylori* infections, pathogenic psychotic conditions, schizophrenia, infertility, neoplasia, inflammatory host responses, cancer, malign metastasis, melanoma, psoriasis, rheumatoid arthritis, atherosclerosis, pancreatitis, restenosis, impaired humoral and cell-mediated immune responses, leukocyte adhesion and migration processes in the endothelium, impaired food intake, impaired sleep-wakefulness, impaired homeostatic regulation of energy metabolism, impaired autonomic function, impaired hormonal balance or impaired regulation of body fluids, multiple sclerosis, the Guillain-Barré syndrome, chronic inflammatory demyelinizing polyradiculoneuropathy and periodontitis.

In another embodiment, the present invention provides the use of the Varoglutamstat Hydrochloride, as described herein, for the preparation of a medicament for the prevention or alleviation or treatment of a proliferative disease selected from the group consisting of leukemia, acute myeloid leukemia (AML), acute promyelocytic leukemia (APL), chronic myeloid leukemia (CML), acute lymphoblastic leukemia (ALL), T-cell acute lymphoblastic leukemia (T-ALL), lymphoma, B-cell lymphoma, T-cell lymphoma, Hodgkin's disease, non-Hodgkin's lymphoma (NHL), hairy cell lymphoma, Burkett's lymphoma, multiple myeloma (MM), myelodysplastic syndrome, lung cancer, adenocarcinoma, small cell lung cancer (SCLC), non-small cell lung cancer (NSCLC), mediastinum cancer, peritoneal cancer, mesothelioma, gastrointestinal cancer, gastric cancer, stomach cancer, bowel cancer, small bowel cancer, large bowel cancer, colon cancer, colon adenocarcinoma, colon adenoma, rectal cancer, colorectal cancer, leiomyosarcoma, breast cancer, gynaecological cancer, genito-urinary cancer, ovarian cancer, endometrial cancer, cervical cancer, prostate cancer, testicular cancer, seminoma, teratocarcinoma, liver cancer, kidney cancer, bladder cancer, urothelial cancer, biliary tract cancer, pancreatic cancer, exocrine pancreatic carcinoma, esophageal cancer, nasopharyngeal cancer, head and neck squamous cell carcinoma (HNSCC), skin cancer, squamous cancer, squamous cell carcinoma, Kaposi's sarcoma, melanoma, malignant melanoma, xeroderma pigmentosum, keratoacanthoma, bone cancer, bone sarcoma, osteosarcoma, rhabdomyosarcoma, fibrosarcoma, thyroid gland cancer, thyroid follicular cancer, adrenal gland cancer, nervous system cancer, brain cancer, astrocytoma, neuroblastoma, glioma, schwannoma, glioblastoma, or sarcoma; scleroderma, idiopathic pulmonary fibrosis, liver cirrhosis, lung fibrosis, bladder fibrosis, heart fibrosis, pancreas fibrosis, or myelofibrosis; an infectious disease; an infectious disease caused by a virus, bacterium, or protozoan; an infectious disease caused by a pathogen selected from: a lentivirus, human T-lymphotropic virus (HTLV), an hepadna virus, hepatitis B virus, a herpes virus, human papilloma virus, la crosse virus, *Yersinia* sp., *Yersinia pestis, Yersinia pseudotuberculosis, Yersinia enterocolitica, Franciscella* sp., *Helicobacter* sp., *Helicobacter pylori, Pasteurella* sp., *Vibrio* sp., *Vibrio cholerae, Vibrio parahemolyticus, Legionella* sp., *Legionella pneumophila, Listeria* sp., *Listeria monocytogenes, Mycoplasma* sp., *Mycoplasma hominis, Mycoplasma pneumoniae, Mycobacterium* sp., *Mycobacterium tuberculosis, Mycobacterium leprae, Rickettsia* sp., *Rickettsia rickettsii, Rickettsia typhi,* a *Plasmodium,* a *Trypanosoma,* a Giardia, a *Toxoplasma,* and a *Leishmania.*

In another embodiment, the present invention provides the use of the Varoglutamstat Hydrochloride, as described herein, for the preparation of a medicament for the prevention or alleviation or treatment of a kidney disease, wherein said kidney disease is an acute kidney disease (AKD) or a chronic kidney disease (CKD). Such CKD may be accompanied by a persistent inflammation. In a further embodiment, said kidney disease represents a condition selected from the group consisting of diabetic nephropathy, Focal Segmental Glomerulosclerosis (FSGS), glomerulonephritis, polycystic kidney disease, membranous nephropathy, obstructions of the urinary tract, vesicoureteral reflux, nephrotic syndrome, recurrent kidney infection (pyelonephritis), lupus and, other immune system diseases selected from the group consisting of polyarteritis nodosa, sarcoidosis, Good pasture syndrome and Henoch-Schönlein purpura. In some embodiments, said kidney disease is associated with an impaired glomerular filtration rate (GFR).

In a further embodiment, the invention provides the Varoglutamstat Hydrochloride polymorphic form, as described herein, for use in the prophylaxis, prevention, and/or treatment of the aforementioned diseases and conditions.

In a further embodiment, the invention relates to methods of prophylaxis, prevention, and/or treatment of the aforementioned diseases and conditions comprising the step of administering of a therapeutically effective amount of the Varoglutamstat Hydrochloride described herein to a subject in need thereof. Said subject is suitably a mammal, preferably a human.

Furthermore, by administration of the Varoglutamstat Hydrochloride according to the present invention to a mammal it can be possible to stimulate the proliferation of myeloid progenitor cells.

In addition, the administration of the Varoglutamstat Hydrochloride according to the present invention can lead to suppression of male fertility.

In a preferred embodiment, the present invention provides the use of the Varoglutamstat Hydrochloride described herein in combination with other agents, especially for the treatment of neurodegenerative diseases, and inflammatory diseases such as psoriasis, rheumatoid arthritis, atherosclerosis, pancreatitis, restenosis and multiple sclerosis.

Most preferably, said method and corresponding uses are for the treatment of a disease selected from the group consisting of mild cognitive impairment, Alzheimer's disease, Familial British Dementia, Familial Danish Dementia, neurodegeneration in Down Syndrome, Parkinson's disease and Chorea Huntington, comprising the administration of a therapeutically active amount of at least one of Varoglutamstat Hydrochloride of the invention to a mammal, preferably a human.

Especially preferred according to the invention is a method and corresponding uses for the treatment of a disease selected from the group consisting of mild cognitive impairment and Alzheimer's disease.

Even preferably, the present invention provides a method of treatment and corresponding uses for the treatment of rheumatoid arthritis, atherosclerosis, pancreatitis, and restenosis.

Even preferably, the present invention provides a method of treatment and corresponding uses for the treatment of periodontitis.

Even preferably, the present invention provides a method of treatment and corresponding uses for the treatment of solid and hematologic tumors.

Even preferably, the present invention provides a method of treatment and corresponding uses for the treatment of kidney diseases.

Pharmaceutical Combinations

In a preferred embodiment, the present invention provides a composition, preferably a pharmaceutical composition, comprising Varoglutamstat Hydrochloride or a polymorphic form thereof of the invention optionally in combination with at least one other agent selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs, anti-multiple sclerosis drugs and monoclonal antibodies.

More specifically, the aforementioned other agent is selected from the group consisting of anti-beta-amyloid antibodies such as aducanumab and leqembi, vaccines, cysteine protease inhibitors, PEP-inhibitors, LiCl, acetylcholinesterase (AChE) inhibitors, PIMT enhancers, inhibitors of beta secretases, inhibitors of gamma secretases, inhibitors of aminopeptidases, preferably inhibitors of dipeptidyl peptidases, most preferably DP IV inhibitors; inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents, MCP-1 antagonists or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS, anti-PD-L1 antibody, anti-CD19 antibody, anti-CD20 antibody, anti-CD38 antibody, ant-CD79b antibody, anti-SLAMF7 antibody, anti-Her2 antibody, anti-EGFR antibody, anti-VEGFR2 antibody, anti-CD20-CD47 bispecific antibody, anti-CD56 antibody, anti-TRP-1-PD-L1 bispecific antibody, and anti-CD271-sporin antibody Pharmaceutical Compositions The Varoglutamstat Hydrochloride as described herein is alternatively also named as compound(s))" of the invention.

To prepare the pharmaceutical compositions of this invention, the Varoglutamstat Hydrochloride polymorph described herein optionally in combination with at least one of the other aforementioned agents can be used as the active ingredient(s). The active ingredient(s) is intimately admixed with a pharmaceutical carrier according to conventional pharmaceutical compounding techniques, which carrier may take a wide variety of forms depending on the form of preparation desired for administration, e.g., oral, or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included.

Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful, and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated, and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol, or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration. For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of Varoglutamstat Hydrochloride of the present invention. When referring to these preformulation compositions as homogeneous, it is meant that the active ingredient is dispersed evenly throughout the composition so that the composition may be readily subdivided into equally effective dosage forms such as tablets, pills, and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

The pharmaceutical composition may contain between about 0.01 mg and 1000 mg, preferably about 5 to 800 mg, more preferably 100 to 600 mg of Varoglutamstat Hydrochloride of the present invention and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release, and sustained release formulations), granules, and powders, and liquid forms, such as solutions, syrups, elixirs, emulsions, and suspensions. Forms useful for parenteral administration include sterile solutions, emulsions, and suspensions.

Advantageously, Varoglutamstat Hydrochloride of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

Varoglutamstat Hydrochloride or the combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Varoglutamstat Hydrochloride or the combinations of the present invention may also be delivered by the use of monoclonal antibodies as individual carriers to which the compound molecules are coupled. Varoglutamstat Hydrochloride of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, Varoglutamstat Hydrochloride of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Varoglutamstat Hydrochloride or the combinations of this invention may be administered in any of the foregoing compositions and according to dosage regimens established in the art whenever treatment of the addressed disorders is required.

The daily dosage of the products may be varied over a wide range from 0.01 to 1800 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 300, 500 and 600 milligrams of each active ingredient or combinations thereof for the symptomatic adjustment of the dosage to the patient to be treated. An effective amount of the drug is ordinarily supplied at a dosage level ranging from about 0.1 mg/kg to about 300 mg/kg of body weight per day. Preferably, the range is from about 1 to about 50 mg/kg of body weight per day. Varoglutamstat Hydrochloride or the combinations of the present invention may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

In a further aspect, the invention also provides a process for preparing a pharmaceutical composition comprising Varoglutamstat Hydrochloride of the present invention, optionally in combination with at least one of the other aforementioned agents and a pharmaceutically acceptable carrier.

The compositions are preferably in a unit dosage form in an amount appropriate for the relevant daily dosage.

Suitable dosages, including especially unit dosages, of Varoglutamstat Hydrochloride of the present invention include the known dosages including unit doses as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

The present invention is further illustrated by the following non-limiting Examples.

Varoglutamstat ((S)-1-(1H-benzo[d]imidazol-5-yl)-5-(4-propoxyphenyl) imidazolidin-2-one) free base can be synthesized in accordance with the processes described in the literature, such as WO2011029920 A1, or as described in Example 1 below.

The following examples are for the purpose of illustration of the invention only and are not intended in any way to limit the scope of the present invention. It will thus be readily apparent to one skilled in the art that e.g., variations in scale of experiments might have an impact on optimized concentrations and/or time scales for certain parts of the processes. Thus, although the present invention has been specifically disclosed by preferred embodiments and optional features, modification and variation of the concepts herein disclosed may be resorted to by those skilled in the art, and that such modifications and variations are considered to be falling within the scope of the invention.

Examples

Example 1—Varoglutamstat Free Base Preparation

The synthetic route of the Varoglutamstat free base is a three-step process consisting of a Strecker synthesis, nitrile reduction and cyclisation, resulting in a racemic intermediate 5. The racemic intermediate is then separated into the enantiomers by chiral chromatography. The resulting (S)-enantiomer is the Varoglutamstat free base. The synthetic route is shown in Scheme 1.

Scheme 1

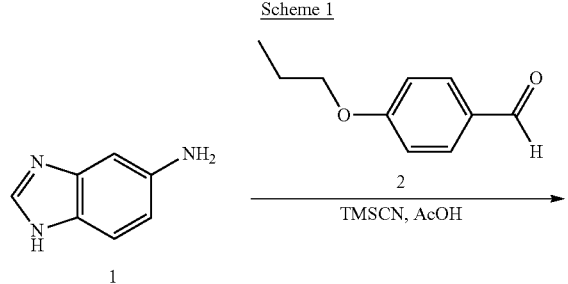

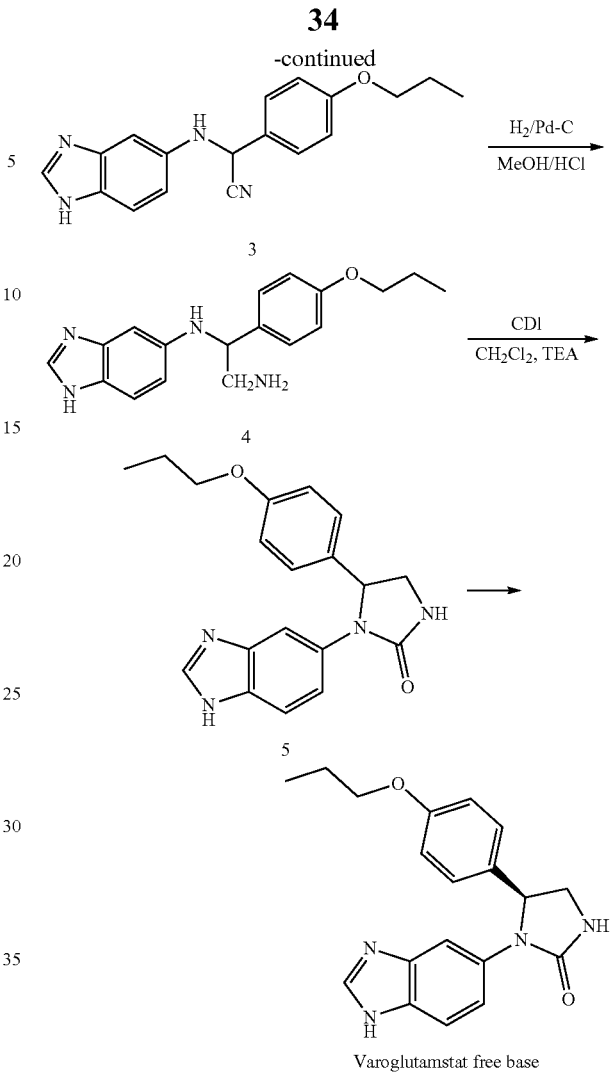

Varoglutamstat free base

The starting materials for synthesis step 1 (Strecker synthesis) are 5-aminobenzimidazole (1) and 4-propoxybenzaldehyde (2). The synthesis of Varoglutamstat free base was performed by formation of the Strecker product 3 followed by catalytic hydrogenation of the nitrile 3 resulting in the amine 4 and final cyclisation to the racemate 5. The Varoglutamstat free base was isolated from the racemate by a chiral chromatographic method applying chiral chromatography.

One equivalent of aldehyde 2 is dissolved in AcOH (5 mL in case of 4 mmol starting material) and 1.1 equivalents of amine 1 are added. 1 equivalent of TMSCN is then added to the mixture. The mixture was then stirred for 1.5 h at r.t. The mixture was then poured on ice/ammonia (containing 12 mL of a 25% aq. $NH_3$ solution in case of 4 mmol starting material). The aqueous layer was extracted 3 times by means of $CH_2Cl_2$, the organic phases were combined and dried. The solvent was removed and remains were taken up in MeOH and 1-2% of conc. HCl were added. The solution was subjected to hydrogenation (Pd/C 10%, $H_2$ 4 bar, 3 h, RT). After filtration, the solvent was evaporated and the remaining oil was dissolved in $CH_2Cl_2$, and TEA (2.2 equivalents) were added. After addition of carbonyldiimidazole (1.2 eq) the mixture was kept under reflux for 18 h. The solvent was removed, and the remaining oil was taken up in $CH_2Cl_2$, washed with water twice and subjected to column chromatography using a CHCl₃/MeOH gradient. After evaporation the remaining oil was subjected to chiral separation by chiral HPLC, column: Nucleocel Alpha RP-S, 250*21 mm (5 μm), eluent: 50/50 acetonitrile/water 50/50, flow 10 mL/min.

5 was synthesized starting from 1 (0.585 g, 4.4 mmol), 2 (0.632 mL, 4 mmol), TMSCN (0.5 mL, 4 mmol), Pd/C (10%, 0.02 g), TEA 0.558 mL, 4 mmol), di-(imidazole-1-yl) methanone (0.648 g, 4 mmol) as described above. Yield: 0.135 g (10%); MS m/z 337.0 (M+H)⁺; 1H NMR (d6-DMSO, 400 MHZ): δ 0.90-0.93 (m, 3H); 1.61-1.70 (m, 2H); 3.08-3.12 (m, H); 3.81-3.87 (m, 3H); 5.49-5.53 (m, H); 6.85 (d, 2H, J=8.3 Hz); 7.19 (s, H); 7.25 (d, 2H, J=8.7 Hz); 7.55 (dd, H, 3J=9.1 Hz, 4J=2.1 Hz); 7.62 (d, H, J=9.1 Hz); 7.86 (d, H, 4J=2.1 Hz); 9.21 (s, H), HPLC (λ=214 nm), [B]: rt 9.00 min (99%);

Varoglutamstat free base: chiral separation of 5: first eluting enantiomer; rt: 11.6 min, purity 99.15%, yield 0.042 g (31% of racemate)

Example 2: Investigation of the Varoglutamstat Free Base

Solubility Screening of the Varoglutamstat Free Base

The Varoglutamstat free base was prepared as described in Example 1.

75 mg of solid were transferred into a glass vial, a magnetic stir bar and 1.5 ml of solvent were added. The vials were heated to Tmax at 0.2° C./min and kept at Tmax for 15 min (Tmax for DCM: 40° C.; for TBME, Acetone: 55° C.; THF, MeOH: 65° C.; EtOAc, EtOH, IPA, MEK, ACN: 77° C., MeTHF, 2-pentanone: 78° C.; iPrOAc: 89° C.; nPrOH, Heptane, water, toluene, MIBK, DMSO, nBuOH: 97° C.). The vials were then cooled to 20° C. and stirred for another 30 min. When completely dissolved, additional solid material was added, and the vial equilibrated for at least 3 hours at 20° C.

The mother liquor was sampled and analyzed for content via HPLC versus an external standard solution (1-point calibration).

The results of the solubility screening of Varoglutamstat free base in a set of organic solvents revealed a good (e.g., methyl-isobutyl-ketone, dichloro-methane) to excellent solubility (≥30 mg/mL; e.g. in solvents such as acetone, tetrahydrofuran, methyl-tetrahydrofuran, methyl-ethylketone, 2-pentanone, acetonitrile, dimethylsulfoxide, and methanol, ethanol, isopropanol, n-propanol, and n-butanol. It was found to be poorly soluble or insoluble in tert-butyl-methyl-ketone, ethyl-acetate, isopropyl-acetate, heptane, and toluene. It was found to also be very poorly soluble in water (<1 mg/mL).

Concluding from this solubility screening, Varoglutamstat free base is highly soluble in certain organic solvents, including isopropanol (IPA) but is almost insoluble in water, forming a sticky/oily suspension.

Example 3: Screen for Suitable Counter Ions—Identification of Possible Salt Forms Example 3.1: Identification of Suitable Salt Forms: Varoglutamstat Salt Screening by Micro-Crystallization Experiments Procedure The Varoglutamstat free base was prepared as described in Example 1. The list of pharmaceutically acceptable acids tested within this salt screening is presented in Table 2.

TABLE 2

| Tested acids/resulting counter ions | |
|---|---|
| Counter ions | Acids |
| Oxalate | oxalic acid |
| Chloride | hydrochloric acid |
| Sulfate | Sulfuric acid |
| Aspartate | Aspartic Acid |
| Maleate | Maleic acid |
| Phosphate | Phosphoric acid |
| Mesylate | Methanesulfonic acid |
| Besylate | Benzenesulfonic acid |
| Camsylate | Camphorsulfonic acid |
| Tosylate | Toluenesulfonic acid (mono-hydrate) |

12 crystallization media were tested in this experimental setting:
Water and 6 organic solvents as single solvents (acetonitrile, isopropyl alcohol, ethanol, acetone, tetrahydrofuran, 1-propanol),
Mixtures of 5 of these organic solvents (acetonitrile, isopropyl alcohol, ethanol, acetone, tetrahydrofuran) with water (50/50, v/v).

Micro-crystallization experiments were performed in microplates, using the set of crystallization media listed above. All crystallization media were tested with each of the selected acids. Relative to Varoglutamstat free base, the counter-ions were introduced in small excess (10 to 12%). Micro-crystallization experiments were also performed with freebase alone and with the free acids alone in the same crystallization media to serve as reference samples. At the end of the crystallization experiments, the content of each well was first visually scanned to record where significant precipitants were present. Each of these samples was then characterized by optical microscopy between crossed polarizer and analyzer in order to identify the "counter-ions/crystallization medium" couples that have led to a crystalline sample. This allowed the identification of "crystallization hits".

Crystallization hits (potential salts) were then further characterized by Raman microscopy and, for confirmation when a given salt has been "confirmed" by Raman microscopy, by hot stage microscopy. These last analyses enabled a ranking of the various salt-hits.

Results

Out of the set of 10 studied acids/counterions within the Varoglutamstat salt screening study on microplates (see Table 2), only 4 formed a crystalline salt.

From these 4 acids, benzenesulfonic acid and camphorsulfonic acid have been found to lead to well crystallized materials in the studied experimental conditions.

Toluenesulfonic and maleic acid have only led to partially crystallized materials.

The 6 other tested acids (oxalic, hydrochloric, sulfuric, aspartic, phosphoric and methanesulfonic acids) were found not to be able to form a crystalline salt with the free base in the tested experimental conditions.

Hydrochloric acid did not form a crystalline salt with the Varoglutamstat free base within any of the solvents tested.

Recommendation from this experiment:
Further experiments intending to produce and to enable isolation of larger amounts of the above salts for characterization before selecting one to be developed, should therefore probably (and by order of priority) first focus on benzenesulfonate and camphorsulfonate, and then on toluenesulfonate and maleate.

Example 3.2: Identification of Suitable Salt Forms: Varoglutamstat Salt Screening In a second approach, further crystallization attempts were performed using isopropanol as solvent.

The Varoglutamstat free base was prepared as described in Example 1. For acids used within these salt forming experiments, cf. Table 3.

TABLE 3

Selected Acids in salt-screening experiments conducted in isopropanol as solvent and analytics performed on the isolated solids.*

| Acid | acid (mg) | isolated | aspect (s slime/oil, f solid, l solution) | Comments | counterion (IC, % found/ % th) | NMR |
|---|---|---|---|---|---|---|
| HCl | 58.5 | x | f | filtered | | ok |
| sulfuric acid | 23.0 | x | f | filtered | 17.7/22.6 | ok |
| TosOH | 39.0 | x | f | filtered | | ca. 1 eq TsOH |
| MsOH | 21.6 | | l | solution | | |
| oxalic acid | 20.3 | x | f | filtered | 20.1/21.1 | |
| maleic acid | 26.1 | x | f | filtered | | ca. 1 eq acid |
| malonic acid | 23.4 | | s | oil formed | | |
| phosphoric acid | 25.7 | | s | oil formed | | |
| fumaric acid | 26.0 | x | f | filtered | | ca. 1 eq acid |
| citric acid | 43.1 | | s | oil formed | | |

*IC: ion chromatography; % th: percentage calculated according to theory

Procedure

The general procedure for the screening consisted of the combination of the Varoglutamstat free base as a solid (1.75 mg each) with high excess of different acids in 0.75 mL of isopropanol. Solid acids and Varoglutamstat free base were mixed before isopropanol was added. When the acids were liquids or aqueous solutions, the respective amounts were added to the solution of Varoglutamstat free base in isopropanol. The mixtures were then heated for 30 minutes to 65° C. and then cooled slowly to ambient temperature. After this, the mixtures were stirred for at least 15 hours and checked for the formation of suspensions or solid matter. In the case of these being observed, these mixtures were filtered with no additional washing step. In case of the presence of sticky solids or crusts these materials were checked by microscopy. The results are shown in Table 4, and for the HCl salt in FIG. 2.

Filtrable solids were isolated and investigated by NMR for identification of counter-ion interaction presence as well as ion chromatography for stoichiometry.

Results

The hydrochloride, tosylate, oxalate, maleate and fumarate resulting from screening showed a formation of a salt with a clear stoichiometry and proof of the interaction with the counter ion (see example for the HCl salt in FIG. 1).

For such salts with a clear stoichiometry, their preparation was then repeated on 1 g scale (free base) in isopropanol with the acid slowly being added followed by seeding (seeds as obtained from the screening experiment). The solids were then further characterized with regard to:
  Handling of crystals,
  Crystal habit (microscopy, macroscopic): presence and shape of crystals,
  Crystallinity (quality of crystals, XRPD),
  Thermal analysis (DSC and TGA),
  Hygroscopicity (DVS), and
  Solubility in water.

Results

Within the set of 1 g scale repetition of experiments, the mixtures of the hydrochloride and the tosylate salt formation experiment dissolved completely after heating to 65° C.; and in case of the hydrochloride sample, seeding at the target temperature was needed in order to obtain a precipitate upon cooling. Furthermore, resulting suspensions had to be diluted with isopropanol after crystallization in order to allow filtration. This finding points towards a non-favorable proceeding with regard to crystallinity and handling of the process. The results are shown in Table 4.

TABLE 4

Summary of results for the salt screening experiments in isopropanol on 1 g scale ***

| Salt Form | Counter Ion* | crystallinity (by XRPD) | hygro-scopicity | Solubility in water [M] | melting point (° C. by DSC) |
|---|---|---|---|---|---|
| HCl | too low | good | high | 0.13 | 232 |
| TosOH | ca. 1:1 | good | low | 0.0036 | 198/211 |
| Oxalate | ca. 1.1 | low | high | — | none |
| Maleate | ca. 1:1 | none | high | — | 120** |
| Fumarate | ca. 1:1 | mediocre | high | — | none |
| free base | — | none | high | 0.00089 | 67 |

*Values for HCl and Oxalate by generic IC method and thus variations possible (for method see "Description of analytical procedures used in the Examples of the invention" below).
**potential decomposition.
*** the aqueous solubility was determined according to the procedure outlined in Example 4.1

The hydrochloride, tosylate, oxalate and fumarate were found to be partly crystalline in nature, with the tosylate as well as the hydrochloride showing clear crystallinity according to the XRPD data. In correlation to this, only the latter two salts have shown clear melting behavior with melting points in acceptable high range in comparison to the free base. In contrast to the tosylate, the hydrochloride exhibited a substantial hygroscopicity. (All results are presented in Table 3 and Table 4).

For both these salts, further characterization of their respective aqueous solubilities was performed. The hydrochloride salt showed a higher solubility in water by two orders of magnitude than the tosylate salt (see Table 4).

Example 3.3: Detailed Physical Characterization of the Varoglutamstat Hydrochloride Salt Obtained in Example 3.2

Identity

Figure 3:
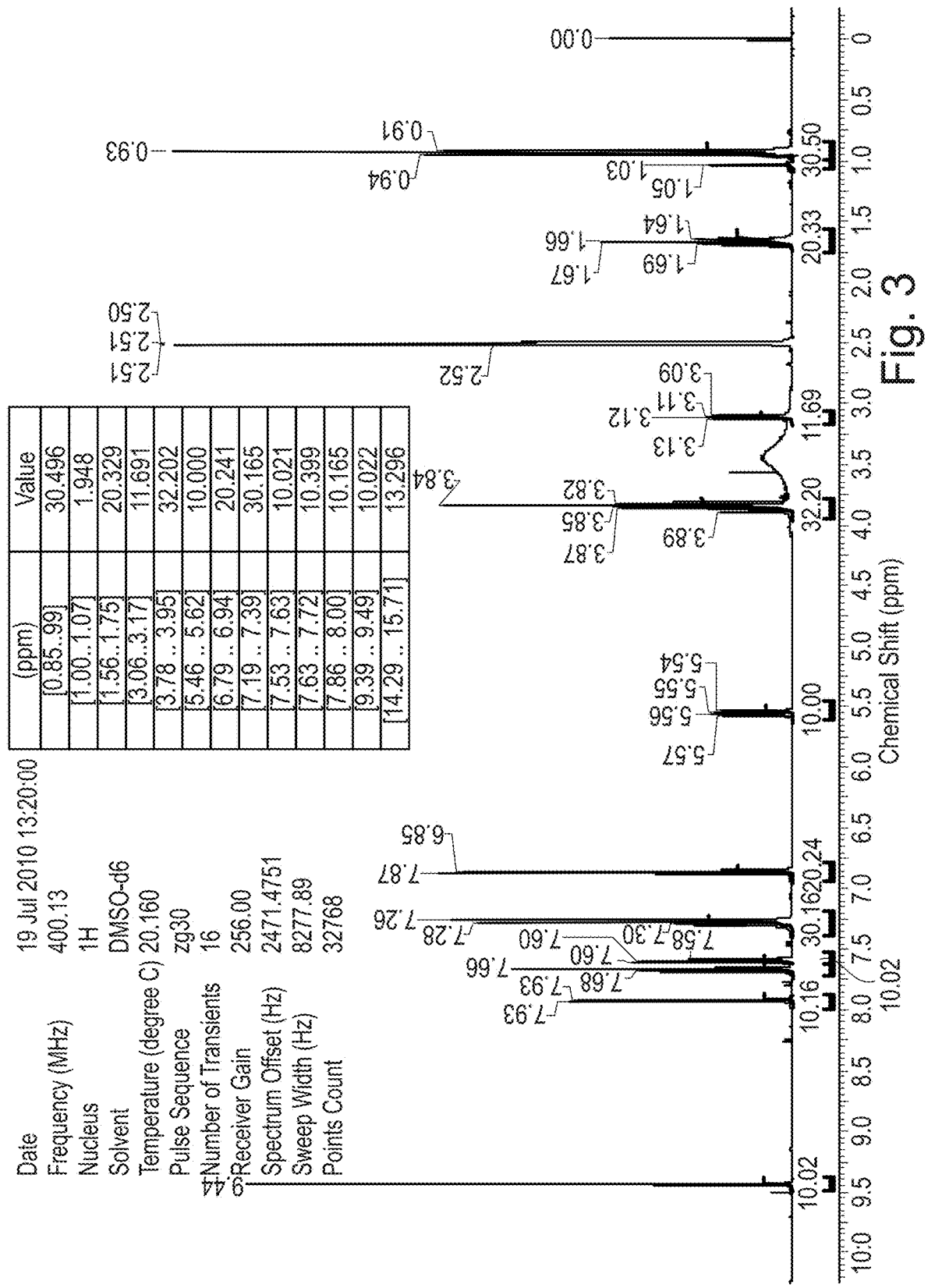
FIG. 3: NMR spectrum of the Hydrochloride salt prepared in Example 3.2 (recorded in DMSO-d6).

The identity of the Varoglutamstat Hydrochloride salt of Example 3.2 was confirmed by NMR analysis (see FIG. 3).

Handling of Crystals

The salt formation in isopropanol with aqueous HCl (as described in Example 3.2) was difficult to perform on 1 g scale. The addition of the acid suddenly led to thick suspensions with slow filtration speed.

Crystallinity (Crystal Habit, Microscopy)

Figure 2:
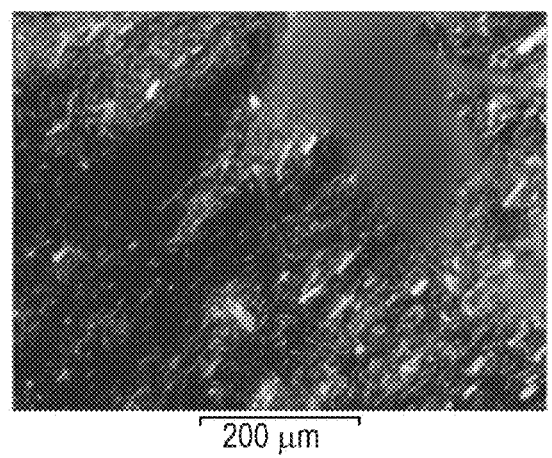
FIG. 2: Microscopy picture taken from the isolated solid out of an experiment performed with hydrochloric acid in isopropanol. The solvent was allowed to evaporate. The solid observed showed a hedgehog-like habit (macroscopically), with broken needles (microscopically).

The obtained suspensions either looked amorphous-like under the microscope or were found to be of a hair-like nature for the most part, also thin and broken needles were detected (for example picture see FIG. 2).

Crystallinity (Quality of Crystals, XRPD)

Figure 4:
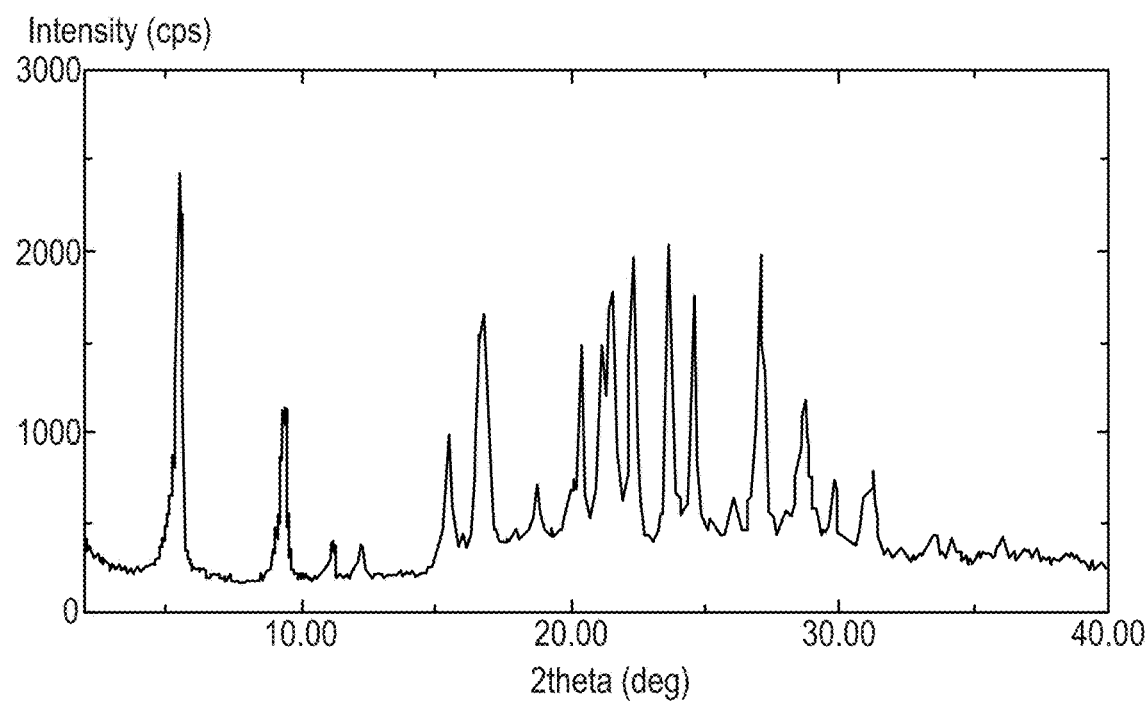
FIG. 4: XRPD of the HCl salt prepared according to Example 3.2.

The XRPD profile is shown in FIG. 4 and discussed also in Example 5.1 below: Amorphous material was detected as an amorphous halo was visible in the otherwise quite crystalline HCl adduct.

Thermal Analysis

Figure 5:
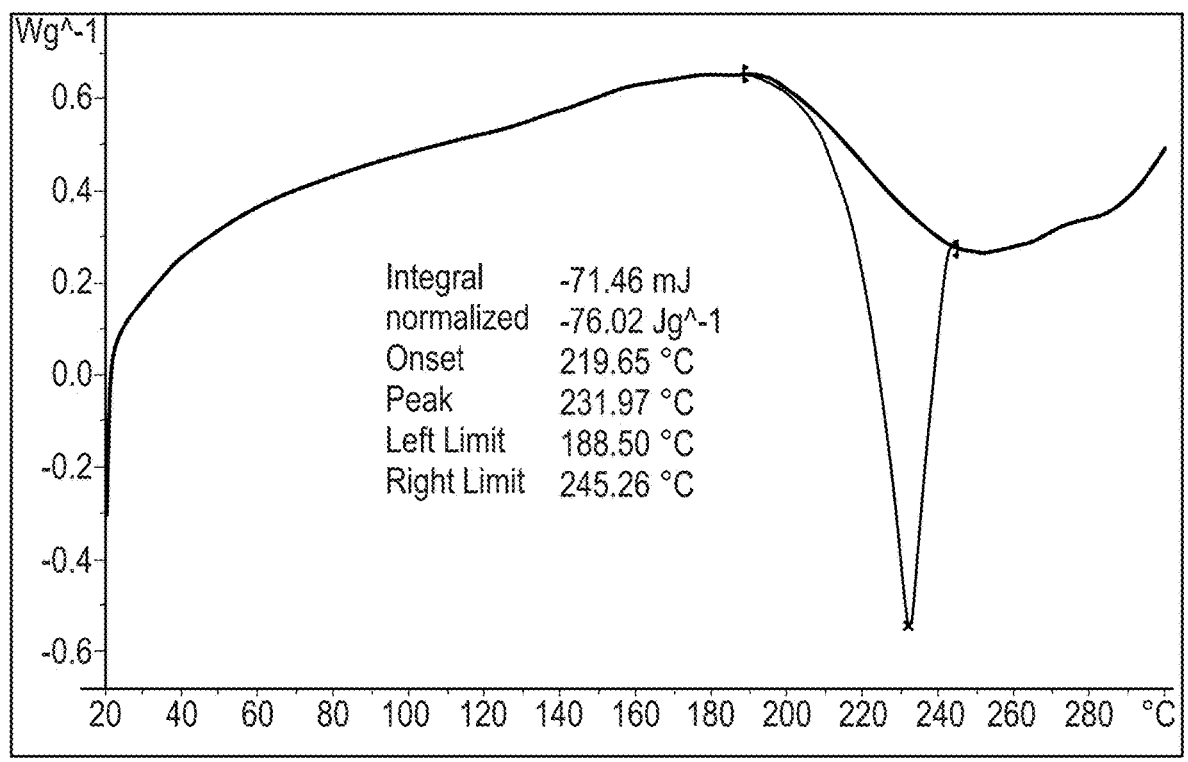
FIG. 5: DSC Thermogram of the HCl salt prepared according to Example 3.2.
Figure 6:
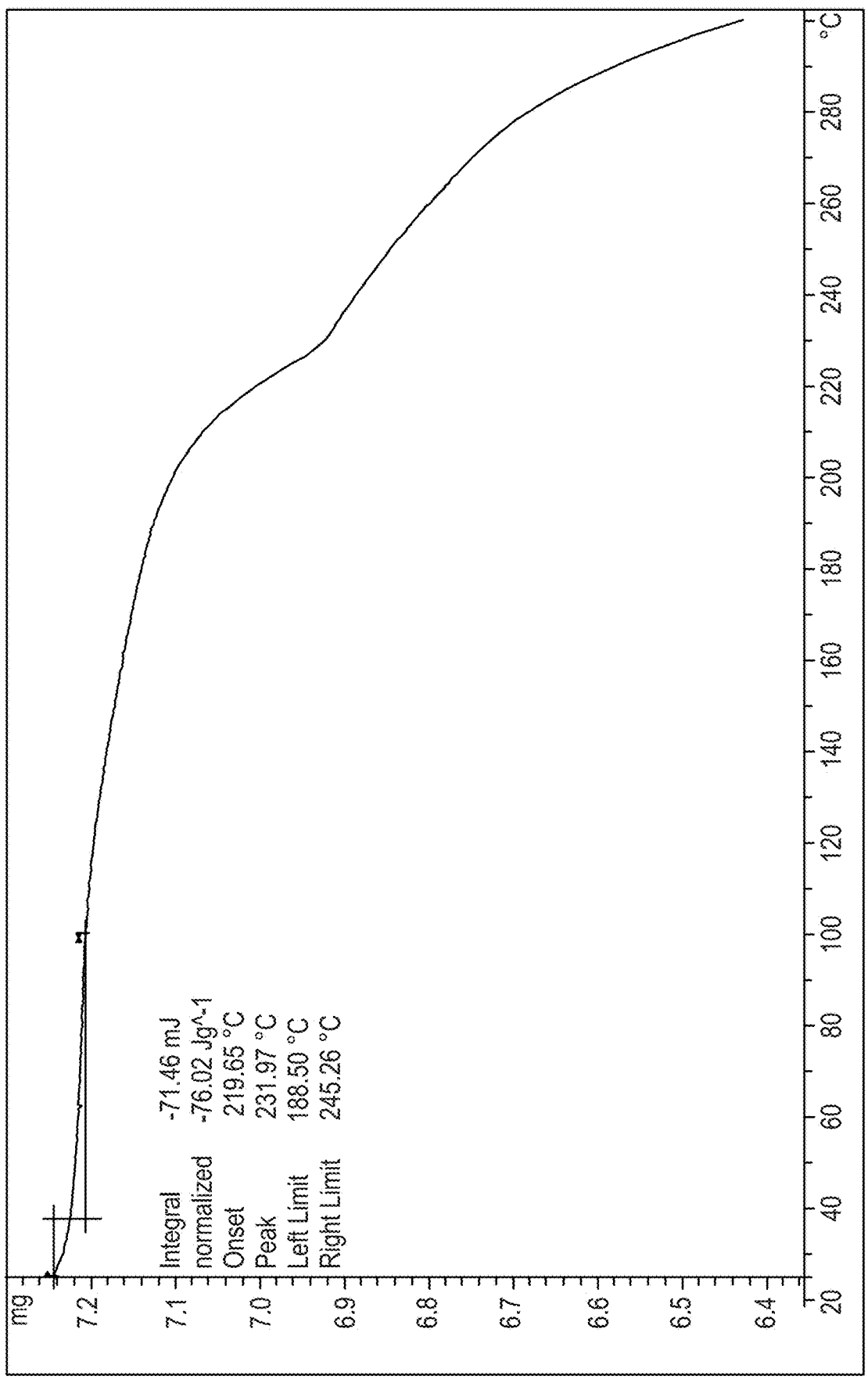
FIG. 6: TGA Thermogram of the HCl salt prepared according to Example 3.2

The isolated solid from the scale-up run was tested by DSC to evaluate the melting point and potential form changes. FIG. 5 shows a relatively broad melting range but does not indicate form changes. The melting onset is found at 220° C. and the main peak at 232° C. Thermogravimetry of the hydrochloric acid salt (FIG. 6) showed no clear step of solvent release. At the melting point onset (220° C.) a clear step is visible indicating decomposition or release of HCl during melting process.

Hygroscopicity (DVS)

Figure 7:
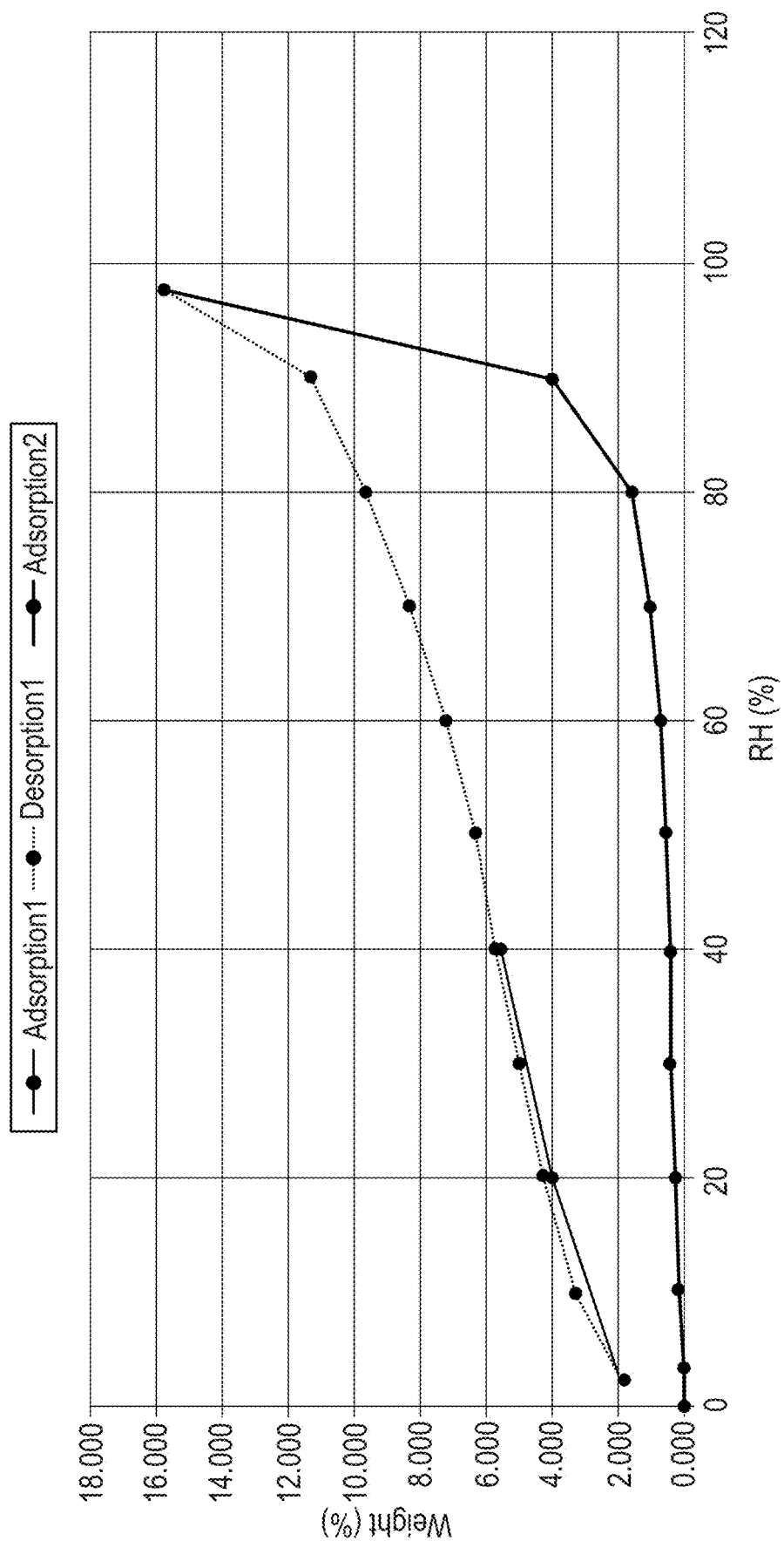
FIG. 7: DVS of the HCl salt prepared according to Example 3.2

The DVS (FIG. 7) shows the water adsorption increasing fast above 80% RH; desorption is much slower and does not finish within the measurement time. The bottom figure shows that the water uptake is not finished at maximum humidity (98% RH), and during decreasing humidity no equilibrium is reached. The starting second cycle takes up water much faster than during first cycle. With more than 16% w/w water uptake and no clear step, the hydrochloride is very hygroscopic.

Summary on the Varoglutamstat Hydrochloride Salt Obtained in Example 3.2

Taken together, the hydrochloride salt of Varoglutamstat obtained in Example 3.2 showed a higher solubility in water compared to the free base and other salt forms tested.

However, the salt formation in isopropanol with aqueous HCl tended to occur spontaneously with a sudden nucleation step and did not progress in an aspired continuous manner. It resulted in very thick suspensions and material comprising amorphous halos. Moreover, the material was deemed to be hygroscopic.

Example 4: Scale-Up Development for Varoglutamstat Hydrochloride

Example 4.1: Process Development for a Water-Free Preparation of Varoglutamstat Hydrochloride As a first step, a solubility screen of the hydrochloride salt (obtained from the 1 g scale experiments in Example 3.2) was performed in single solvents as listed in Table 5. This was done in order to identify the most suitable solvents for the process development.

Procedure of the Solubility Screen

A suspension of 50 mg/mL Varoglutamstat Hydrochloride in respective solvent was heated up at 0.2° C./min to reflux temperature and cooled at 0.5° C./min to 20° C. The resulting suspensions were equilibrated for at least 4 hours and the mother liquors sampled for solubility determination by HPLC (see "Description of analytical procedures used in the Examples of the invention" for method details).

TABLE 5

Solubility of the HCl salt in mg/mL calculated from the determination of the free base by HPLC in mother liquor. Any obtained solutions indicate solubility being identical or higher than 50 mg/mL as this was the maximum quantity of salt provided per sample.

| Solvent | Solution 20° C.? | ML free base (mg/ml) | calculated HCl (mg/mL) | aspect |
| --- | --- | --- | --- | --- |
| TBME | x | 0.0 | 0.0 | thick suspension |
| Acetone | x | 0.1 | 0.1 | thick suspension |
| THF | x | 0.0 | 0.0 | thick suspension |
| MeOH | ✓ | 47.5 | 52.6 | solution |
| EtOAc | x | 0.0 | 0.0 | thick suspension |
| EtOH | x | 41.3 | 45.8 | suspension |
| IPA | x | 3.6 | 4.0 | thick suspension |
| MEK | x | 0.0 | 0.0 | thick suspension |
| ACN | x | 0.1 | 0.1 | thick suspension |
| IPrOAC | x | 0.0 | 0.0 | thick suspension |
| nPrOH | x | 10.4 | 11.5 | thick suspension |
| Heptane | x | 0.0 | 0.0 | thick suspension |
| Water | (✓) | 52.0 | 57.6 | solution |
| Toluene | x | 0.1 | 0.1 | thick suspension |
| MIBK | x | 0.1 | 0.1 | thick suspension |
| DMSO | ✓ | 51.7 | 57.3 | solution |
| nBuOH | x | 3.9 | 4.4 | solidified |
| Me-THF | x | 0.0 | 0.0 | thick suspension |

The high solubility in water and alcohols made those obsolete for a single solvent salt formation process. The very low solubility of Varoglutamstat Hydrochloride in almost all other solvents led to spontaneous nucleation of the obtained crystals. This then resulted in unstirrable and poorly filterable suspensions with the need of a high dilution in order to get the suspensions stirrable again.

Figure 8:
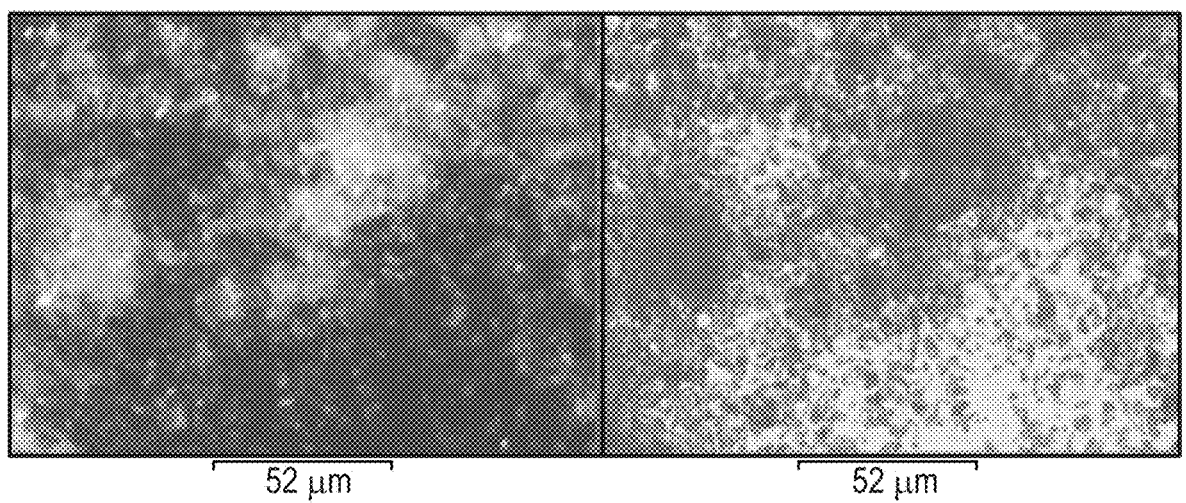
FIG. 8: Failed attempt for optimization of the HCl salt crystallization, crystal shape after "wet milling".

A first attempt to improve the handling of suspensions in isopropanol (see Example 3.2) was the application of intensive stirring. This approach failed as the original crystals were found to be completely destroyed and the obtained crystals to have round edges generated by attrition (FIG. 8, suspension after stirring for more than one week).

In yet another attempt, it was tried to run the process in DMSO with acetone as anti-solvent. Here, the suspension turned almost to a block after it was seeded. The first few drops of HCl in dioxane then resulted in formation of amorphous flakes rather than needles.

The salt formation in pure isopropanol with HCl in isopropanol was found to be hardly stirrable. The addition of HCl in isopropanol was extended to almost 12 hours, but still a spontaneous nucleation occurred towards the end of the addition.

Surprisingly, when the suspension was diluted with acetone, the resulting suspension seemed to crystallize in a more controlled manner. Based on this observation, acetone was added to the salt formation mixture right from the beginning. When doing so, the seeding seemed much more successful. Whereas the addition of solely HCl to the seeded mixture in isopropanol did not show a clean crystallization, the addition of acetone led to the change of this passivation of the seeds.

As the yield of salt formation was still low it was tried to start with a higher amount of acetone in isopropanol (60% v/v acetone)—but the mixture almost solidified. Starting with a 1/1 mixture of acetone and isopropanol followed by addition of acetone after the salt formation led to a more controlled crystallization.

Example 4.2: Detailed Description of the Preparation and Physical Characterization of the Varoglutamstat Hydrochloride Salt Obtained in Example 4.1

Procedure *:

The free base (1 wt, 1 eq, 5.08 g) is dissolved in a mixture of acetone (5 vol) and isopropanol (5 vol). The solution is heated to 40° C. A mixture of 5-6 N HCl in isopropanol (0.6 vol, ca. 1 eq) and isopropanol (2 vol) is prepared and half of the mixture is added. In the event that no nucleation occurs, the solution is seeded with Varoglutamstat Hydrochloride (0.014 wt; suspended in acetone/isopropanol 1/1 v/v; 0.4 vol). The overall suspension is equilibrated for at least 1.5 hours at 40° C. The remaining HCl in isopropanol solution is added continuously over 3 hours. The suspension is then cooled to 20° C. over 1 hour and then diluted with acetone (5 vol) over 2 hours. The suspension is then cooled for 2 hours to 0-5° C., equilibrated for 30 minutes and then filtered. The filter cake is washed with cold acetone/isopropanol 2/1 v/v (3 vol) and dried in vacuum (p<20 mbar, at T=45° C.).

The product obtained was a white solid with 89% yield (4.87 g).

*) the amounts are given relative to the weight of the free base used as starting material (Varoglutamstat free base), the total quantity of which is defined to represent 1 wt. The volumes are given in volumes (vol) based on the amount of free base, in which the gram amount free base utilized is multiplied by the vol factor to give the total quantity of mL to be used: 1 wt represents x g free base, to which y vol of solvent shall be added, thus x*y mL shall be applied (e.g. when 2.5 g free base is 1 wt, then 5 vol of solvent are equal to 12.5 mL).

Results

Handling of Crystals

The procedure led to well filterable material.

Figure 9:
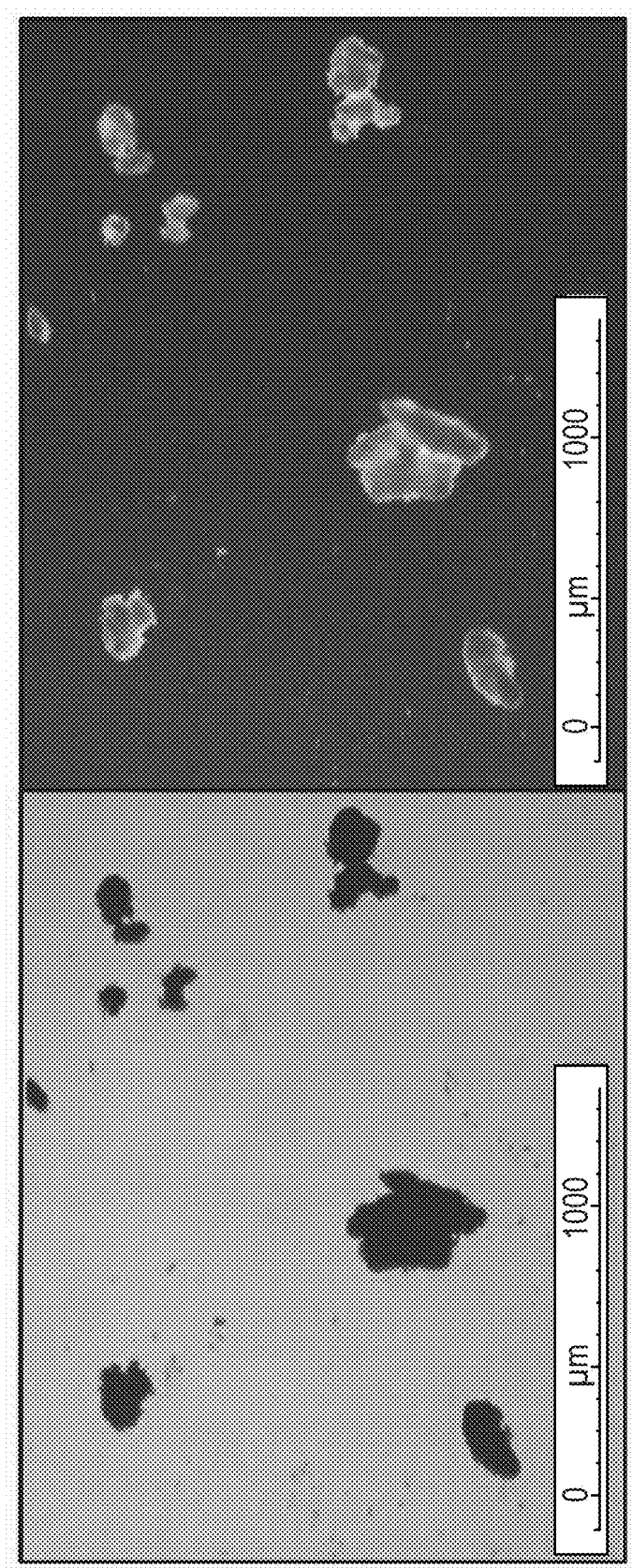
FIG. 9: Optical microscopy of the HCl salt prepared according to Example 4.2.

Crystallinity (Crystal Habit, Macroscopic and Microscopy, See FIG. 9)

The HCl salt prepared according to Example 4.2 was found to be crystalline and made of aggregates of very small crystals.

Figure 10:
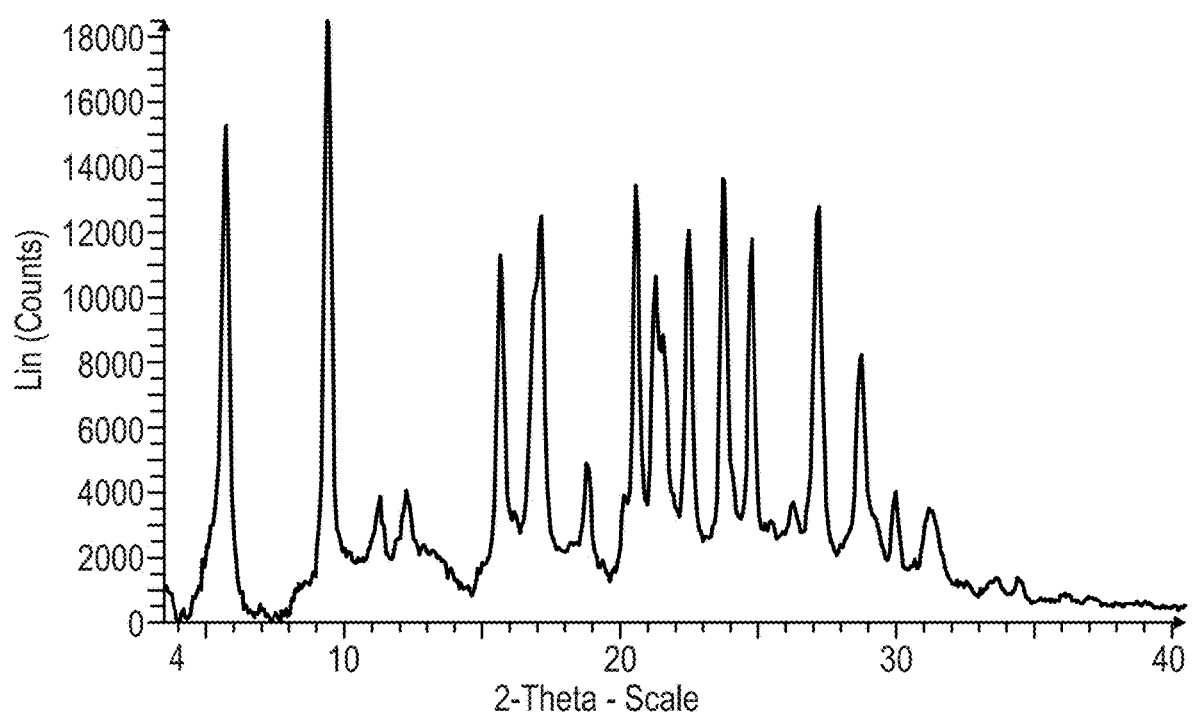
FIG. 10: XRPD of the HCl salt prepared according to Example 4.2.

Crystallinity (Quality of Crystals, XRPD, FIG. 10)

The HCl salt prepared according to Example 4.2 was found to be crystalline, still with a detectable amount of amorphous material as shown by the presence of the typical halo. The XRPD is discussed in detail in Example 5.1 below.

Figure 11:
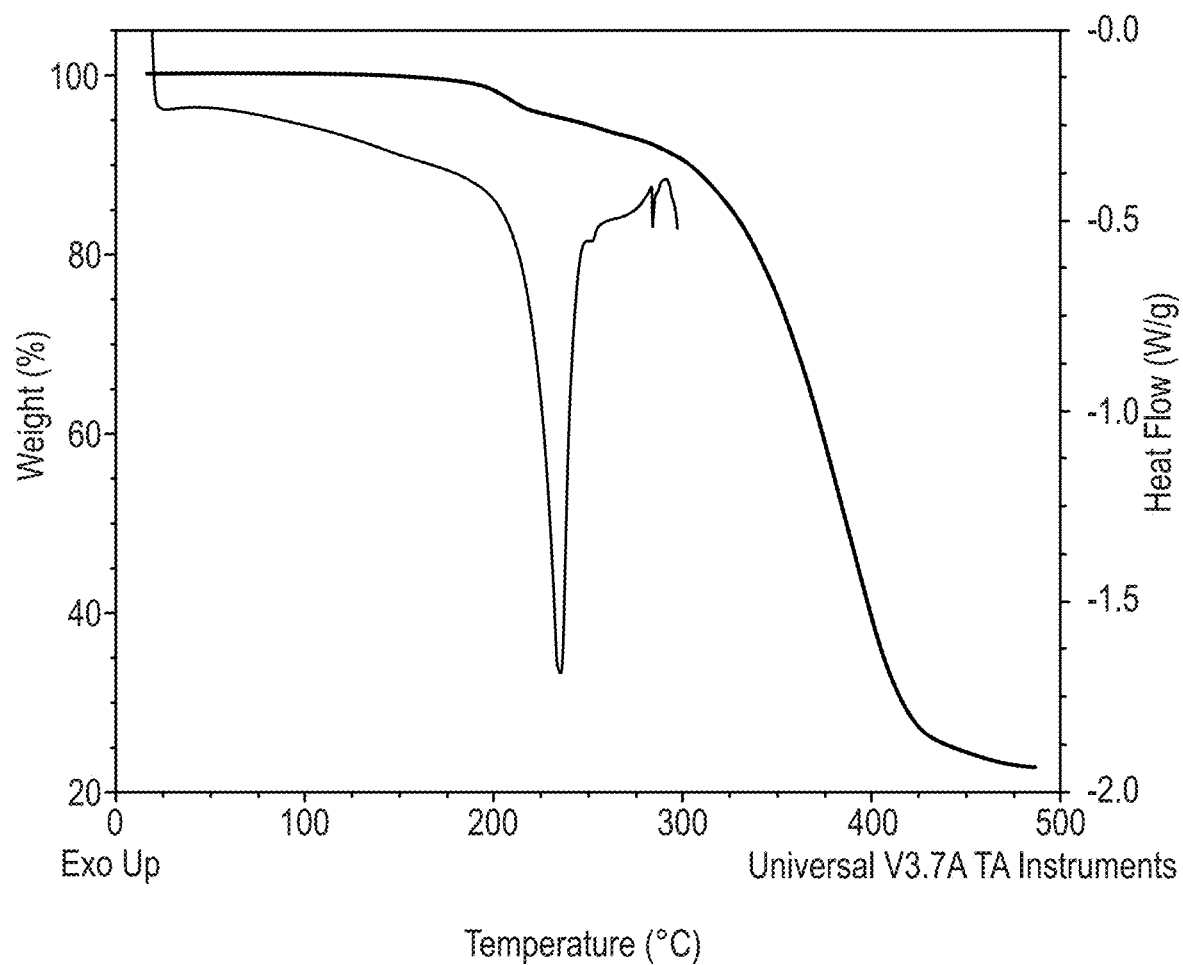
FIG. 11: Overlaid thermograms from TGA and DSC analyses of the HCl salt prepared according to Example 4.2.
Figure 13:
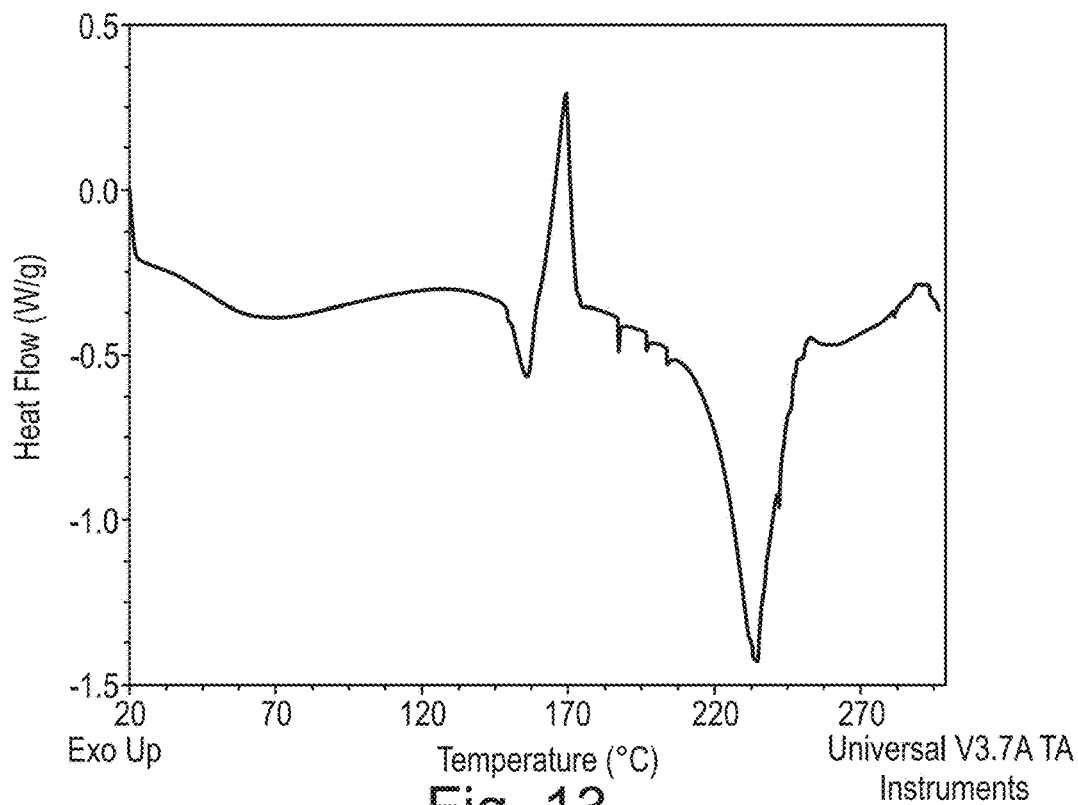
FIG. 13: DSC thermogram of the HCl salt prepared according to Example 4.2 salt, after DVS
Figure 14:
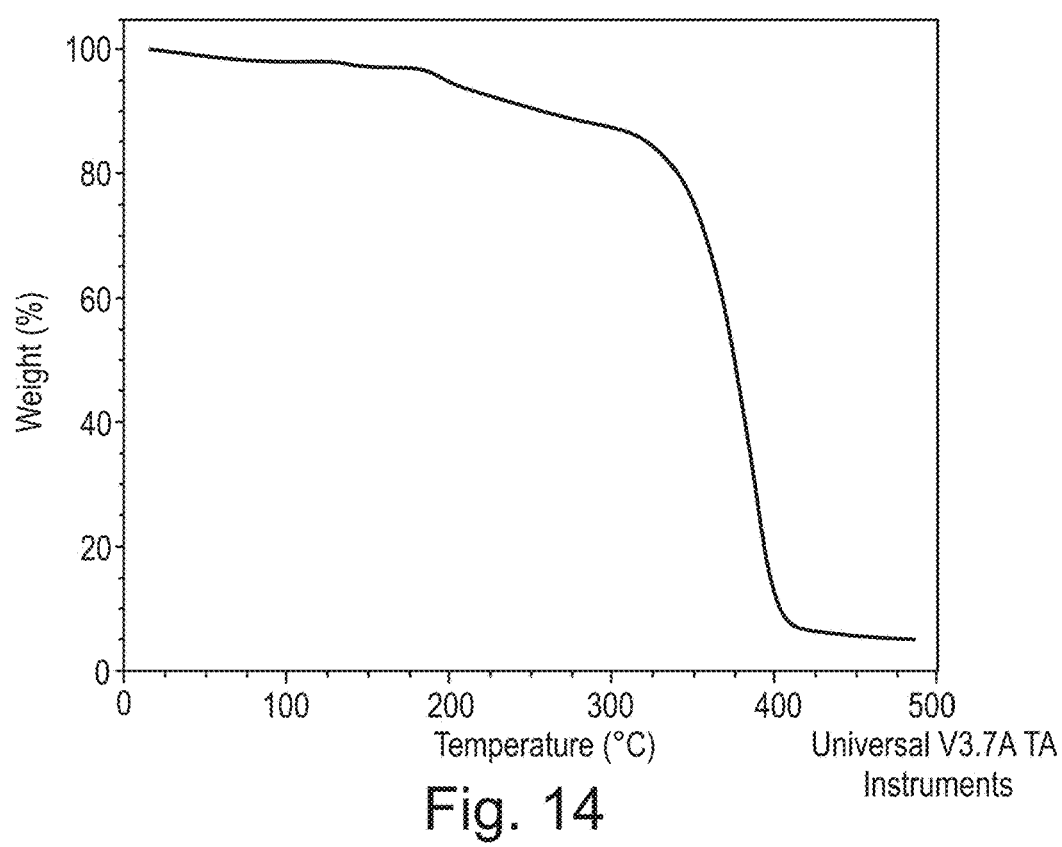
FIG. 14: TGA profile of the HCl salt prepared according to Example 4.2 salt, after DVS
Figure 15:
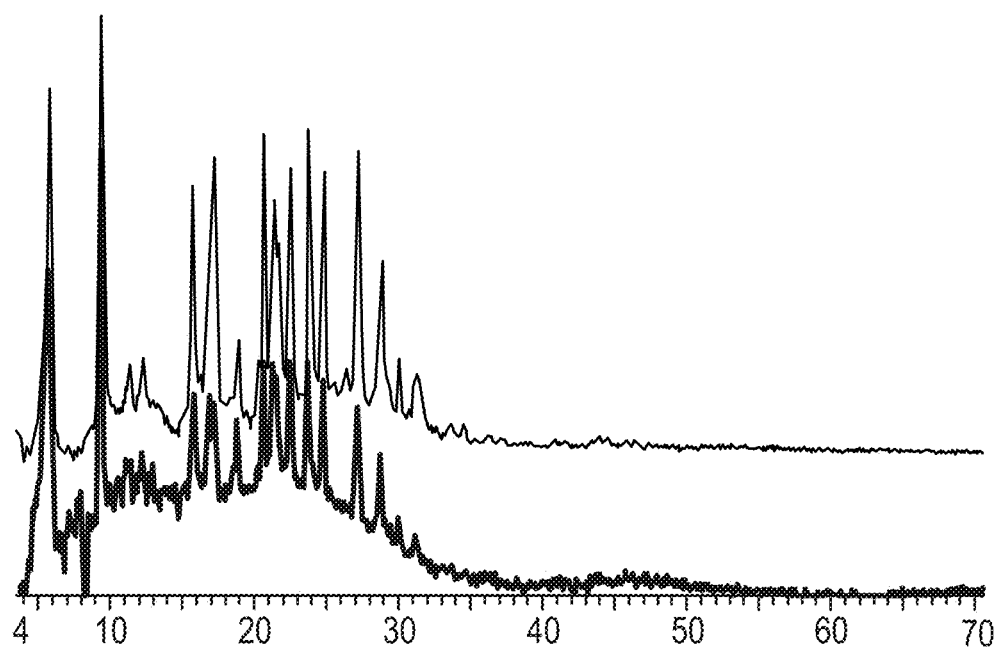
FIG. 15: Stacked X-ray diffraction patterns of the HCl salt prepared according to Example 4.2 salt before (black upper trace) and after (blue lower trace) DVS

Thermal Analysis (see FIG. 11 and FIG. 13)

The DSC analysis showed a broad endotherm with an onset at 221° C., indicating the onset of melting of the HCl salt with the main melting peak temperature at 235° C. The TGA showed two mass losses upon heating, a first loss of mass of 0.2% detected with onset/endset temperatures of 111/118° C. and a second loss of mass of 4.3% detected with onset/endset temperatures of 194/216° C.

These mass losses could be interpreted as adsorbed water desorption and structural water departure when the bulk melts (DSC melting temperature onset at 222° C. and TGA mass loss onset for the 4.3% mass loss at 194/196° C.).

The DSC of the material after performing the DVS, shows an additional melting at 150° C. and a an exotherm at 170° C. (onset and then changes into a form, melting at higher temperature. The melting point at the high temperature is then similar to the melting of Varoglutamstat Hydrochloride, prepared according to Example 4.1 and not exposed to elevated hygroscopicity. In addition, the TGA shows an additional mass loss of 4.5% at 185° C. (onset)

Figure 12:
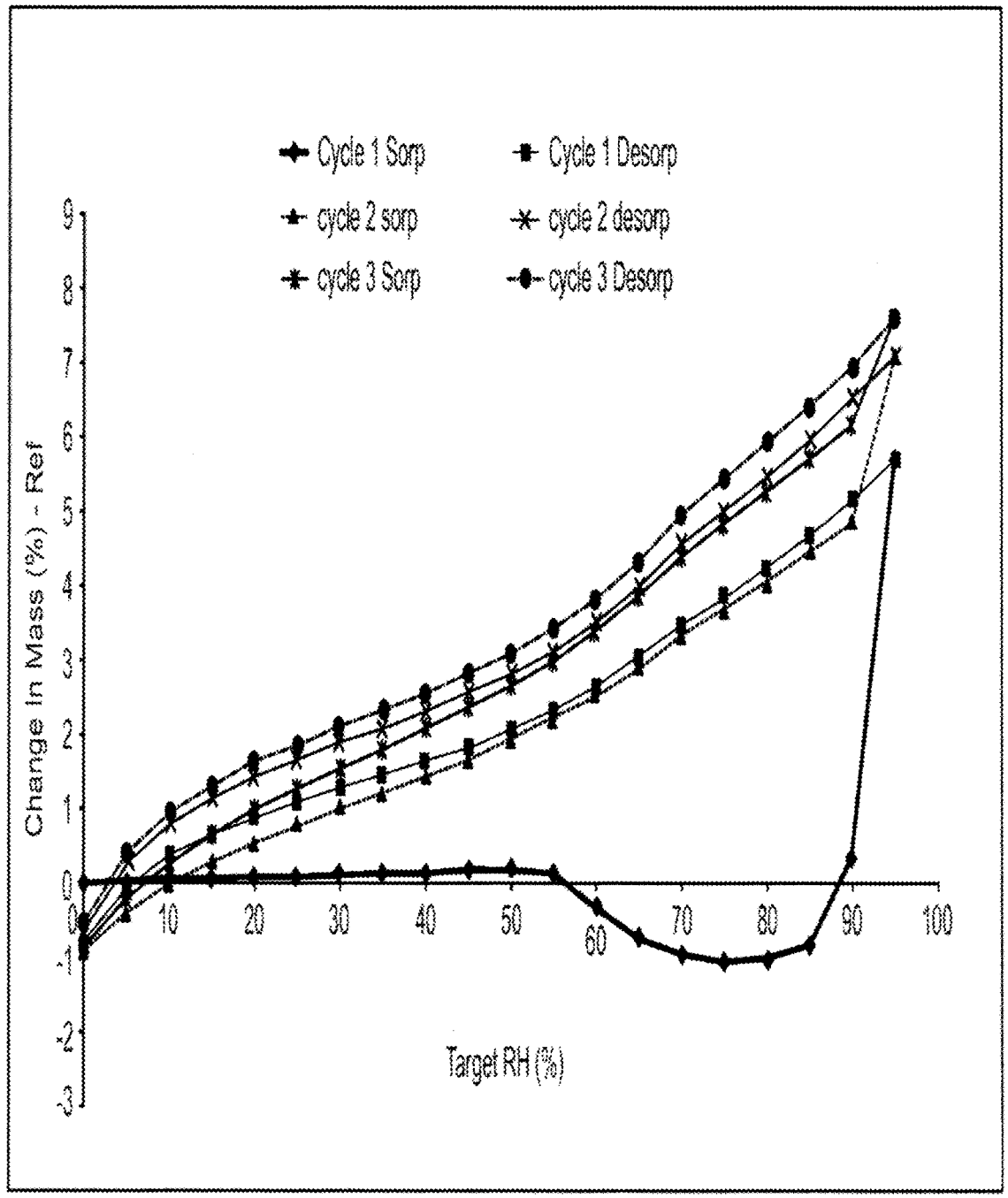
FIG. 12: DVS sorption and desorption cycles at 25° C. on the HCl salt prepared according to Example 4.2.

Hygroscopicity (DVS) (FIG. 12)

The material showed no particular mass loss at drying at 0% RH and no hygroscopicity (no significant mass change) up to 55% RH. After this the bulk was losing mass before starting to gain mass again which led to a 5-6% final mass gain at 95% RH (water sorption) compared to the initial mass. The material therefore demonstrated affinity to water uptake and can be regarded as being hygroscopic.

From the product obtained in the final process, further analytical data were collected.

Figure 16:
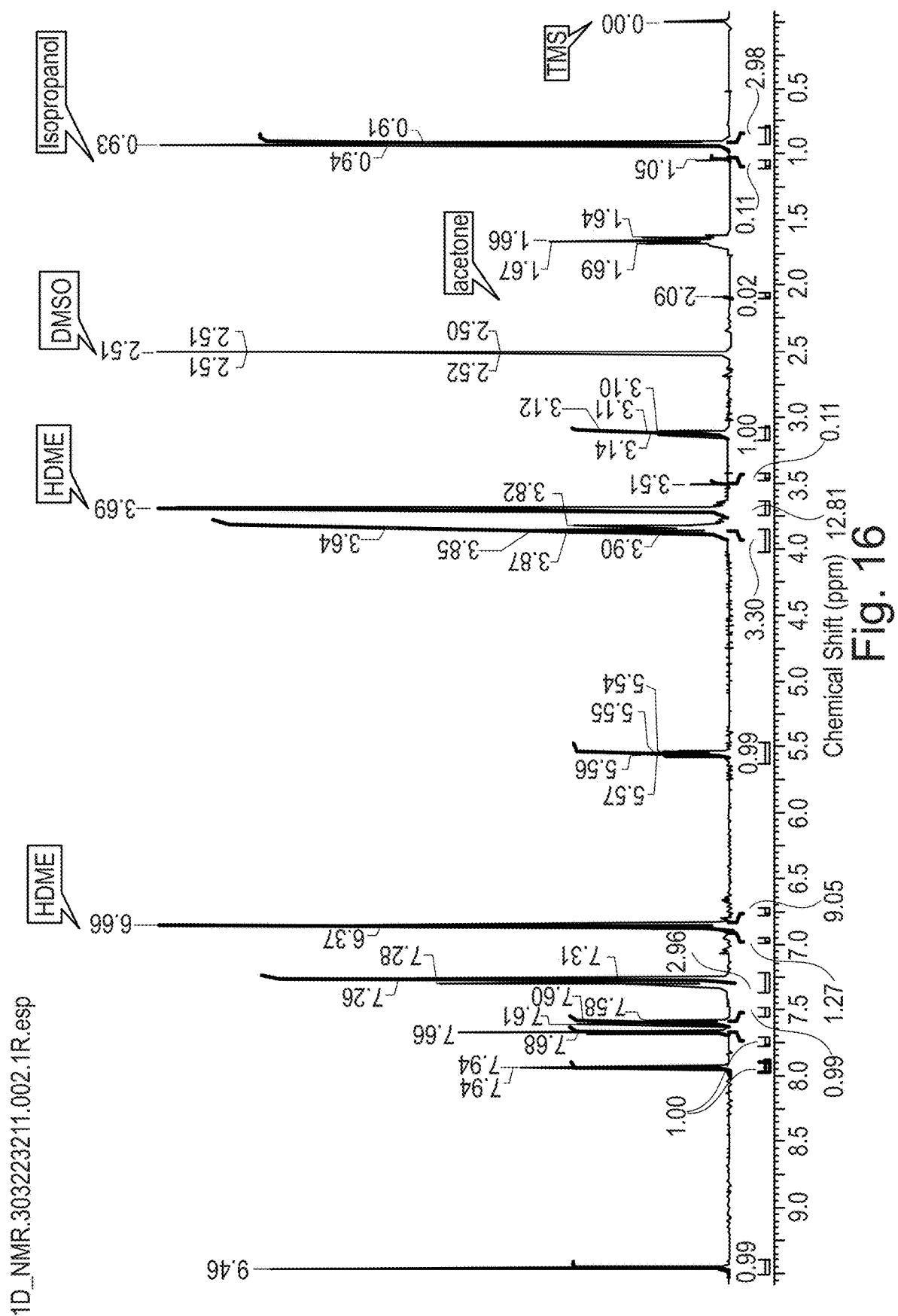
FIG. 16: NMR spectrum of the HCl salt prepared according to Example 4.2 (recorded in DMSO-d6).
Figure 17:
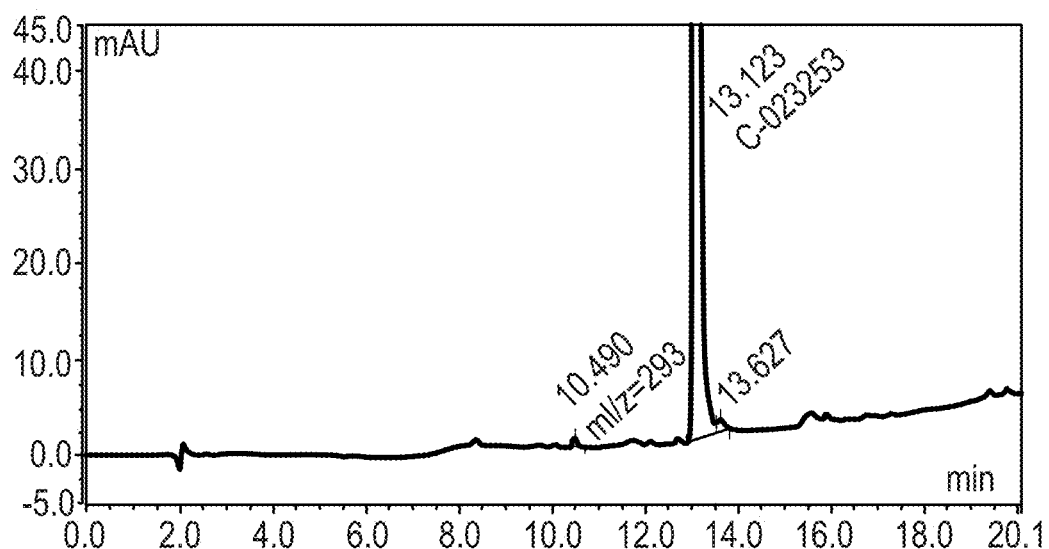
FIG. 17: HPLC chromatogram of the HCl salt prepared according to Example 4.2.

The Karl-Fisher titration indicated 0.16% w/w water (see "Description of analytical procedures used in the Examples of the invention" for method details). Residual acetone was determined by NMR (FIG. 16) to be 0.05% w/w and residual isopropanol at 0.29% w/w. HPLC analysis showed an overall purity of 99.82% a/a (FIG. 17). Residual isopropylchloride was determined by HSGC (Headspace Gas Chromatograph method). Isopropylchloride was usually present in the range between 4 ppm and 8 ppm.

Summary of Examples 4.1 and 4.2

Salt Formation of the HCl Salt

Crystal growth upon seeding seems to stall when not the correct solvents are used. The salt formation in pure isopropanol led to spontaneous nucleation even though the HCl addition was done very slowly. The addition of acetone reduced this effect drastically.

Crystallinity (Quality of Crystals, XRPD)

The material is crystalline, still with a detectable amount of amorphous material as shown by the presence of the typical halo.

Hygroscopicity

However, the obtained material is still deemed to be hygroscopic and may even be present as solvate or hydrate.

Genotoxic Impurities

The material contained trace amounts of isopropylchloride.

Example 4.3: Further Optimization of Varoglutamstat Hydrochloride Formation

Crystallinity and polymorphic purity (presence of the amorphous halo in the XRPD profile) and hygroscopicity of the product of Examples 4.1 and 4.2 were not satisfactory yet. Moreover, the process was still found not to be robust in terms of leading to crystalline solids in all cases. In addition, the product was prone to contain isopropyl chloride, a genotoxic impurity, resulting from the application of 5-6 N aq. HCl in isopropanol as in Example 4.2.

Further investigations into the salt formation conditions were performed using aqueous conditions and the antisolvents 2-butanone (MEK) and acetone. Acetone was already successfully applied in Example 4.2. Both are water-miscible, stable under strong acidic conditions at ambient temperature (mixtures with aqueous HCl) and non-solvents for Varoglutamstat Hydrochloride (see Table 5). A MEK protocol delivered a feasible procedure but the observed strong crust formation was anticipated to turn out to be an issue on process scale-up. Thus, the use of acetone was further pursued.

Initial Experiment Using the Aceton/Water System

It was surprisingly found that an acetone/water system with a low water content led to the formation of crystalline material.

Procedure *: 2 g (1 wt) of the Varoglutamstat free base were dissolved in acetone (6 vol), Varoglutamstat Hydrochloride seeds (150 mg) were added in two portions until a sustainable suspension occurred. The dosage of 1.0 eq HCl aq 32% in acetone (6 vol) was started at 20° C. Formation of a turbid mixture was observed, the temperature was elevated to 60° C. (weak reflux) and the dosage of HCl/acetone was continued. A white suspension was formed that solidified after completed addition of HCl/acetone. Acetone (9 vol) was added portion-wise and the resulting very thick suspension was cooled to ambient temperature within 30 min. After filtration and drying 2.04 g/92% were obtained as an off-white solid that showed crystalline habitus (microscope, agglutinated needles).

*) for a definition of "wt" and "vol", cf. Example 4.2.

Results

Even though the product was obtained in good yield, this protocol was deemed unfeasible for further investigations due to solidification after completed HCl addition.

Development of the Final Process

It was investigated in how far the above observed solidification could be avoided by addition of water after the dosage of 1.0 eq of HCl (32% w/w, 8% in acetone), into the solution of the Varoglutamstat in acetone (8 vol), followed by additional dosage of the non-solvent acetone to complete the crystallization. As a result, the addition of water ensured miscibility in the first place, however, resulting in the isolated material turning out not being crystalline.

In a following attempt the aim was to maintain a solution until complete dosage of HCl, followed by a controlled nucleation and crystallization by adding water and to identify the best process point for seeding (avoidance of the super saturation being too high). The latter was done by controlling the internal temperature, and addition of seeds before or during dosage of acetone, while the amounts of solvents acetone and water were unchanged with a ratio of acetone/water 48:1.6. This changed process control by super-saturation followed by cooling, seeding and addition of non-solvent acetone was successful regarding the miscibility at any time, controlled nucleation and crystal growth and delivered an acceptable and reproducible yield (>65% in most cases). Furthermore, the process reproducibly generated the polymorphs identified in Examples 3.3 and 4.2.

At this time the process delivered an unknown impurity within the isolated Varoglutamstat Hydrochloride in amounts of 0.3-0.4% a/a (according to HPLC). Assuming that the presence of the impurity could have resulted from a chemical conversion out of the impurity profile of the free base of Varoglutamstat, the process was further adapted with the goal to apply milder conditions during the salt formation to avoid potential byproduct formation and thus to achieve highest purity of product during crystallization and workup with optimal yield. This was accomplished by:

Addition of HCl/acetone at 45±5° C. instead of reflux (around 55° C.).

Use of less HCl, i.e. 0.9 eq instead of 1 eq (corresponding to 1.0 eq of substrate, assay corrected).

Final crystallization temperature and filtration to be 20° C. instead of 0° C.

1 st rinse of the suction filter with acetone/water instead of pure acetone.

The combination of these changed parameters resulted in a reproducible process showing a reduction of impurity content down to traces near the limit of detection.

Further investigations were undertaken regarding the robustness of the process. The following criteria have been investigated:

Equivalents of HCl used for the salt formation,
Time point of seeding, super saturation,
Ripening after seeding,
Mixture ratio acetone/water,
Total volume of acetone/water mixture,
Dosage of the non-solvent acetone: amount, dosage time and yield,
Final stirring time before filtration,
Final crystallization and filtration temperature,
Regime of the suction filter rinse,
Use of different purity grades of Varoglutamstat free base (assay controlled).

The investigations resulted as follows:

Use of 0.95 eq of HCl (32% w/w) in acetone were found optimal regarding the purity.

Addition of a suspension of seeds in acetone directly after completed dosage of HCl/acetone.

A ripening period of at least 30 min before the dosage of the anti-solvent acetone is started.

The optimal amount of additional water was found to be 221 mg/mmol$_{free\ base}$ in a setting of acetone (8 vol) and 0.95 eq of HCl (aqueous 32% w/w) procedure.

The use of 16 vol of acetone to complete the crystallization.

The final crystallization temperature is to be set 20° C. and the optimal final stirring time is 1 h.

The optimal suction filter regime consists of a 3-fold rinse: 1st rinse with acetone/water mixture in the mixture ratio of the solvent used for the salt formation followed by two rinses with pure acetone.

After checking three different grades of free base containing typical production related impurities (e.g. HCl consuming organic bases) the exact determination of the total water content as well as the determination of the total HCl consumption and the assay of the free base PQ912 was identified to be important to ensure a controlled nucleation.

Final Procedure*

To 88.00 g of a solution of Varoglutamstat free base (1.0 eq, 17.79 g, 1 wt, 52.8 mmol) in 5 vol acetone (89 mL acetone containing 0.77 g of water) resulting in a free base mass percentage of w=0.202, 7.02 g of water were added **. The mixture was heated to 45±5° C. While heating, after 18 min and a reached temperature of 40° C., the dosage of 3.3 vol of HCl in acetone (0.95 eq, 32% w/w 5.73 g in 53 mL acetone) was started while heating with 45±5° C. was continued. When the dosage was completed after 39 min, the pH was checked to be found pH=4. Seed suspensions (Varoglutamstat Hydrochloride 36 mg in acetone) were added at 45±5° C. This resulted in an immediate start of nucleation and the start of the ripening period. Check by microscopy after 19 min (45±5° C.) revealed the presence of needles in a well miscible suspension and the continuation of the ripening. An additional amount of 285 mL (16 vol) of acetone were added over 56 min and cooling was started at 45 +5° C. When 22° C. was reached after cooling of 40 min, the mixture was stirred over 60 min at 20° C. After finishing of the stirring for 110 min, the suspension was filtered (G3 glass suction filter). The material was found to be easily filterable; no application of vacuum was needed. After this, the remaining solid was rinsed with 71 mL (4 vol) of a mixture of acetone/water (48:1.4; v/v) followed by a two times rinse with acetone (53 mL, 3 vol). The remaining solid was dried on the suction filter for 80 min, followed by drying at T 50° C., p<20 mbar. The drying was finished at p<11 mbar. The remaining solid was found to be a free flowing solid.

*) for a definition of "wt" and "vol", cf. Example 4.2.

**) The total amount of water in the final reaction must be equal to 221 mg per mmol Varoglutamstat free base. It results from the water content in the starting acetone solution (determined by KF), the water content (assay) of the aqueous HCl solution and the difference to be added to reach a content of 221 mg per mmol Varoglutamstat Free Base.

Results

Handling of Crystals

The procedure led to well filterable material, free flowing solid after drying.

Figure 18:
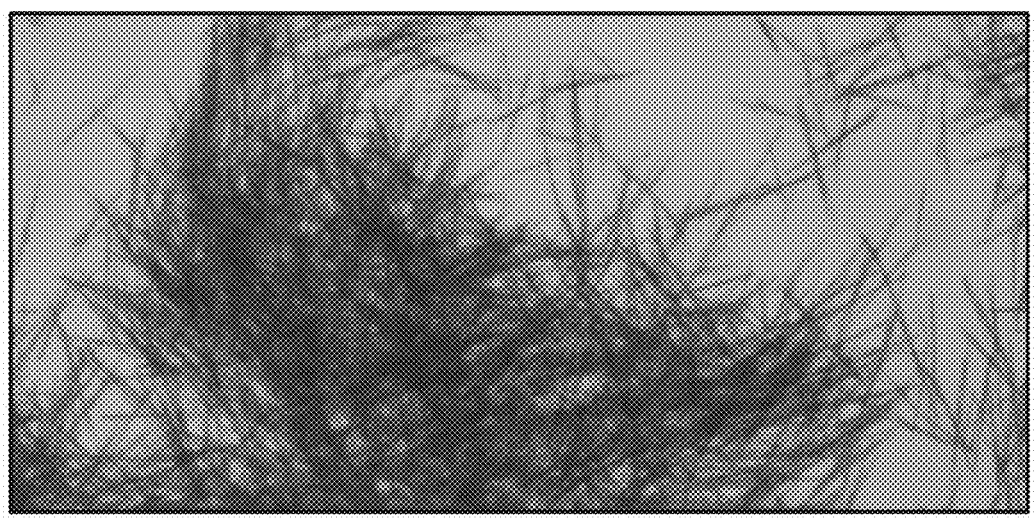
FIG. 18: Microscopy photo of the HCl salt prepared according to Example 4.3, magnification x20.

Crystallinity (Crystal Habit, Macroscopic and Microscopy) (FIG. 18)

The obtained Varoglutamstat Hydrochloride crystals showed a needle-like structure.

Figure 19:
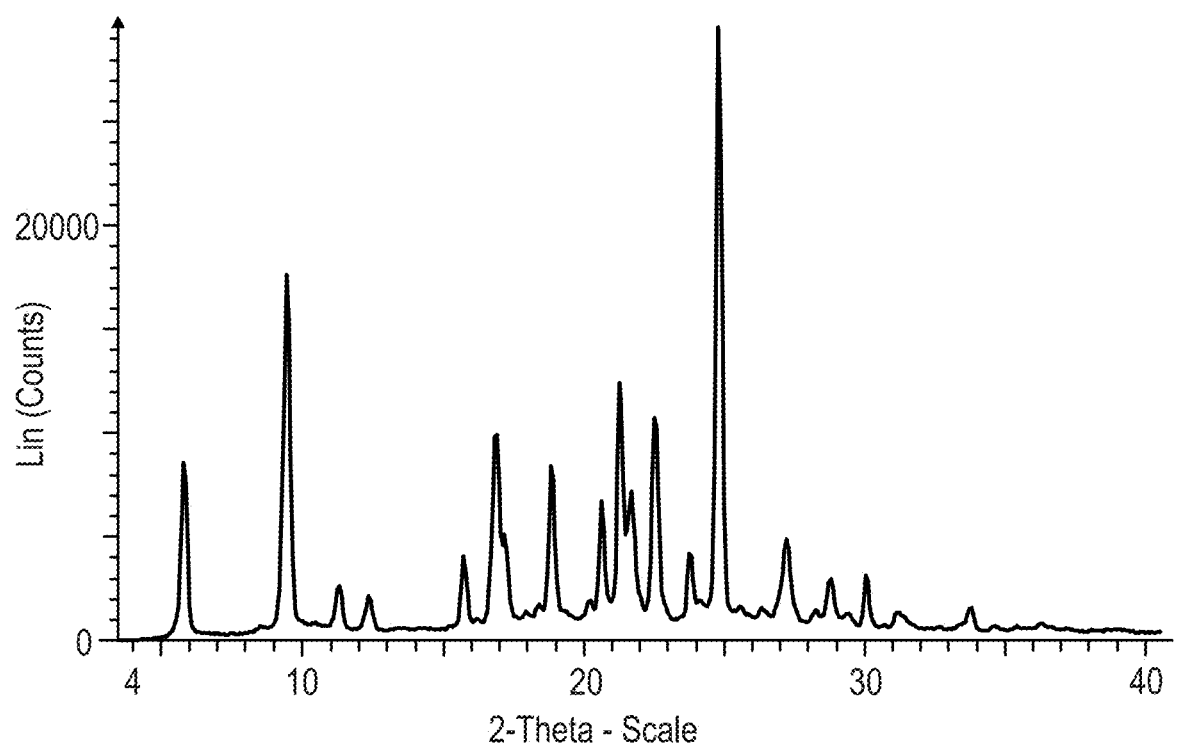
FIG. 19: XRPD of the HCl salt prepared according to Example 4.3.

Crystallinity (Quality of Crystals, XRPD, See FIG. 19)

The material was found crystalline with a strongly reduced amorphous halo content, which was clearly present in the material obtained in all previous experiments. The XRPD pattern is discussed in Example 5.3 below. The process in example 4.3 delivered material of improved crystallinity. This is demonstrated in FIGS. 28 and 29, which are showing y-normalized overlays of the XRPD profiles of Varoglutamstat HCl from examples 4.2 and 4.3. They demonstrate a clear reduction of the amorphous halo for the material produced in example 4.3.

Figure 20:
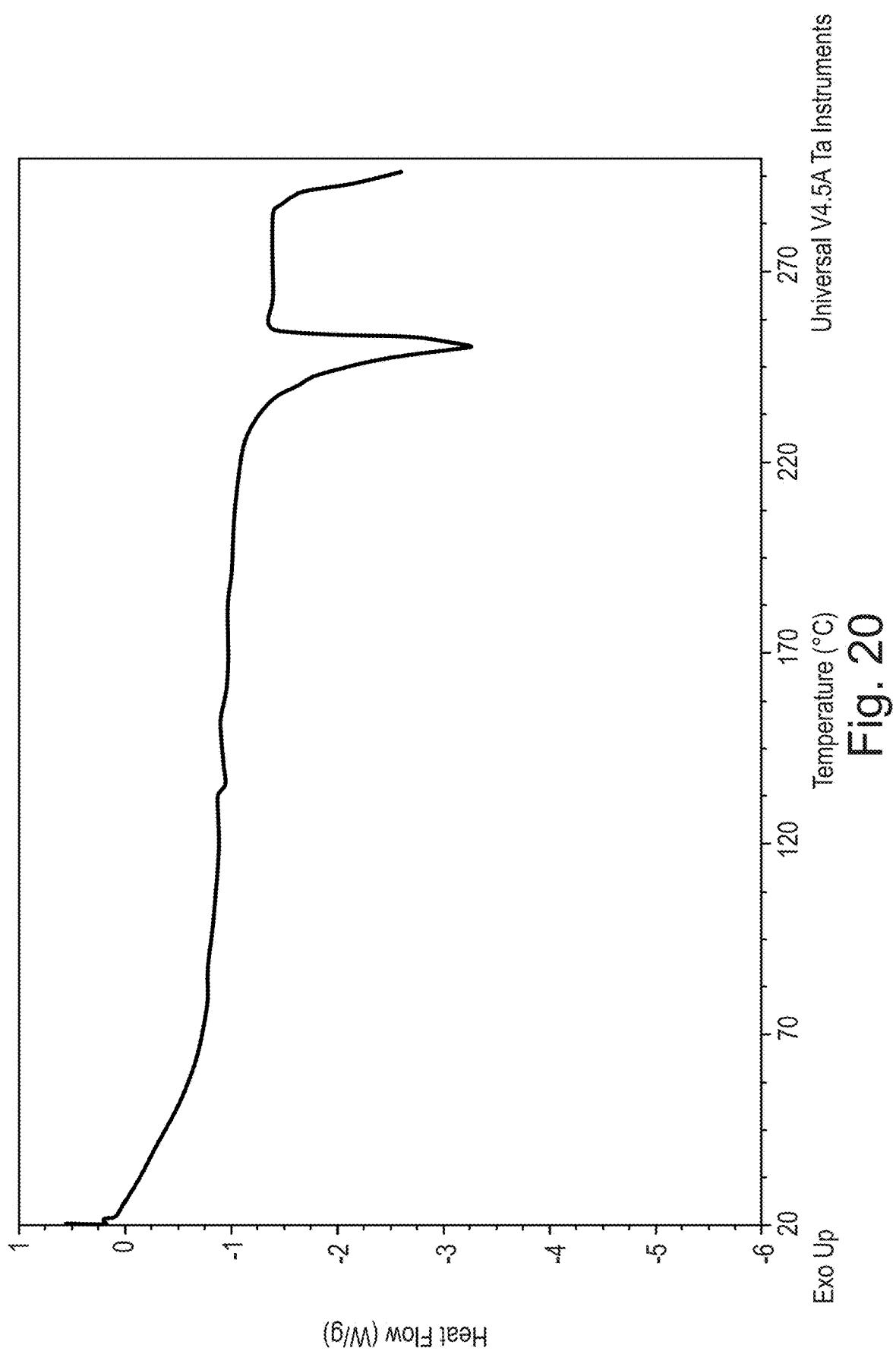
FIG. 20: DSC analysis of the HCl salt prepared according to Example 4.3.
Figure 21:
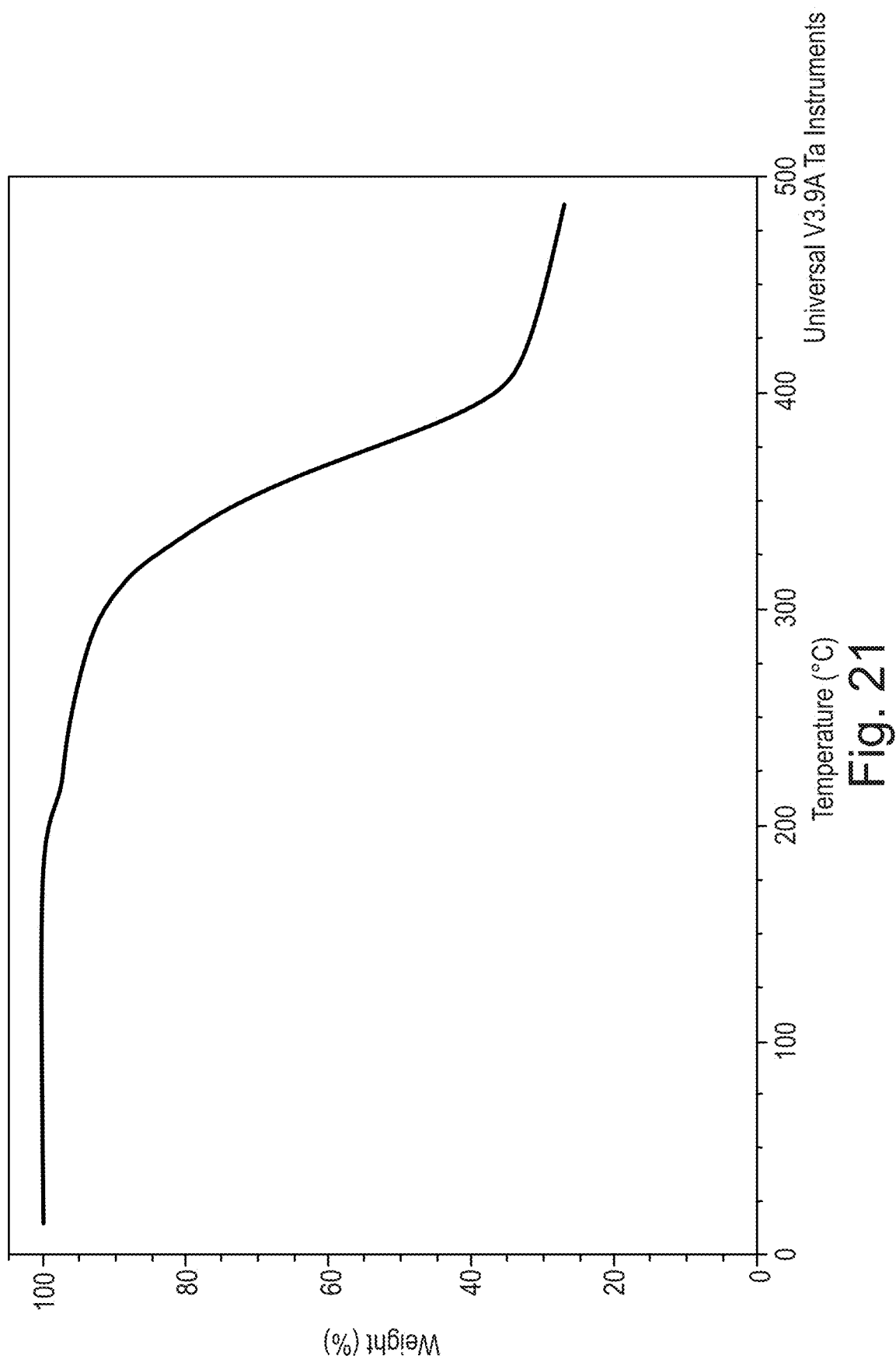
FIG. 21: TGA analysis of the HCl salt prepared according to Example 4.3.

Thermal Analysis (See FIG. 20 and FIG. 21)

The DSC analysis showed a melting onset at 243° C. and the main melting peak at 251° C.

Upon heating, the TGA analysis showed one mass loss of 3.0% with onset/endset temperatures of 190/215° C. prior to the main thermal decomposition of the compound (with an onset temperature of 326° C.).

Figure 22:
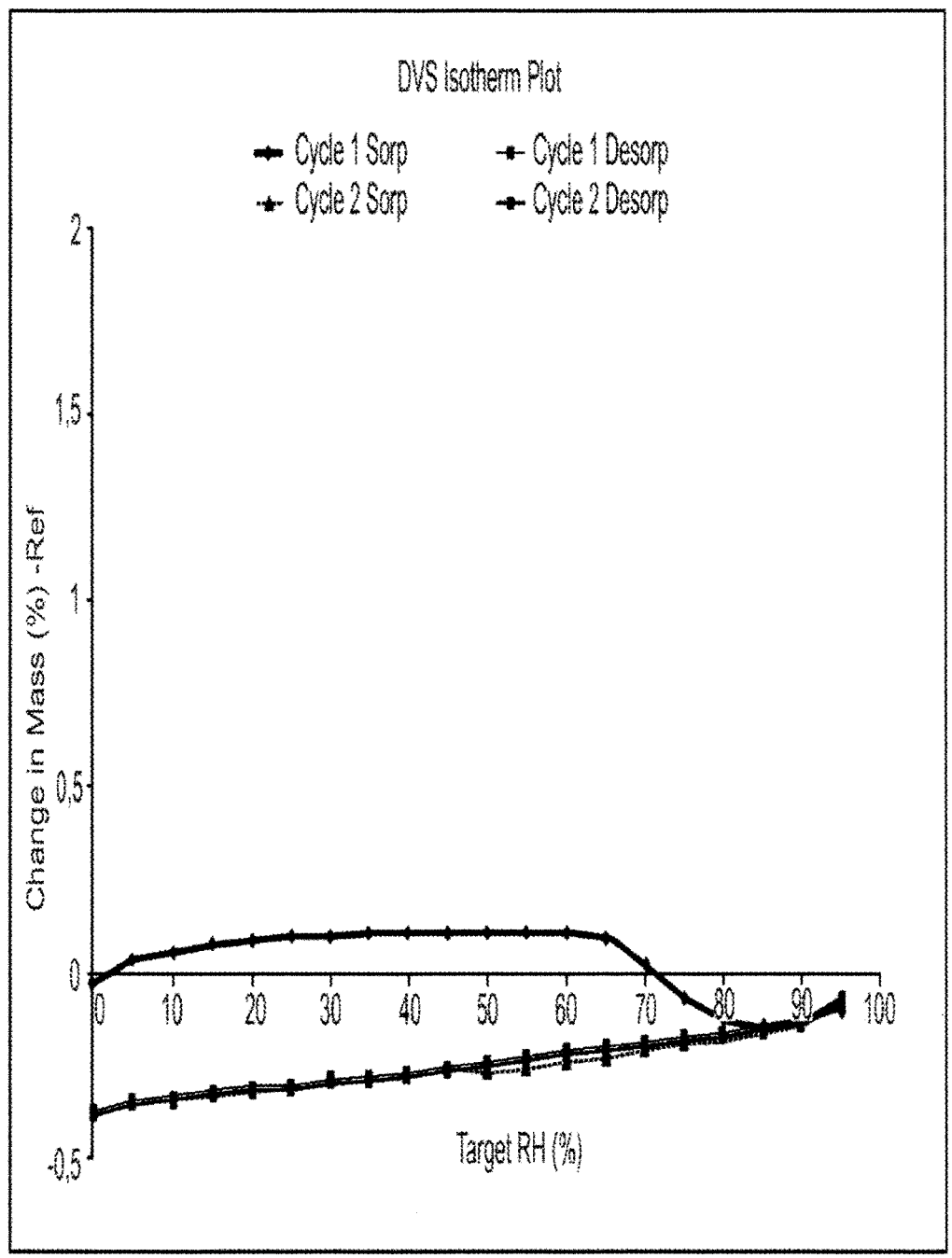
FIG. 22: DVS analysis of the HCl salt prepared according to Example 4.3.

Hygroscopicity (DVS, FIG. 22)

In contrast to Example 3.3 (FIG. 7) and Example 4.2 (FIG. 12), the material showed no particular mass loss up to 70% RH. Moreover, over 70% RH the bulk was losing mass, which was never gained back in the following sorption/desorption cycles. All in all this is indicating the material not to be hygroscopic.

From the product obtained in the final process, further analytical data were collected.

Figure 23:
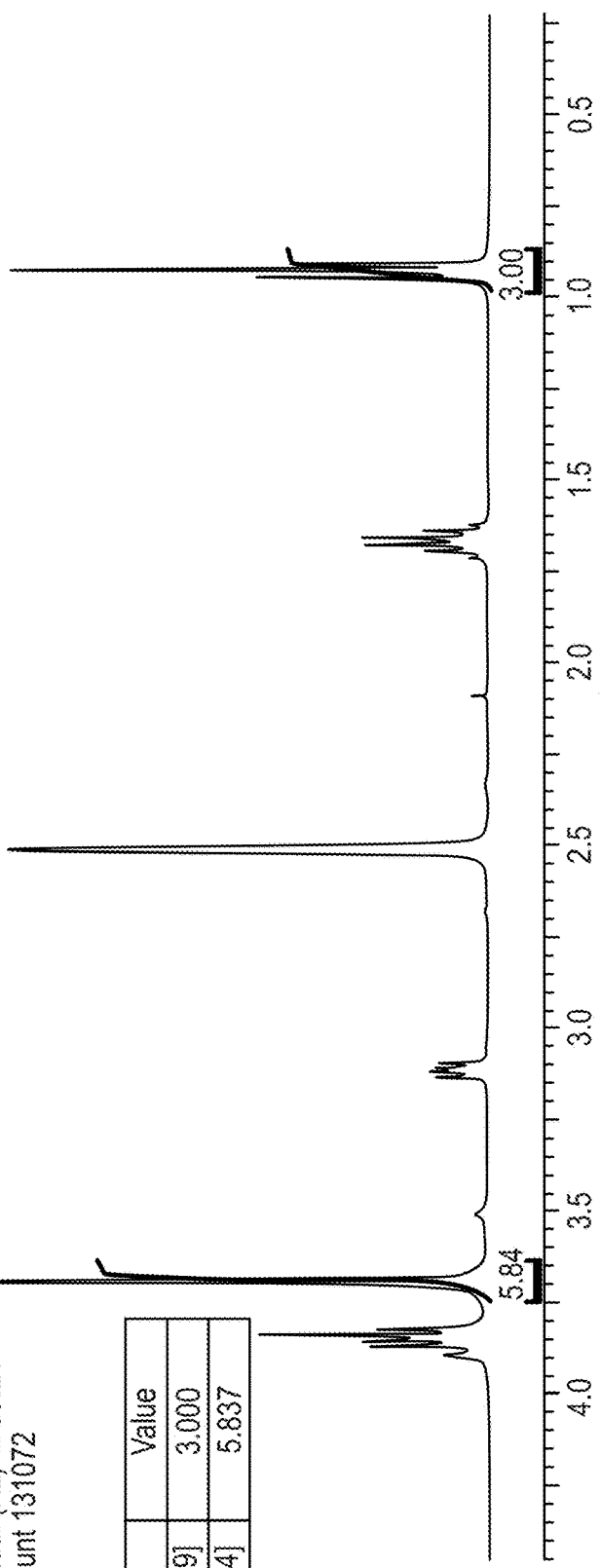
FIG. 23: NMR spectrum to determine the assay of the HCl salt prepared according to Example 4.3 (recorded in DMSO-d6).
Figure 24:
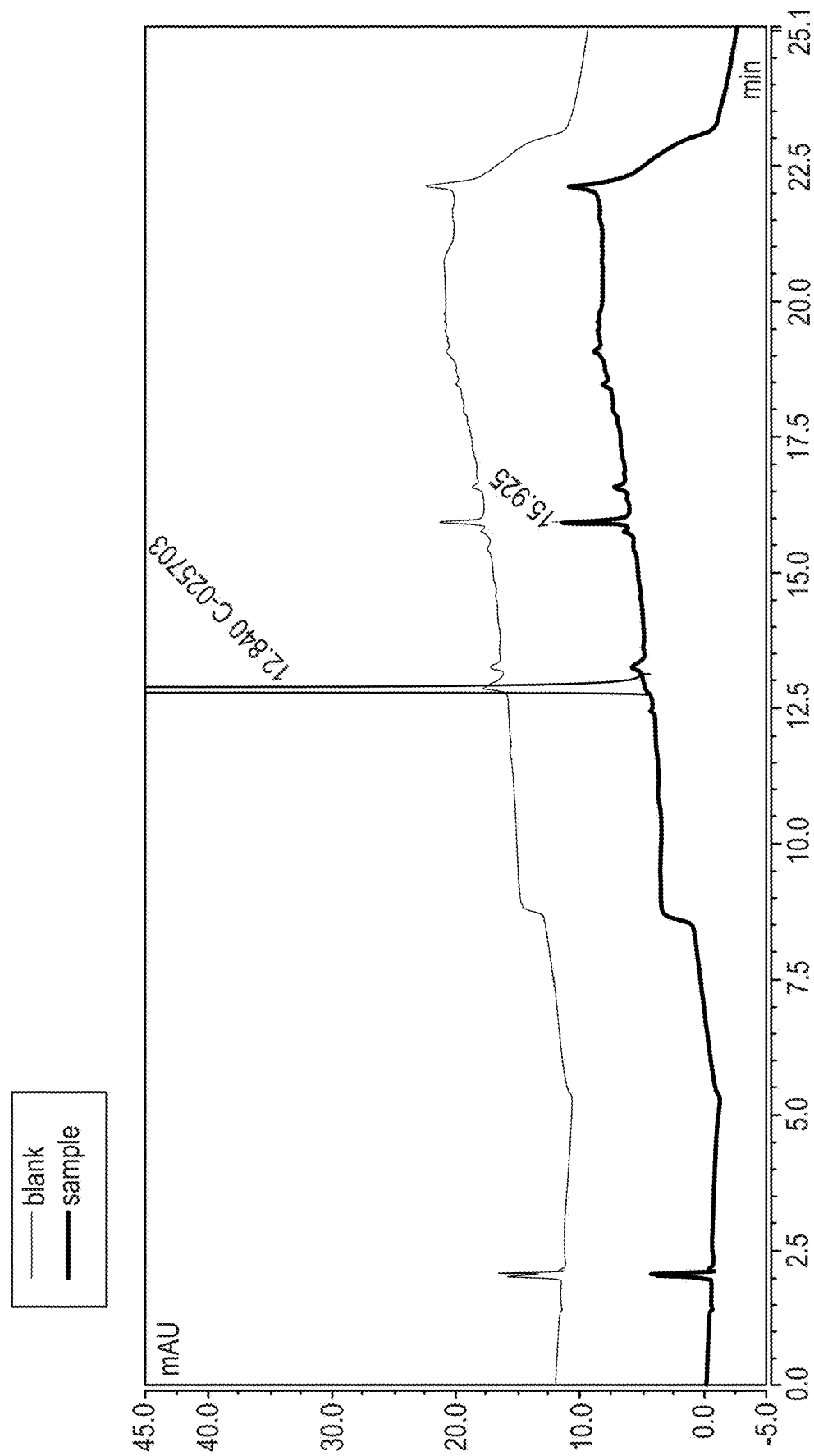
FIG. 24: HPLC Chromatogram of the HCl salt prepared according to Example 4.3.

The assay was found to be 94.66% w/w, the result of which was confirmed by NMR (FIG. 23). The material had an achiral purity of 99.88% a/a (see FIG. 24). The material was free of genotoxic isopropylchloride as determined by HSGC (Headspace Gas Chromatograph method).

Example 5: Investigations into the Polymorphism of the HCl-Salt

Example 5.1: XRPD Profile of Varoglutamstat Hydrochloride Obtained in Example 3.2

From the material obtained out of the HCl salt scale-up experiment on 1 g scale an X-ray powder diffraction was performed. The salt formation tended to form a very thick suspension spontaneously after complete addition of the aqueous HCl. Amorphous material, at least in small amounts, was detected: small amorphous halos were detected in the otherwise quite crystalline HCl adduct. The XRPD profile is presented in FIG. 4.

Example 5.2: XRPD Profile of Varoglutamstat Hydrochloride Obtained in Examples 4.1 and 4.2

The XRPD profile is presented in FIG. 10.

Example 5.3: XRPD Profile of Varoglutamstat Hydrochloride Obtained in Example 4.3

The XRPD pattern of the Varoglutamstat Hydrochloride obtained in Example 4.3 is shown in FIG. 19 The following table shows Thêta (°) peaks of the XRPD pattern shown in FIG. 19.

TABLE 6

Thêta (°) of well-resolved peaks of the XRPD pattern shown in FIG. 19. The position of the Thêta (°) peaks in the table below my vary by ±0.2°.

| Angle 2-Theta ° | d value Angstrom | Intensity Count | Intensity % |
|---|---|---|---|
| 5.8 | 15.1 | 8578 | 29.0 |
| 9.5 | 9.3 | 17619 | 59.6 |
| 11.3 | 7.8 | 2600 | 8.8 |
| 12.4 | 7.1 | 2132 | 7.2 |
| 15.8 | 5.6 | 4073 | 13.8 |
| 16.9 | 5.3 | 9927 | 33.6 |
| 17.2 | 5.1 | 5289 | 17.9 |
| 18.9 | 4.7 | 8446 | 28.6 |
| 20.2 | 4.4 | 1914 | 6.5 |
| 20.7 | 4.3 | 6726 | 22.7 |
| 21.3 | 4.2 | 12404 | 41.9 |
| 21.7 | 4.1 | 7186 | 24.3 |
| 22.6 | 3.9 | 10754 | 36.4 |
| 23.8 | 3.7 | 4162 | 14.1 |
| 24.8 | 3.6 | 29582 | 100.0 |
| 26.3 | 3.4 | 1835 | 6.2 |
| 27.2 | 3.3 | 4878 | 16.5 |
| 28.3 | 3.2 | 1471 | 5.0 |
| 28.8 | 3.1 | 2944 | 10.0 |
| 29.4 | 3.0 | 1312 | 4.4 |
| 30.1 | 3.0 | 3110 | 10.5 |
| 31.2 | 2.9 | 1360 | 4.6 |
| 33.8 | 2.7 | 1564 | 5.3 |

The XRPD profile presented in FIG. 19 indicated the absence of amorphous material in the Varoglutamstat Hydrochloride obtained in Example 4.3.

Example 5.4 Polymorphism Screen

The polymorphism screening was performed using the Varoglutamstat Hydrochloride produced according to example 4.1 and three different types of experiments: Cooling/Precipitation and evaporation crystallization was carried out to screen for kinetically preferred forms, slurry type experiments were performed to identify the preferred thermodynamically stable form.

Cooling and Precipitation Experiments

The starting material was suspended in the solvents indicated below and heated to maximum 65° C. to get dissolved completely. As the general solubility was low in most of the solvents utilized here and temperature-dependent differences in solubility were often low, several precipitation attempts were performed by anti-solvent addition as well. All samples were shock cooled in an ice/sodium chloride bath.

TABLE 7

Cooling and precipitation experiments.

| Exp. | Solvent | Optical impression | Comment | Form | LIMS-Task-ID |
|---|---|---|---|---|---|
| C1_1 | MeOH | paste | | A/amorphous | 303171463 |
| C1_2 | EtOH | paste | | A/amorphous | 303171465 |
| C1_3 | THF/water 10/1 | no solid | | — | — |
| C1_4 | water | thin | not filterable | — | — |
| C1_5 | acetone/MeOH 7/1 | thin | hardly filterable | — | 303171467 |
| C1_6 | ACN/water 7/1 | solution | +TBME > resin | — | — |
| C1_7 | MeOH on TBME | paste | slow filtration | A/amorphous | 303171469 |
| C1_8 | DMSO on EtOAc | paste | slow filtration | A/amorphous | 303171471 |
| C1_9 | Water on acetone | solution | | — | — |
| C1_10 | HOAc on acetone | solution | | — | — |
| C2_1 | DMSO on IProAc | sticky | | A/amorphous | 303171473 |
| C2_2 | DMSO on acetone | suspension | after 2 days | A/amorphous | 303171475 |

Evaluation of the Results of Cooling and Precipitation Experiments

Figure 25:
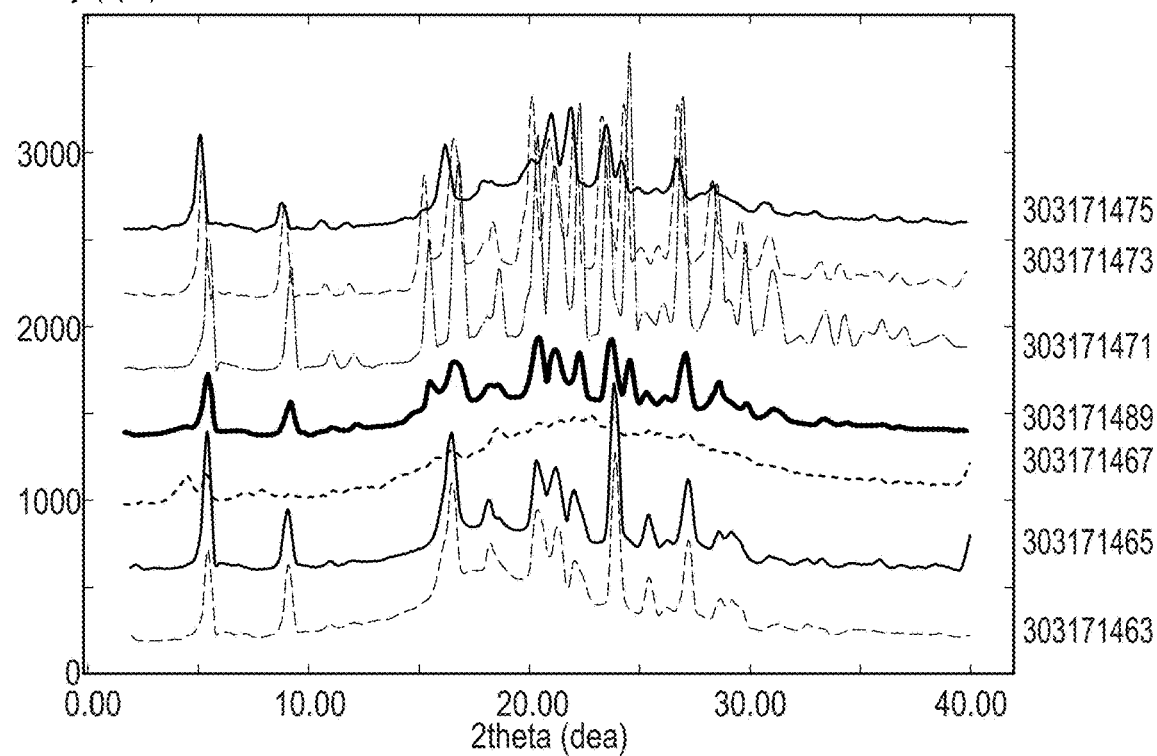
FIG. 25: XRPD taken from cooling and precipitation experiments (numbers correspond to the LIMS-Task ID in Table 9).

Most of the crystallization attempts did not result in emphasized solid formation or did not even crystallize. Resulting suspensions, if present, all were very pasty and could not be transferred onto the filter. In some cases, the suspensions were impossible to be filtered as the crystals were to fine and rushed through the filter material. The six samples which delivered a sufficient amount of solid for XRPD showed only bad crystallinity (see Table 7). The polymorphs found were found to be of the identical form "A" (See FIG. 25 and Table 6).

Evaporation Experiments

Starting material was suspended in the solvents given in Table 8 below and heated to max. 30° C. All experiments had to be filtered as no complete dissolution occurred.

The solutions were slowly concentrated next by slowly evaporating the solvent at Room Temp. at 900-950 mbar under nitrogen atmosphere.

Evaluation of the Results of the Evaporation Experiments

Figure 26:
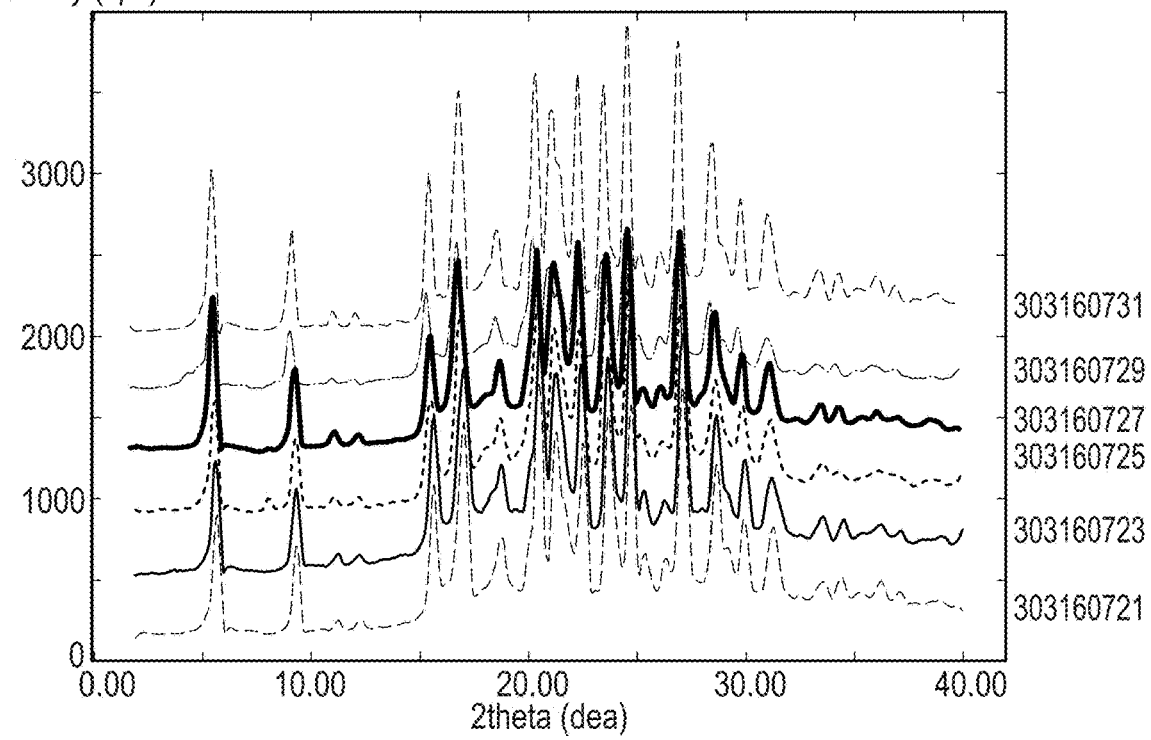
FIG. 26: XRPD taken from evaporation experiments (numbers correspond to the LIMS-Task ID in Table 10).
Figure 27:
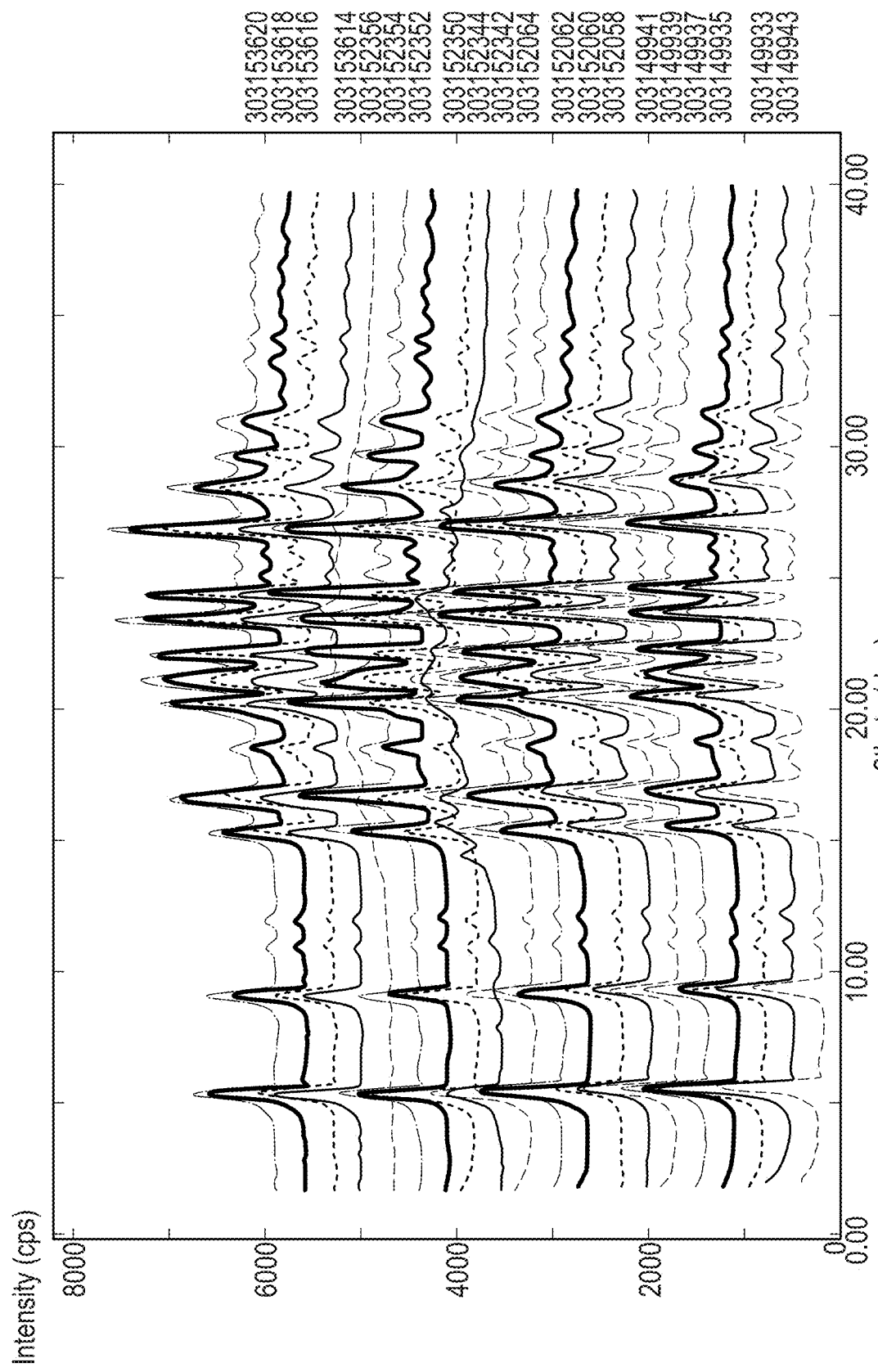
FIG. 27: XRPD taken from slurry experiments (numbers correspond to the LIMS-Task ID in Table 11).

Only six experiments delivered sufficient material for XRPD examination, as can be seen from Table 8. The six isolated white crust samples all delivered the same XRPD reflection pattern (see FIG. 26).

TABLE 8

Evaporation experiments

| Exp. | Solvent | Optical Impression | Comment (before evaporation) | Form | LIMS-Task-ID |
|---|---|---|---|---|---|
| B1_1 | water | white crust | filtered | A | 303160721 |
| B1_2 | methanol | white crust | filtered | A | 303160723 |
| B1_3 | trifluorethanol | white crust | filtered | A | 303160725 |
| B1_4 | ethanol | white crust | filtered | A | 303160727 |
| B1_5 | dimethoxyethane | glass | decanted/filtered | too few | — |
| B1_6 | dichloromethane | glass | decanted/filtered | too few | — |
| B1_7 | acetonitrile | white crust | decanted/filtered | too few | — |
| B1_8 | fluorobenzene | — | decanted/filtered | too few | — |
| B1_9 | methyl formate | — | decanted/filtered | too few | — |
| B1_10 | THF | — | decanted/filtered | too few | — |
| B2_1 | acetic acid | yellowish | filtered | A | 303160729 |
| B2_2 | DCM/MeOH 3/1 | white crust | filtered | A | 303160731 |

Slurry Experiments

For the slurry experiments approximately 100 mg of the starting HCl salt were suspended with as few solvent as necessary to have a well stirrable suspension. The suspensions were stirred for 5 days at r.t. and filtered without washing.

TABLE 9

Slurry experiments *.

| Experiment | Solvent | Optical Impression | Form | LIMS-Task-ID |
|---|---|---|---|---|
| A1_1 | TBME | paste | A | 303149943 |
| A1_2 | acetone | paste | A | 303149933 |
| A1_3 | THF | paste | A | 303149935 |
| A1_4 | Ethyl acetate | paste | A | 303149937 |
| A1_5 | MEK | paste | A | 303149939 |
| A1_6 | ACN | paste | A | 303149941 |
| A1_7 | Isopropylacetate | paste | A | 303152058 |
| A1_8 | n-heptane | paste | A | 303152060 |
| A1_9 | toluene | paste | A | 303152062 |
| A1_10 | MIBK | paste | A | 303152064 |
| A2_1 | 2-Me-THF | paste | A | 303152342 |
| A2_2 | DCM | paste | A + X/amorphous | 303152344 |
| A2_3 | Dioxane | paste | A | 303152350 |
| A2_4 | trifluoroethanol | paste | A | 303152352 |
| A2_5 | EtOAc (wet) | paste | A | 303152354 |
| A2_6 | water | paste | A/amorphous | 303152356 |
| A2_7 | n-propanol | paste | A | 303153614 |
| A2_8 | methanol | paste | A | 303153616 |
| A2_9 | ethanol | paste | A | 303153618 |
| A2_10 | 2-propanol | paste | A | 303153620 |

* Form "X" indicates additional unidentified reflexes in the XRPD pattern.

Evaluation of the Results of the Slurry Experiments

At the beginning of the 5 day stirring period, the suspensions were found to be less pasty but converted quickly into a similarly pasty texture as observed for the above cooling and precipitation experiments (Table 7, Table 8). After filtration the wet cakes were dried gently in vacuum to be able to be applied for XRPD. An overview of the results is given in Table 9. The XRPD measurements resulted in the identification of the polymorph form "A". The sample prepared in water (303152356) still showed an overall amorphous character, whereas the sample taken in DCM (303152344), except being of low crystallinity, revealed additional unidentified reflexes.

Polymorphism Screening Results of the Material Obtained in Examples 3.2, 4.1 and 4.3

The polymorph screening identified only the already known form "A" of the Varoglutamstat HCl salt observed in Example 3.3, 4.2, and 4.3 as it is shown in Example 5.5 below.

Example 5.5: Proof of Polymorph Identity and Crystallinity Comparison

The Varoglutamstat HCl salt crystals obtained in Examples 3.2, 4.2 and 4.3 have XRPD patterns with similar Thêta) (°) peaks. The main difference between the XRPD patterns of the three crystal forms is the relative intensity of the peaks. In order to proof the identity of the polymorph obtained in all examples and to investigate possible reasons for the different Thêta) (°) peak intensities, the crystallinity of the material from Examples 4.2 and 4.3 was analyzed and compared under identical conditions for the following parameters:
XRPD analysis,
DSC analysis, and
optical microscopy.

Results of XRPD Analysis

Figure 28:
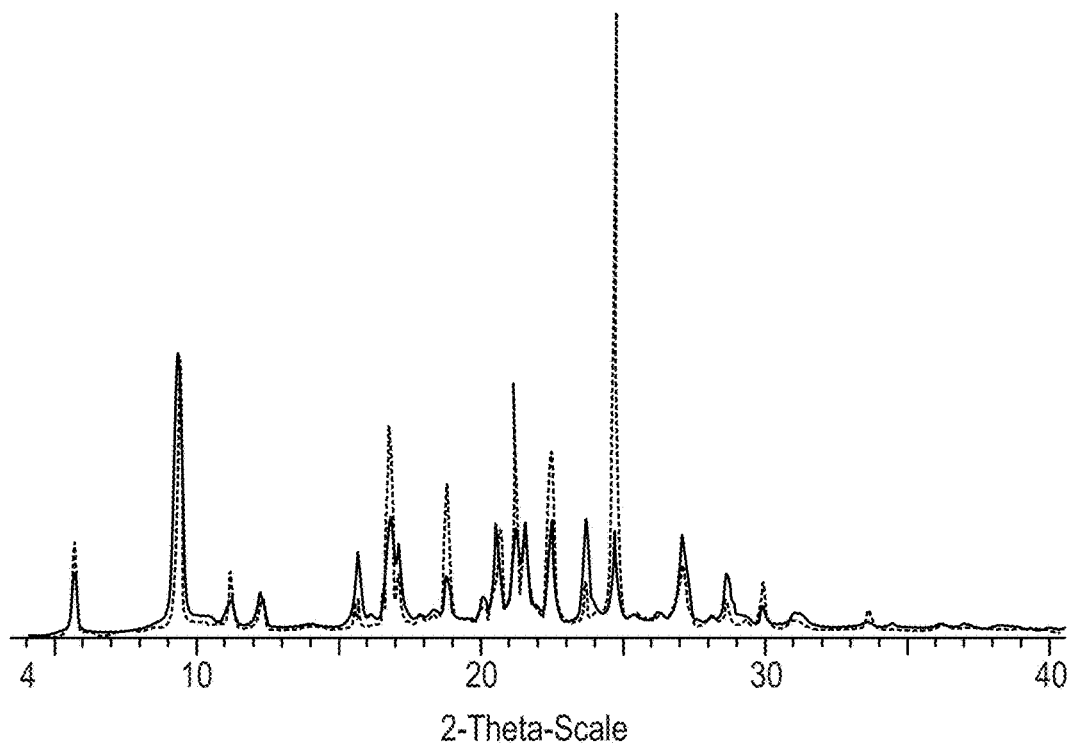
FIG. 28: Overlay, without ordinate offset, of X-ray diffraction profiles of Varoglutamstat HCl obtained in example 4.2 (solid trace) and example 4.3 (dashed trace)—With ordinate scale normalized by mass assay.
Figure 29:
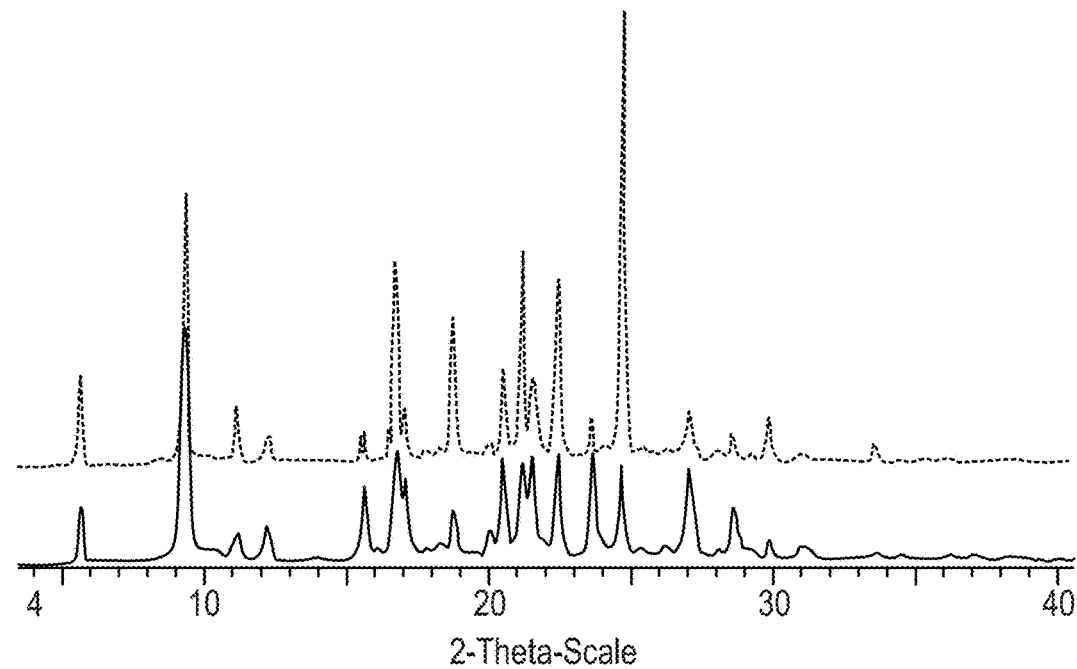
FIG. 29: Overlay, with ordinate offset, of X-ray diffraction profiles of Varoglutamstat HCl obtained in example 4.2 (dashed trace) and example 4.3 (dashed trace)—With ordinate scale normalized by mass assay.

The overlaid X-ray powder diffraction profile of Varoglutamstat HCl from examples 4.2 and 4.3 are presented in FIGS. 28 and 29, respectively.

The XRPD profiles obtained in examples 4.2 and 4.3 exhibit several sharp and intense diffraction peaks and no significant diffusion background. This kind of profile is characteristic of an organic material comprising a crystallized phase with no significant amorphous phase detected in the used operating conditions.

Other observations resulting from these Varoglutamstat HCl diffraction data are:
The relative intensity profiles are different in these two batches (see FIG. 28);
Both batches evidence the same diffraction peak positions (see FIG. 29 and Tables 10 and 11);
Varoglutamstat HCl from example 4.3 exhibits better-resolved X-ray diffraction peaks, which is the consequence of a lower full width at half maximum (see Table 10);
Varoglutamstat HCl from example 4.3 exhibits an average X-ray diffraction peak area higher than that of Varoglutamstat HCl from example 4.2 for a similar tested sample mass (see Table 11), on average 1.5 times higher for Varoglutamstat HCl from example 4.3 (see table 12).

Table 12.1 contains the all peak positions of the complete XRPD patterns of Varoglutamstat HCl from examples 4.2 and 4.3.

TABLE 10

Full width at half maximum (FWHM) of main well-resolved X-ray diffraction-peaks of Varoglutamstat HCl from example 4.2 and example 4.3 (from the XRPD profiles normalized by mass assay).

| Ex. 4.2 | | | Ex. 4.3 |
|---|---|---|---|
| Angle 2-theta (°) | FHWM (2-Theta °) | | Angle 2-theta (°) |
| 5.7 | 0.196 | 0.161 | 5.7 |
| 9.3 | 0.244 | 0.193 | 9.3 |
| 11.2 | 0.202 | 0.161 | 11.2 |
| 12.2 | 0.257 | 0.218 | 12.3 |
| 15.7 | 0.224 | 0.160 | 15.6 |
| 18.8 | 0.205 | 0.172 | 18.8 |
| 20.2 | 0.160 | 0.173 | 20.1 |
| 20.6 | 0.180 | 0.153 | 20.6 |
| 22.5 | 0.221 | 0.195 | 22.5 |
| 23.7 | 0.204 | 0.137 | 23.7 |
| 24.8 | 0.201 | 0.148 | 24.7 |
| 27.2 | 0.274 | 0.265 | 27.1 |
| 28.7 | 0.276 | 0.227 | 28.7 |
| 30.0 | 0.197 | 0.164 | 30.0 |
| Mean | 6.387 | 8.068 | Mean |

TABLE 11

X-ray diffraction main well-resolved peak areas of Varoglutamstat HCl from example 4.2 and example 4.3 (from the XRPD profiles normalized by mass assay).

| Ex. 4.2 | | | Ex. 4.3 |
|---|---|---|---|
| Angle 2-theta (°) | Net Area (Cps × 2-Theta | | Angle 2-theta (°) |
| 5.7 | 4.936 | 5.923 | 5.7 |
| 9.3 | 26.490 | 21.710 | 9.3 |
| 11.2 | 1.990 | 3.257 | 11.2 |
| 12.2 | 3.168 | 2.337 | 12.3 |

TABLE 11-continued

X-ray diffraction main well-resolved peak areas of Varoglutamstat HCl from example 4.2 and example 4.3 (from the XRPD profiles normalized by mass assay).

| Ex. 4.2 | | Ex. 4.3 | |
|---|---|---|---|
| Angle 2-theta (°) | Net Area (Cps × 2-Theta) | | Angle 2-theta (°) |
| 15.7 | 5.842 | 1.755 | 15.6 |
| 18.8 | 2.748 | 9.632 | 18.8 |
| 20.2 | 0.830 | 0.887 | 20.1 |
| 20.6 | 5.278 | 5.224 | 20.6 |
| 22.5 | 8.012 | 15.410 | 22.5 |
| 23.7 | 8.865 | 2.364 | 23.7 |
| 24.8 | 6.830 | 34.190 | 24.7 |
| 27.2 | 9.051 | 5.824 | 27.1 |
| 28.7 | 3.938 | 1.733 | 28.7 |
| 30.0 | 1.433 | 2.710 | 30.0 |
| Mean | 6.387 | 8.068 | Mean |

TABLE 12

X-ray diffraction peak area ratio Varoglutamstat HCl: example 4.3 and example 4.2. Peak area ratio Ex. 4.3/Ex. 4.2

| Angle 2-theta (°) | Ratio |
|---|---|
| 5.7 | 1.200 |
| 9.3 | 0.820 |
| 11.2 | 1.637 |
| 12.3 | 0.738 |
| 15.6 | 0.300 |
| 18.8 | 3.505 |
| 20.1 | 1.069 |
| 20.6 | 0.990 |
| 22.5 | 1.923 |
| 23.7 | 0.267 |
| 24.7 | 5.006 |
| 27.1 | 0.643 |
| 28.7 | 0.440 |
| 30.0 | 1.891 |
| Mean | 1.46 |

TABLE 12.1

XRPD peak positions. complete list. The position of the Theta (°) peaks in the table above my vary by ±0.2°.

| Ex. 4.2 | | | | Ex. 4.3 | | | |
|---|---|---|---|---|---|---|---|
| Angle 2-Theta (°) | Inter-reticular distance (Å) | Intensity counts | % | Angle 2-Theta (°) | Inter-reticular distance (Å) | Intensity counts | % |
| 5.7 | 15.55 | 3197 | 23.8 | 5.7 | 15.41 | 6229 | 14.8 |
| 9.3 | 9.47 | 13407 | 100.0 | 9.3 | 9.48 | 18794 | 44.7 |
| 12.2 | 7.91 | 1780 | 13.3 | 11.2 | 7.88 | 4175 | 9.9 |
| 12.2 | 7.23 | 2024 | 15.1 | 12.3 | 7.19 | 2496 | 5.9 |
| 15.7 | 5.65 | 4029 | 30.1 | 15.6 | 5.68 | 2506 | 6.0 |
| 16.8 | 5.27 | 5750 | 42.9 | 16.8 | 5.27 | 14126 | 33.6 |
| 17.2 | 5.16 | 4262 | 31.8 | 17.2 | 5.15 | 4083 | 9.7 |
| 17.9 | 4.95 | 1034 | 7.7 | 17.9 | 4.96 | 1325 | 3.1 |
| 18.4 | 4.82 | 1261 | 9.4 | 18.4 | 4.83 | 1579 | 3.8 |
| 18.8 | 4.71 | 2882 | 21.5 | 18.8 | 4.72 | 11697 | 27.8 |
| 20.1 | 4.41 | 1849 | 13.8 | 20.2 | 4.40 | 1816 | 4.3 |
| 20.6 | 4.32 | 5287 | 38.4 | 20.6 | 4.31 | 7355 | 17.5 |
| 21.2 | 4.18 | 4953 | 36.9 | 21.2 | 4.18 | 17151 | 40.8 |
| 21.5 | 4.12 | 5337 | 39.8 | 21.6 | 4.11 | 6797 | 16.2 |
| 22.0 | 4.04 | 1536 | 11.5 | 22.0 | 4.04 | 1633 | 3.9 |
| 22.5 | 3.96 | 5531 | 41.3 | 22.5 | 3.95 | 15017 | 35.7 |
| 23.7 | 3.75 | 5511 | 41.1 | 23.7 | 3.75 | 3814 | 9.1 |
| 24.1 | 3.70 | 1487 | 11.1 | 24.1 | 3.70 | 1790 | 4.3 |
| 24.8 | 3.59 | 4931 | 36.8 | 24.7 | 3.60 | 42081 | 100.0 |
| 25.4 | 3.50 | 1036 | 7.7 | 25.4 | 3.50 | 1622 | 3.9 |
| 26.3 | 3.39 | 1211 | 9.0 | 26.2 | 3.39 | 1439 | 3.4 |
| 27.2 | 3.28 | 4679 | 34.9 | 27.1 | 3.29 | 4329 | 10.3 |
| 28.2 | 3.16 | 993 | 7.4 | 28.2 | 3.16 | 1414 | 3.4 |
| 28.7 | 3.11 | 2823 | 21.1 | 28.7 | 3.11 | 2410 | 5.7 |
| 29.3 | 3.04 | 992 | 7.4 | 29.3 | 3.05 | 1273 | 3.0 |
| 30.0 | 2.98 | 1482 | 11.1 | 30.0 | 2.98 | 3726 | 8.9 |
| 31.1 | 2.87 | 1142 | 8.5 | 31.1 | 2.88 | 1150 | 2.7 |
| 31.3 | 2.85 | 1162 | 8.7 | 31.3 | 2.86 | 954 | 2.3 |
| 33.6 | 2.66 | 685 | 5.1 | 33.6 | 2.66 | 1699 | 4.0 |
| 34.5 | 2.60 | 604 | 4.5 | 34.6 | 2.59 | 514 | 1.2 |
| 35.4 | 2.54 | 518 | 3.9 | 35.4 | 2.54 | 692 | 1.6 |
| 36.3 | 2.47 | 576 | 4.3 | 36.2 | 2.48 | 803 | 1.9 |
| 37.1 | 2.42 | 560 | 4.2 | 37.0 | 2.43 | 508 | 1.2 |
| 38.5 | 2.33 | 437 | 3.3 | 38.6 | 2.33 | 558 | 1.3 |
| 38.3 | 2.29 | 424 | 3.2 | 39.3 | 2.29 | 454 | 2.1 |

An alternative approach for crystallinity characterization is based on an USP harmonized method ((941) Characterization of crystalline and partially crystalline solids by X-ray powder diffraction (XRPD), Stage 4 Harmonization, May 2022).

When the bulk API consists in one amorphous fraction mixed with one crystalline fraction, the relative degree of crystallinity can be comparatively estimated between two batches by comparing the following "crystallinity factor":

10% Crystallinity=100×A/(A+B−C)

wherein:
A is the sum of the net areas of all the peaks arising from the diffraction of the crystalline fraction of the sample;
B is the area under the diffractogram generated by the sample itself (excluding area A); and
C is the area of the background noise (due to air scattering, fluorescence, equipment, etc.) which is measured by recording the diffractograms of the (empty) sample holder that was used for recording the diffractograms of the tested samples.

For Varoglutamstat HCl from examples 4.2 and 4.3, the calculations give the following results (Table 13):

TABLE 13

Comparative crystallinity characterization of Varoglutamstat HCl from examples 4.2 and 4.3 according to USP method

|   | Ex. 4.2 | Ex. 4.3 |
|---|---|---|
| A | 124 | 188 |
| B | 115 | 132 |
| C | 45 | 45 |
| Degree of crystallinity | 64% | 68% |

This calculation evidences a slightly higher degree of crystallinity for Varoglutamstat HCl from example 4.3.

In conclusion, the X-ray powder diffraction analysis shows that both samples comprise the same crystalline phase (the same diffraction peak positions are detected) and no significant amorphous phase (no significant scattering background is observed) under the used operating conditions.

However, there are some differences such as:
Different relative intensity profiles, probably resulting from different crystal morphologies (see optical microscopy observations described below);
Better-resolved diffraction peaks for Varoglutamstat HCl from example 4.3 with a narrower average peak width at half maximum, thus meaning less disorder in the crystal lattice and so a better crystallinity;
A larger average peak area for Varoglutamstat HCl from example 4.3, therefore, also meaning a better crystallinity,
And finally, a slightly higher degree of crystallinity for Varoglutamstat HCl from example 4.3, as estimated, based on a USP method.

The comparative analysis of XRPD data of Varoglutamstat HCl from examples 4.2 and 4.3 suggests that the crystallinity of Varoglutamstat HCl from example 4.3 is higher than the one from example 4.2.

Results of DSC Analysis

Figure 30:
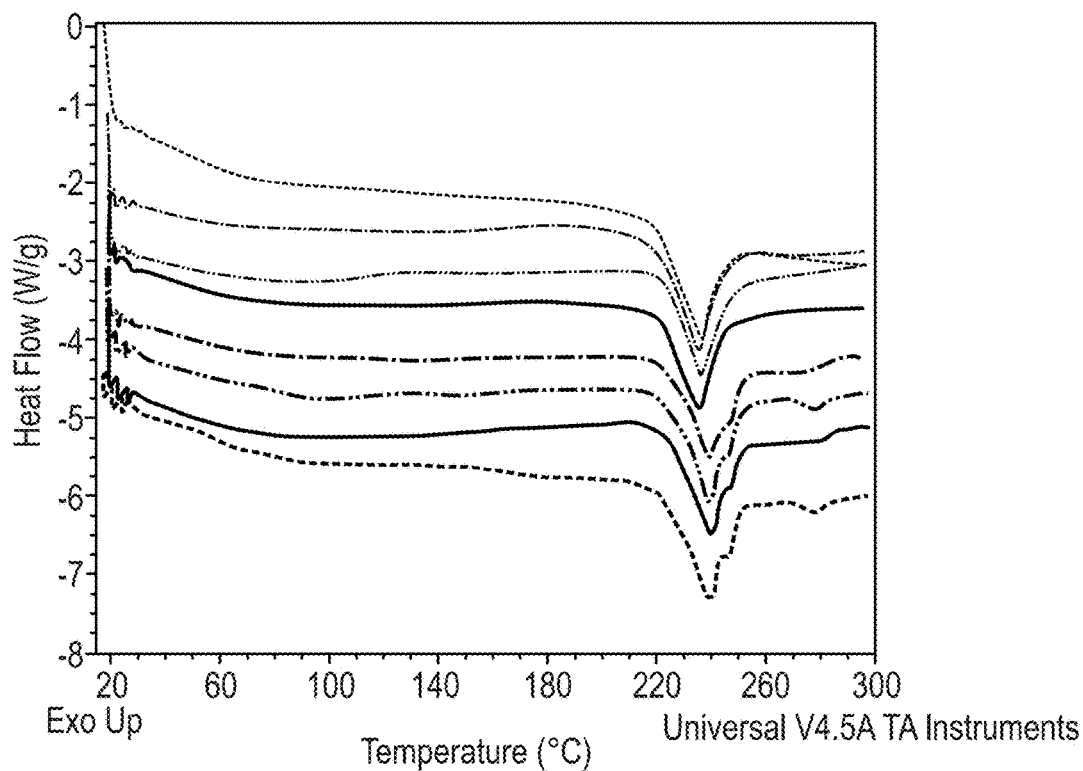
FIG. 30: Overlay of DSC profiles of Varoglutamstat HCl obtained in example 4.2 (upper four traces) and example 4.3 (lower four traces).

An overlay of the DSC thermograms of Varoglutamstat HCl from examples 4.2 and 4.3 is presented in FIG. 30. The quantitative DSC integration results are shown in Table 14 and Table 15.

For each studied batch, four runs were performed with a tested sample mass of the same order of magnitude. For the fourth run, the material was gently ground before the weighing; it can thus be observed whether or not the texture of the native material has an impact on the DSC profile.

The DSC profiles of Varoglutamstat HCl from examples 4.2 and 4.3 evidence one single endothermic transition, which corresponds to the melting of the crystalline phase evidenced by XRPD and detected with an onset melting point of 222 and 224° C. for the material from example 4.2 and from example 4.3 respectively.

TABLE 14

Quantitative DSC results of Varoglutamstat HCl from example 4.2

| Sample | Preparation | Mass assay (mg) | Temperature (° C.) | | | | | Enthalpy (J/g) |
|---|---|---|---|---|---|---|---|---|
| | | | Start | Onset | Maximum | Width | Stop | |
| Ex. 4.2 | none | 1.031 | 204 | 221 | 235 | 13 | 255 | 116 |
| | | 1.130 | 204 | 221 | 235 | 13 | 255 | 120 |
| | | 1.072 | 204 | 224 | 237 | 12 | 255 | 102 |
| | gently ground | 1.015 | 204 | 221 | 235 | 13 | 255 | 117 |

TABLE 15

Quantitative DSC results of Varoglutamstat HCl from example 4.3

| Sample | Preparation | Mass assay (mg) | Temperature (° C.) | | | | | Enthalpy (J/g) |
|---|---|---|---|---|---|---|---|---|
| | | | Start | Onset | Maximum | Width | Stop | |
| Ex. 4.3 | none | 1.352 | 204 | 226 | 240 | 16 | 255 | 115 |
| | | 1.066 | 204 | 223 | 239 | 16 | 255 | 129 |
| | | 1.035 | 204 | 224 | 239 | 15 | 255 | 121 |
| | gently ground | 1.014 | 204 | 224 | 239 | 15 | 255 | 118 |

Other observations resulting from these DSC data of Varoglutamstat HCl are:
- There is no impact of the material texture as the same profile is observed for both native and gently ground samples;
- Both the onset melting temperatures and the melting enthalpies can be considered as statistically identical as their respective confidence intervals overlap (see Table 16 and Table 17).

TABLE 16

Comparison of onset melting temperatures of
Varoglutamstat HCl from examples 4.2 and 4.3.
Onset melting temperature (° C.)

|  | Ex. 4.2 | Ex. 4.3 |
| --- | --- | --- |
|  | 221 | 226 |
|  | 221 | 223 |
|  | 224 | 224 |
|  | 221 | 224 |
| Mean | 222 | 224 |
| Standard deviation | 1.5 | 1.3 |
| Confidence Interval (p = 0.95) | [220; 224] | [222; 226] |

TABLE 17

Comparison of melting enthalpies of
Varoglutamstat HCl from examples 4.2 and 4.3.
Melting enthalpy (J/g)

|  | Ex. 4.2 | Ex. 4.3 |
| --- | --- | --- |
|  | 116 | 115 |
|  | 120 | 129 |
|  | 102 | 121 |
|  | 117 | 118 |
| Mean | 114 | 121 |
| Standard deviation | 8.0 | 6.0 |
| Confidence Interval (p = 0.95) | [101; 127] | [111; 131] |

In conclusion, the DSC analysis shows that both samples comprise the same crystalline phase as a same onset melting temperature is detected for Varoglutamstat HCl from examples 4.2 and 4.3.

No significant crystallinity difference between Varoglutamstat HCl from examples 4.2 and 4.3 can be evidenced from the DSC data as both their onset melting temperatures and their melting enthalpies are considered as equal since their respective confidence intervals overlap.

Crystallinity Comparison Attempt by Optical Microscopy Observation

Figure 31:
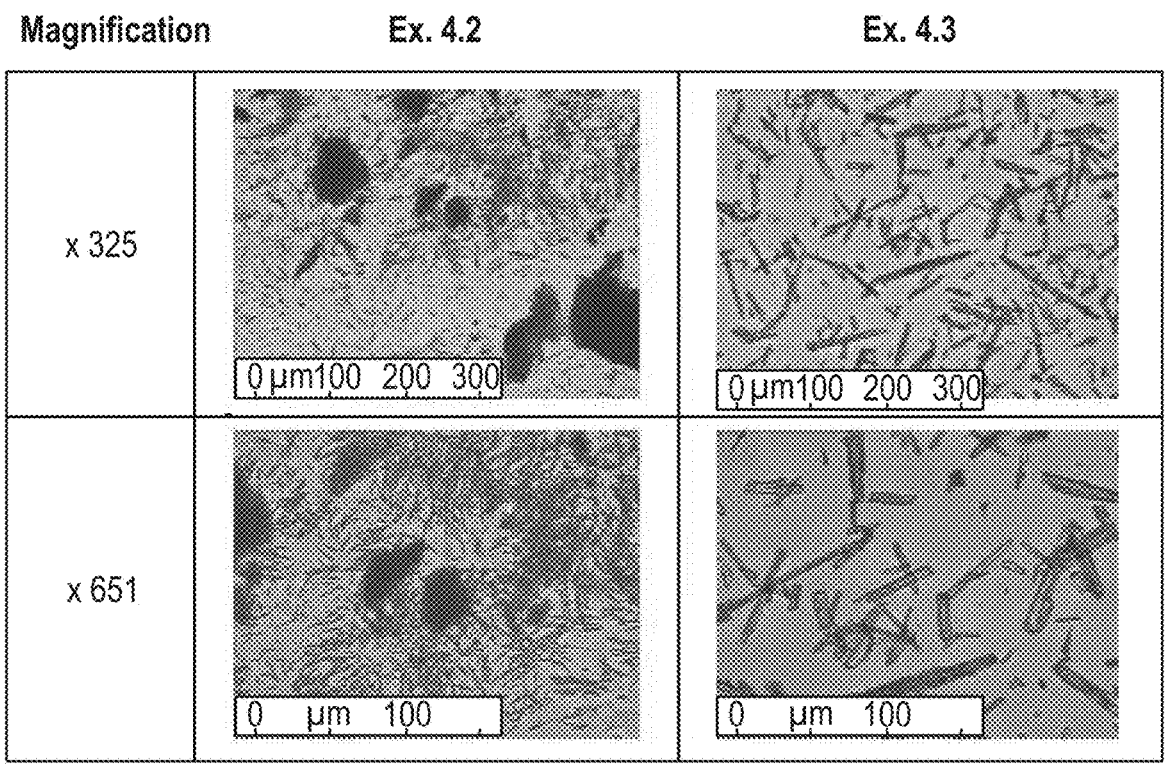
FIG. 31: Comparative optical microscopy observation (with transmitted light) of Varoglutamstat HCl obtained in example 4.2 and example 4.3.

A comparative optical microscopy observation is presented in FIG. 31 and FIG. 32. Two main comments result from these Varoglutamstat HCl optical microscopy data:
- While Varoglutamstat HCl from example 4.2 exhibits a mix of small individualized particles and larger aggregates, Varoglutamstat HCl from example 4.3 exhibits a single particle population made of stick-like or rod-like large well-defined crystals and with no apparent trend towards aggregation.
- For optical microscopy observation with cross-polarized light, it is worth highlighting that for a similar quantity of scattered light by crystals of both batches, the intensity of the incident light beam has to be systematically higher for Varoglutamstat HCl from example 4.2.

In conclusion, these observations retrospectively allow hypothesising that the crystallization process of Varoglutamstat HCl from example 4.2 must have been very sudden and poorly controlled, thus promoting uncontrolled nucleation/precipitation resulting in the presence of small and numerous less perfect crystals and aggregates of those small crystals, whereas the crystallization process of Varoglutamstat HCl from example 4.3 must have been slower and better controlled resulting in less but much larger crystals with a well-defined morphology and a better crystallinity.

Overall Conclusion of Example 5.5

XRPD and DSC profiles evidence that Varoglutamstat HCl from example 4.2 and example 4.3 comprise the same crystallized solidphase with a melting point detected between 222 and 224° C.

The crystallinity comparison performed from XRPD data, and more specifically with the full width at half maximum (FWHM) data and integration area data of the diffraction peaks, resulted in the following comments and conclusions:
- The average FWHM obtained by integrating the main diffraction peaks of Varoglutamstat HCl from example 4.3 is significantly lower than the one obtained from the same main peaks of Varoglutamstat HCl from example 4.2. As lower FWHM is generally indicative of the presence of a more ordered crystal lattice, the crystallinity of Varoglutamstat HCl from example 4.3 could then be considered higher than the one of Varoglutamstat HCl from example 4.2.
- The integration of the diffraction peaks of Varoglutamstat HCl from example 4.2 and 4.3 highlights areas which are on average 1.5 times higher for Varoglutamstat HCl from example 4.3. As the diffraction peak area is proportional to the amount of diffracting crystalline material, the crystallinity of Varoglutamstat HCl from example 4.3 appears to be higher than the one of Varoglutamstat HCl from example 4.2.
- A slightly higher degree of crystallinity for Varoglutamstat HCl from example 4.3, as estimated, based on a USP method.

The crystallinity comparison performed with optical microscopy observation, although rather qualitative, would also conclude in a similar way to XRPD: larger particles, and uniform and well-defined crystal morphology for Varoglutamstat HCl from example 4.3 evidence the presence of a better crystalline material.

On the other hand, the DSC analysis results do not allow a conclusion regarding a difference in crystallinity between Varoglutamstat HCl from example 4.2 and example 4.3: both the onset melting temperatures and the melting enthalpies can be considered as statistically identical as their respective confidence intervals overlap.

Based on the newly recorded XRPD and optical microscopy data of Varoglutamstat HCl from example 4.3, it is possible to conclude that Varoglutamstat HCl from example 4.3 is better crystallized than Varoglutamstat HCl from example 4.2.

Description of analytical procedures used in the Examples of the invention.

TGA Volatile Components

Principle: Thermogravimetry.

Example 3.3

Equipment: TGA 851e apparatus comprising oven, oven temperature sensor and sample temperature sensor/aluminum oxide pan/analytical micro balance.

Procedure: An empty aluminum oxide pan was used to collect the background curve. Afterwards an accurately weighed amount of sample (typically 10 mg) was placed in a clean and dry pan. The measurement was done as described in the analytical instruction of the equipment.

Conditions: starting temperature: 25° C.
heating rate: 5° C./min
final temperature: 300° C.
atmosphere: N2 (flow 50 mL/min)

Example 4.2 and 4.3

Thermogravimetric analysis was performed on a TA Instruments TGA HI-RES 2950 apparatus equipped with an evolved gas analysis furnace. A sample of about 5 to 10 mg was placed in an open aluminum pan and analyzed according to conditions described in Table 18.

TABLE 18

Operating conditions for TGA

| Heater ramp (° C./min) | | 10 |
|---|---|---|
| Final temperature (° C.) | | 500 |
| Carrier gas | nitrogen | Messer, « qualité Azote 5.0 » |
| | flow rate (mL/min) | 95-105 |

Melting Point by DSC
Principle: Differential Scanning Calorimetry with Power Compensation Example 3.3

Equipment: DSC-systems (DSC 822e-Mettler Toledo)/analytical micro balance

Procedure: An accurately weighed amount of sample (typically 1-5 mg) was placed in a clean and dry aluminum crucible and closed with an aluminum cap with a hole. A second one was used as the reference crucible. The measurement was done as described in the analytical instruction of the equipment.

| Conditions: | starting temperature: 20° C. |
|---|---|
| heating rate: | 10° C./min |
| final temperature: | 300° C. |
| atmosphere: | N₂ (flow 20 mL/min) |

Example 4.2 and 4.3

Differential scanning calorimeter (DSC) analysis was performed on a Q1000 TA Instruments analyzer. A sample was weighed in an aluminum capsule, which is then closed, crimped, and put into the calorimeter oven. The instrumental operating conditions for DSC profile acquisition are described in 9.

TABLE 9

Instrument operating conditions for DSC profile acquisition

| Heater ramp (° C./min) | | 10 |
|---|---|---|
| Final temperature (° C.) | | 300 |
| Carrier gas | nitrogen | Messer, « qualité Azote 5.0 » |
| | flow rate (mL/min) | 50 |

Example 5.5

The experimental conditions and the instrumental operating conditions for the DSC profile acquisition in example 5.5 were identical to those described for examples 4.2 and 4.3 and in Table 11 above.

Light Microscopy

Example 3.3

Equipment: OLYMPUS BX41 with ALTRA 20 CMOS-Camera and A-START Analysis Software

Method: Samples were prepared with brushes onto object holders. Observation was done using unpolarised light or polarised light using two polarisation filters at 40, 100, 200 or 400× magnification. Pictures were taken by software and exported as PDF, scale was only approximate and not validated.

Example 4.2 and 4.3

Analysis by optical microscopy was performed on a LEICA DMIRB microscope equipped with a digital camera and a motorized stage. Acquisition of microscopy patterns was performed with an image analysis station. The various images were recorded with normal light and then polarized light (crossed polarizer and analyzer).

Example 5.5

Observation by optical microscopy is performed on a LEICA DMIRB microscope equipped with a digital camera and a motorized stage. Acquisition of microscopy patterns is performed with a Microvision Instruments image analysis station.

The various images are recorded with transmitted light and then with cross-polarized light after the sample is extemporaneously dispersed in a mineral oil.

X-Ray Powder Diffraction

Example 3.3

Equipment:
MINIFLEX by Rigaku Corporation using silicon low background sample holders (diameter 24 mm, pit 0.2 mm).
Tube: Cu, 1=1.54056 Å, 15 kV
Method:
Angle: 2θ=2° to 2θ=40°
Sampling width 0.02 [2θ]
Measurement time: 75 minutes.
Preparation: Samples resulting from experiments were ground with mortar and pestle, which led to more consistent results, less preferred orientation and better handling of material with huge particle size. Solid was positioned on sample holder, prepared with grease and flattened with a disc of glass.

Example 4.2 and 4.3

X-ray powder diffraction (XRPD) analysis was performed on a Bruker-AXS D8 ADVANCE diffractometer, using a copper anti-cathode, a mono-crystalline silicon sample holder and a position sensitive detector. Instrument operating conditions for X-ray pattern acquisition are described in Table 20. The powder sample was dispersed on the silicon sample holder in a way to avoid preferred orientation (not randomly oriented crystals) and to ensure planarity of the specimen surface.

TABLE 20

Instrument operating conditions for X-ray profile acquisition

| Temperature | | | Ambient |
|---|---|---|---|
| Atmosphere | | | Ambient |
| X-rays generator | voltage (kV) | | 40 |
| | intensity (mA) | | 40 |
| X-rays source | target | | Cu |
| | emission radiation | Kλ₁ (nm) | 0.15406 |
| | | Kλ₂ (nm) | 0.15444 |
| | | ratio Kλ₂/Kλ₁ | 0.5 |
| | Kβ filter radiation | | Nickel |
| Slit (mm) | anti-divergence | | 0.6 |
| Goniometer | angular sector analyzed (° for 2θ) | | 4-70 |
| | step size (° for 2θ) | | 0.0714 |
| Rotation speed for sample holder (rpm) | | | 30 |
| Detection | angular opening (°) | | 8 |
| | step time for measuring diffracted intensity (s) | | 6 |

Example 5.5

XRPD analysis is performed on a Bruker-AXS D2 PHASER, using a copper anti-cathode, a mono-crystalline silicon sample holder and a scintillation counter detector. Instrument operating conditions for X-ray profile acquisition are described in Table 21.

Powder samples are loaded onto a flat mono-crystalline silicon sample holder in a way to avoid preferred orientation (not randomly oriented particles) and to ensure planarity of the specimen surface.

TABLE 21

Instrument operating conditions for X-ray profile acquisition

| Temperature | | Ambient |
|---|---|---|
| Atmosphere | | Ambient |
| X-ray generator | voltage (kV) | 30 |
| | intensity (mA) | 10 |
| X-ray source | target | Cu |
| | emission radiation Kα (nm) | 0.154184 |
| | Kβ filter radiation | Nickel |
| Slit | anti-divergence (mm) | 1 |
| | anti-scattering (mm) | 8 |
| | Soller slit (*) | 2.5 |
| Goniometer | angular sector analyzed (° for 2θ) | 4-70 |
| | step size (° for 2θ) | 0.07 |
| Rotation speed for sample holder (rpm) | | 30 |
| Detection | step time for measuring diffracted intensity (s) | 1 |

A person skilled in the art acknowledges that variations of +/−0.2° for single peaks within the pattern of the diffraction peaks determined by such measurements are common.

Dynamic Vapour Sorption

Example 3.3

Equipment:
VTI-SA by TA Instruments with Isotherm Software for data acquisition and handling, glass sample holder and de-ionised water for vapour production.
Drying Method:
Drying Temp: 60° C.
Heating Rate: 5° C./min
Max Drying Time: 60 min
Equil. Crit.: 0.0010 wt % in 2.00 min
Measurement:
Run Temp: 25° C.
Max Equil Time: 180 min
Equil Crit: 0.0010 wt % in 15.00 min
RH Steps: 2,10,20,30,40,50,60,70,80,90,98,90,80,70,60, 50,40,30,20,10,2,20,40
Data Logging Interval: 2.00 min or 0.0100 wt %

Example 4.2 and 4.3

The dynamic vapor sorption (DVS) analysis with water was performed on a DVS-INTRINSIC incubator from SMS Ltd, equipped with DVS-INTRINSIC control software 1.0.

A sample weight of about 10 mg, placed in an aluminum pan holder, was submitted to four full cycle analyses (sorption-desorption-sorption-desorption) in a dm/dt mode according to the conditions described in Table 22. The sample was pre-dried under a stream of dry filtered air until a stable weight was obtained. Next, relative humidity was increased by 5% increments. For each step, the sample mass was allowed to increase until equilibrium is reached (dm/dt criterion), and then a new relative humidity rise occurred. Relative humidity was ramped up to 95%. After equilibration at this point, desorption began in a similar stepwise fashion, with sample weight again allowed to stabilize after each incremental humidity decrease. For each segment of the method described above, the recording of the sample mass allowed describing of the whole vapor water sorption/desorption behavior versus relative humidity.

TABLE 22

Operating conditions for vapor water sorption/desorption analysis

| Temperature | 25° C. |
|---|---|
| Carrier gas and rate | dried and filtered air at 100 ml · min⁻¹ |
| Mode and criterion | dm/dt ≤ 0.002% · min⁻¹ |
| Humidity range | 0 to 95% RH |
| RH step | 5% |
| Minimum step time | 10 minutes |
| Maximum step time | 360 minutes |

HPLC

Example 1

The analytical HPLC-system consisted of a Agilent MSD 1100 utilizing a WATERS SUNFIRE RP 18 (2.5 μm) analytical column (length: 50 mm, diameter: 2.1 mm), and a diode array detector (DAD). The compounds were analyzed using a gradient at a flow rate of 0.6 mL/min; whereby eluent (A) was acetonitrile, eluent (B) was water and eluent (C) 2% formic acid in acetonitrile applying the following gradient:

| Time | Solvent | Solvent | Solvent |
|---|---|---|---|
| 0 | 5 | 90 | 5 |
| 2.5 | 85 | 10 | 5 |
| 4 | 85 | 10 | 5 |
| 4.5 | 5 | 90 | 5 |
| 6 | 5 | 90 | 5 |

The purities of all reported compounds were determined by the percentage of the peak area at 214 nm.

Example 2

Column: PHENOMENEX LUNA C18, 50×4.6 mm, 3 μm,

Mobile phase A: 0.05% TFA in water,
Mobile phase B: 0.05% TFA in acetonitrile.
Gradient: 10% to 90% B in 10 min, 2 min hold, re-equilibrate to initial gradient composition.
Flow: 1.0 mL/min.
Detection: UV at 225 nm.

Example 4.1

Column: ZORBAX BONUS RP 150 mm×4.6 mm; 3.5 um
Eluent A: 0.05% HCOOH in $H_2O$
Eluent B: 0.05% HCOOH in ACN
Flow 1.00 ml/min
Gradient: 2 min 100% Eluent A, linear increase of Eluent B from 2 to 20 min from 0 to 100%
Detection: UV at 225 nm Example 4.2, 4.3

Equipment: AGILENT HP1100 system or equivalent
Chemicals: Water, $H_2O$ (HPLC grade)
  Acetonitrile, ACN (HPLC grade)
  Potassium dihydrogen phosphate, $KH_2PO_4$ (puriss)
  Disodium hydrogen phosphate, $Na_2HPO_4 \times 2H_2O$ (puriss)
Mobile Phase preparation:
Solution A: Phosphate buffer pH-6:287 mg $Na_2HPO_4$ and 1596 mg $KH_2PO_4$ are exactly weighed and dissolved in 1000 ml water.
Sample preparation:
Mixing solvent for $ACN/H_2O$ 1:1, ACN, Mobile Phase A sample:
For sample purity: Prepare the following concentrations: ~0.2 mg/ml, e.g. 20 mg are dissolved in 100 ml
(crude, cryst. and $ACN/H_2O$ (1/1; v/v) chrom. samples)
Standard preparation: 20 mg (accurately weighed on micro-balance) are dissolved in 100 ml $ACN/H_2O$ (1/1; v/v)
Prepare standard in duplicate (for assay determination)
For in-process-control: Prepare solution: e.g., 100 μl in 1 ml $ACN/H_2O$ 1/1; 40 μl in 1 ml $ACN/H_2O$ 1/1 (proposal)
HPLC parameters:
Column: ZORBAX BONUS RP 4.6×150 mm, 3.5 μm, L60
Mobile phase: A: Phosphate buffer pH=6
  B: ACN
Gradient:

| Time [min] | A [%] | B [%] |
|---|---|---|
| 0 | 100 | 0 |
| 2 | 100 | 0 |
| 17.0 | 25 | 75 |
| 20.0 | 25 | 75 |

Equilibration: 5 min
Pump pressure: 86 bar
Flow rate: 1.0 ml/min
Temperature: 25° C.
Detection: 225 nm
  Bandwidth: 8 nm
  Data collection rate: 10 Hz
  Average: on
  Ref Bandwidth: off
  Scans optional: 190-400 nm
  Band width: 2 nm
  Data collection rate: 10 Hz
  Injection volume: 5 μl
  Integration Manual integration
Parameters:
The purities of all reported compounds were determined by the percentage of the peak area at 225 nm.
Proton NMR
Chemical shifts are expressed as parts per million (ppm) downfield from tetramethylsilane. Splitting patterns have been designated as follows: s (singlet), d (doublet), dd (doublet of doublet), t (triplet), m (multiplet) and br (broad signal).

Example 1

The 1H NMR-Spectra (500 MHz) were recorded at a BRUKER AC 500. The solvent was DMSO-D6, unless otherwise specified.

Example 3.2, 4.2, 4.3

Equipment: BRUKER AVANCE 400 MHZ, Solvent: DMSO-D6 Internal Standard: Tetramethylsilane (TMS)
NMR assay (Example 4.3)
Frequency 400.13 MHz; Pulse Program zg30 (BRUKER Library); Solvent DMSO-D6+TMS (0 ppm marker); Number of scans 32
Ca. 25 mg of Varoglutamstat Hydrochloride and ca 10 mg of HQDME were dissolved in ca. 0.7 ml DMSO-D6. (HQDME=hydroquinone dimethyl ether).
Headspace Gas Chromatography (HSGC)

Examples 4.1, 4.2 and 4.3

Equipment: —TRACE-GC 2000-System or equivalent with suitable ECD Detector
  PAL-Sampler with HS Oven and PAL HS Syringe 2.5 ml
  22 ml HS vials with 20 mm magnetic Crimp-Cap with septa Silicone/Alu
Sample preparation:
  Mixing solvent: Place 50 g of molecular sieves type A4 in a glass bottle and fill up with 200 ml MeOH.
  Sample preparation:
Prepare the following concentration: Exactly weigh in 200 mg±10 mg sample into a 22 ml headspace vial, add 4.0 ml dried MeOH, close the vial immediately and shake well. Prepare in duplicate.
GC parameters:

| Column: | Optima 624 25 m × 0.2 mm ID, 1.10 μm film |
|---|---|
| Mobile phase: | $H_2$ @ 2.0 ml constant flow |

| Time [min] | Temp. [° C.] | heating rate [° C./min] |
|---|---|---|
| 0.00 | 35 | 0 |
| 5.00 | 35 | 0 |
| 12.17 | 250 | 30 |
| 15.00 | 250 | 0 |

| Injector temp.: | 230° C. |
|---|---|
| Injector liner: | 5 mm split liner with glass wool |
| Mode: | Flow control |
| Flow: | 2.0 ml/min |
| Split flow: | 40 ml/min (Split 1:20) |
| Injection volume: | 1000 μL |

-continued

| | |
|---|---|
| Detector temp.: | 300° C. (ECD) |
| Detection: | Step: 50 Hz |
| | Average: on |
| HS-Sampler settings | Syringe: 2.5 ml NS |
| | Syringe Temp: 35° C. |
| | Fill speed: 1000 µl/s |
| | Incubat. Time: 2 min |
| | Incubat. Temp: 50° C. |
| | Agi. Speed: 500 rpm |
| | Inject speed: 1 ml/s |
| | Syringe Flush: 4 min |
| Recovery: | IPA-Cl @ 5 ppm: 78% |
| Reproducibility: | IPA-Cl n = 6: 2.7% |
| Linearity (2-20 ppm): | $R^2$: 0.9984 (only linear up to 20 ppm) |
| S/N @ 2 ppm | 15 |

Ion Chromatography

Example 3.2

Pre-Column: DIONEX IONPAC AS11, 50×4.0 mm
Column: DIONEX IONPAC AS11. 250×4.0 mm
  Gradient: 5 to 35 mM NaOH in 17 minutes, 2 min hold at 35 mM NaOH, 5 min 5 mM NaOH re-equilibration
Flow 1.00 [mL/min]
Column Temperature 25.00 [C]
Suppressor Type ASRS 4 mm
Suppressor Current 87 [mA]
Data Collection Rate 5.0 [Hz]
Temperature Compensation 1.7 [%/° C.]
Injection volume 1000 [uL]
Sample Preparation: Sample (5-6 mg) dissolved in 100 ml Aqua purificata+250 µl DMSO and treated in an ultrasonic bath for 10 min.

Carl-Fischer Titration

Coulometric, 3-fold determination, evaporation, oven 140° C.

The invention claimed is:
1. A polymorph of varoglutamstat hydrochloride which is characterized by X-ray powder diffraction peaks (2 [Theta]) selected from one or more of the following: 9.5±0.2°, and 24.8±0.2°.
2. The polymorph of varoglutamstat hydrochloride as claimed in claim 1, which is characterized by X-ray powder diffraction peaks (2 [Theta]) selected from one or more of the following: 9.5±0.2°, 21.3±0.2°, 22.6±0.2°, and 24.8±0.2°.
3. The polymorph of varoglutamstat hydrochloride as claimed in claim 1, which is characterized by X-ray powder diffraction peaks (2 [Theta]) selected from one or more of the following: 5.8±0.2°, 9.5±0.2°, 16.9±0.2°, 17.2±0.2°, 18.9±0.2°, 20.7±0.2°, 21.3±0.2°, 21.7±0.2°, 22.6±0.2°, and 24.8±0.2°.
4. The polymorph of varoglutamstat hydrochloride as claimed in claim 1, which is characterized by X-ray powder diffraction peaks (2 [Theta]) selected from one or more of the following: 5.8±0.2°, 9.5±0.2°, 11.3±0.2°, 12.4±0.2°, 15.8±0.2°, 16.9±0.2°, 17.2±0.2°, 18.9±0.2°, 20.2±0.2°, 20.7±0.2°, 21.3±0.2°, 21.7±0.2°, 22.6±0.2°, 23.8±0.2°, 24.8±0.2°, 26.3±0.2°, 27.2±0.2°, 28.3±0.2°, 28.8±0.2°, 29.4±0.2°, 30.1±0.2°, 31.2±0.2° and 33.8±0.2°.
5. The polymorph of varoglutamstat hydrochloride as claimed in claim 1, characterized by an X-ray diffraction spectrum as shown in FIG. 19.
6. The polymorph of varoglutamstat hydrochloride as claimed in claim 1, characterized by a differential scanning calorimetry (DSC) thermogram as shown in FIG. 20.
7. The polymorph of varoglutamstat hydrochloride claim 1, characterized by an DSC endotherm with an onset temperature of 243° C. and with a peak at 251° C.
8. The polymorph of varoglutamstat hydrochloride claim 1, characterized by a dynamic vapor sorption (DVS) curve as shown in FIG. 22.
9. The polymorph of varoglutamstat hydrochloride claim 1, characterized by a thermogravimetric analysis (TGA) thermogram as shown in FIG. 21.
10. The polymorph of varoglutamstat hydrochloride as claimed in claim 9, characterized by one mass loss of 3.0% with onset/endset temperatures of 190/215° C. before the main thermal decomposition of said varoglutamstat hydrochloride.
11. The polymorph of varoglutamstat hydrochloride as claimed in claim 1, characterized by a 1H-NMR spectrum as shown in FIG. 23.
12. The polymorph of varoglutamstat hydrochloride as claimed in claim 1, wherein said polymorph is substantially free of amorphous material.
13. The polymorph of varoglutamstat hydrochloride as claimed in claim 1, characterized by an achiral purity of >95%, or >96%, or >97%, or >98%, or >99%, or >99.5%, or >99.8%, wherein achiral purity is determined by 1H-NMR analysis.
14. A hydrochloride salt of varoglutamstat ((S)-1-(1H-benzo[d]imidazol-5-yl)-5-(4-propoxyphenyl) imidazolidin-2-one) comprising or consisting of a polymorph as claimed in claim 1.
15. The hydrochloride salt of varoglutamstat as claimed in claim 14, wherein said hydrochloride salt of varoglutamstat is non-hygroscopic.
16. The hydrochloride salt of varoglutamstat as claimed in claim 14, wherein said hydrochloride salt of varoglutamstat shows a water uptake <6.0% at 95% RH.
17. The hydrochloride salt of varoglutamstat as claimed in claim 14, wherein the TGA profile of said hydrochloride salt of varoglutamstat shows a mass loss <9.20% corresponding to <2 water molecules per mol or any other solvate related substance.
18. The hydrochloride salt of varoglutamstat as claimed in claim 14, wherein said hydrochloride salt of varoglutamstat shows a degree of crystallinity of >50%, when calculated with formula I:

$$\% \text{ Crystallinity} = 100 \times A/(A+B-C) \quad \text{(Formula I)}$$

wherein
  A is the sum of the net areas of all the peaks arising from the diffraction of the crystalline fraction of the sample;
  B is the area under the diffractogram generated by the sample itself (excluding area A); and
  C is the area of the background noise (due to air scattering, fluorescence, equipment, etc.) which is measured by recording the diffractograms of the (empty) sample holder that was used for recording the diffractograms of the tested samples.
19. The hydrochloride salt of varoglutamstat as claimed in claim 14, wherein crystals of said hydrochloride salt of varoglutamstat comprise needles as shown in FIG. 18.
20. The hydrochloride salt of varoglutamstat as claimed in claim 14, wherein said hydrochloride salt of varoglutamstat has a solubility in water at 20° C. of ≥0.10 M, or ≥0.11 M, or ≥0.12 M, or ≥0.13 M or ≥0.14 M.
21. The hydrochloride salt of varoglutamstat as claimed in claim 14, wherein crystals of said hydrochloride salt of varoglutamstat is substantially free of isopropyl chloride.
22. A process for preparing a hydrochloride salt of varoglutamstat, as claimed in claim 14 said process comprising dissolving varoglutamstat free base in a solvent mixture comprising a polar aprotic water-mixable organic solvent and water, adding a solution comprising HCl, and harvesting varoglutamstat hydrochloride crystals.
23. The process as claimed in claim 22, comprising:
  i. Dissolving varoglutamstat free base in a polar aprotic water-mixable organic solvent;
  ii Adding water to the solvent of step i to produce an organic solvent-water mixture;
  iii Adding a solution comprising aqueous HCl to the organic solvent-water mixture of step ii;
  iv. Optionally adding seed crystals to the solution of step iii;
  V. Ripening the resulting mixture of step iii and/or step iv for a time period sufficient to form a ripened mixture of varoglutamstat hydrochloride crystals;
  vi. Adding to the ripened mixture polar aprotic water-mixable organic solvent to obtain a suspension of varoglutamstat hydrochloride crystals;
  vii. Cooling of the suspension obtained in step vi; and
  viii. Harvesting the varoglutamstat hydrochloride crystals.
24. The process as claimed in claim 22, said process comprising the steps of:
  i. Dissolving 1 eq. varoglutamstat free base in 5 vol. acetone and heating resulting solution to 45±5° C.;
  ii. Adding to the resulting solution in step i water in an amount of 221 mg water per mmol free base while maintaining the solution at 45±5° C.;
  iii. Adding a solution comprising 3 vol. acetone and 0.95 eq of aqueous HCl (32-37% w/w) to the solution produced in step ii;
  iv. Adding seed crystals to the solution of step iii;

V. Incubating the resulting suspension of step iii and/or step iv for a time period sufficient to form a suspension of varoglutamstat hydrochloride crystals;

vi. Adding 16 vol. acetone to said suspension while keeping temperature of the suspension at 45±5° C.;

vii. Cooling of the suspension obtained in step vi to 20±5° C.;

viii. Stirring the suspension of step vii;

ix. Harvesting varoglutamstat hydrochloride crystals from the suspension of step vii by filtration;

X. Rinsing harvested varoglutamstat hydrochloride crystals obtained by filtration in step ix with an acetone/water mixture of 48:1.6 v/v to obtain rinsed varoglutamstat hydrochloride crystals;

xi. Rinsing the rinsed crystals obtained in step x twice with pure acetone; and xii. Drying the crystals rinsed twice with pure acetone in step xi.

25. A pharmaceutical composition comprising a therapeutically effective dose of the hydrochloride salt of varoglutamstat as claimed in claim 14, together with a pharmaceutically acceptable carrier, diluent, or excipient therefor.

26. The pharmaceutical composition as claimed in claim 25, additionally comprising at least one compound selected from the group consisting of neuroprotectants, antiparkinsonian drugs, amyloid protein deposition inhibitors, beta amyloid synthesis inhibitors, antidepressants, anxiolytic drugs, antipsychotic drugs, anti-multiple sclerosis drugs and monoclonal antibodies.

27. A method of treating a disease selected from the group consisting of neurodegenerative diseases, inflammatory diseases, infectious diseases, proliferative diseases, tumours, and kidney diseases, said method comprising a step of administering a therapeutically effective amount of the polymorph of varoglutamstat hydrochloride as claimed in claim 1 to a subject in need thereof.

28. The process as claimed in claim 23, wherein said polar aprotic water-mixable organic solvent is acetone.

29. The process as claimed in claim 22 wherein the polar aprotic water-mixable organic solvent is acetone.

30. A pharmaceutical composition comprising a therapeutically effective dose of the polymorph as claimed in claim 1, together with a pharmaceutically acceptable carrier, diluent, or excipient therefor.

* * * * *

```
                        SEQUENCE LISTING

Sequence total quantity: 21
SEQ ID NO: 1            moltype = AA   length = 42
FEATURE                 Location/Qualifiers
source                  1..42
                        mol_type = protein
                        organism = Homo sapiens
SEQUENCE: 1
DAEFRHDSGY EVHHQKLVFF AEDVGSNKGA IIGLMVGGVV IA                        42

SEQ ID NO: 2            moltype = AA   length = 40
FEATURE                 Location/Qualifiers
source                  1..40
                        mol_type = protein
                        organism = Homo sapiens
SEQUENCE: 2
DAEFRHDSGY EVHHQKLVFF AEDVGSNKGA IIGLMVGGVV                           40

SEQ ID NO: 3            moltype = AA   length = 40
FEATURE                 Location/Qualifiers
source                  1..40
                        mol_type = protein
                        organism = Homo sapiens
SEQUENCE: 3
EFRHDSGYEV HHQKLVFFAE DVGSNKGAII GLMVGGVVIA                           40

SEQ ID NO: 4            moltype = AA   length = 38
FEATURE                 Location/Qualifiers
source                  1..38
                        mol_type = protein
                        organism = Homo sapiens
SEQUENCE: 4
EFRHDSGYEV HHQKLVFFAE DVGSNKGAII GLMVGGVV                             38

SEQ ID NO: 5            moltype = AA   length = 17
FEATURE                 Location/Qualifiers
MOD_RES                 17
                        note = AMIDATION
source                  1..17
                        mol_type = protein
                        organism = Homo sapiens
SEQUENCE: 5
QGPWLEEEEE AYGWMDF                                                    17

SEQ ID NO: 6            moltype = AA   length = 13
FEATURE                 Location/Qualifiers
source                  1..13
                        mol_type = protein
                        organism = Homo sapiens
SEQUENCE: 6
QLYENKPRRP YIL                                                        13
```

```
SEQ ID NO: 7              moltype = AA  length = 10
FEATURE                   Location/Qualifiers
MOD_RES                   10
                          note = AMIDATION
source                    1..10
                          mol_type = protein
                          organism = Homo sapiens
SEQUENCE: 7
QHWSYGLRPG                                                           10

SEQ ID NO: 8              moltype = AA  length = 97
FEATURE                   Location/Qualifiers
source                    1..97
                          mol_type = protein
                          organism = Homo sapiens
SEQUENCE: 8
QPKVPEWVNT PSTCCLKYYE KVLPRRLVVG YRKALNCHLP AIIFVTKRNR EVCTNPNDDW    60
VQEYIKDPNL PLLPTRNLST VKIITAKNGQ PQLLNSQ                             97

SEQ ID NO: 9              moltype = AA  length = 76
FEATURE                   Location/Qualifiers
source                    1..76
                          mol_type = protein
                          organism = Homo sapiens
SEQUENCE: 9
QPDSVSIPIT CCFNVINRKI PIQRLESYTR ITNIQCPKEA VIFKTKRGKE VCADPKERWV    60
RDSMKHLDQI FQNLKP                                                    76

SEQ ID NO: 10             moltype = AA  length = 76
FEATURE                   Location/Qualifiers
source                    1..76
                          mol_type = protein
                          organism = Homo sapiens
SEQUENCE: 10
QPDAINAPVT CCYNFTNRKI SVQRLASYRR ITSSKCPKEA VIFKTIVAKE ICADPKQKWV    60
QDSMDHLDKQ TQTPKT                                                    76

SEQ ID NO: 11             moltype = AA  length = 68
FEATURE                   Location/Qualifiers
source                    1..68
                          mol_type = protein
                          organism = Homo sapiens
SEQUENCE: 11
QVGTNKELCC LVYTSWQIPQ KFIVDYSETS PQCPKPGVIL LTKRGRQICA DPNKKWVQKY    60
ISDLKLNA                                                             68

SEQ ID NO: 12             moltype = AA  length = 373
FEATURE                   Location/Qualifiers
source                    1..373
                          mol_type = protein
                          organism = Homo sapiens
SEQUENCE: 12
QHHGVTKCNI TCSKMTSKIP VALLIHYQQN QASCGKRAII LETRQHRLFC ADPKEQWVKD    60
AMQHLDRQAA ALTRNGGTFE KQIGEVKPRT TPAAGGMDES VVLEPEATGE SSSLEPTPSS   120
QEAQRALGTS PELPTGVTGS SGTRLPPTPK AQDGGPVGTE LFRVPPVSTA ATWQSSAPHQ   180
PGPSLWAEAK TSEAPSTQDP STQASTASSP APEENAPSEG QRVWGQGQSP RPENSLEREE   240
MGPVPAHTDA FQDWGPGSMA HVSVVPVSSE GTPSREPVAS GSWTPKAEEP IHATMDPQRL   300
GVLITPVPDA QAATRRQAVG LLAFLGLLFC LGVAMFTYQS LQGCPRKMAG EMAEGLRYIP   360
RSCGSNSYVL VPV                                                     373

SEQ ID NO: 13             moltype = AA  length = 76
FEATURE                   Location/Qualifiers
source                    1..76
                          mol_type = protein
                          organism = Homo sapiens
SEQUENCE: 13
QPVGINTSTT CCYRFINKKI PKQRLESYRR TTSSHCPREA VIFKTKLDKE ICADPTQKWV    60
QDFMKHLDKK TQTPKL                                                    76

SEQ ID NO: 14             moltype = AA  length = 33
FEATURE                   Location/Qualifiers
source                    1..33
                          mol_type = protein
                          organism = Homo sapiens
SEQUENCE: 14
QPLPDCCRQK TCSCRLYELL HGAGNHAAGI LTL                                 33

SEQ ID NO: 15             moltype = AA  length = 11
FEATURE                   Location/Qualifiers
```

```
source                    1..11
                          mol_type = protein
                          organism = Homo sapiens
SEQUENCE: 15
RPKPQQFFGL M                                                              11

SEQ ID NO: 16             moltype = AA  length = 32
FEATURE                   Location/Qualifiers
REGION                    1..32
                          note = Synthetic peptide
source                    1..32
                          mol_type = protein
                          organism = synthetic construct
SEQUENCE: 16
EVHHQKLVFF AEDVGSNKGA IIGLMVGGVV IA                                       32

SEQ ID NO: 17             moltype = AA  length = 30
FEATURE                   Location/Qualifiers
REGION                    1..30
                          note = Synthetic peptide
source                    1..30
                          mol_type = protein
                          organism = synthetic construct
SEQUENCE: 17
EVHHQKLVFF AEDVGSNKGA IIGLMVGGVV                                          30

SEQ ID NO: 18             moltype = AA  length = 34
FEATURE                   Location/Qualifiers
REGION                    1..34
                          note = Synthetic peptide
source                    1..34
                          mol_type = protein
                          organism = synthetic construct
SEQUENCE: 18
EASNCFAIRH FENKFAVETL ICSRTVKKNI IEEN                                     34

SEQ ID NO: 19             moltype = AA  length = 34
FEATURE                   Location/Qualifiers
REGION                    1..34
                          note = Synthetic peptide
source                    1..34
                          mol_type = protein
                          organism = synthetic construct
SEQUENCE: 19
EASNCFAIRH FENKFAVETL ICFNLFLNSQ EKHY                                     34

SEQ ID NO: 20             moltype = AA  length = 5
FEATURE                   Location/Qualifiers
REGION                    1..5
                          note = Synthetic peptide
source                    1..5
                          mol_type = protein
                          organism = synthetic construct
SEQUENCE: 20
QYNAD                                                                      5

SEQ ID NO: 21             moltype = AA  length = 323
FEATURE                   Location/Qualifiers
source                    1..323
                          mol_type = protein
                          organism = Homo sapiens
SEQUENCE: 21
MWPLVAALLL GSACCGSAQL LFNKTKSVEF TFCNDTVVIP CFVTNMEAQN TTEVYVKWKF          60
KGRDIYTFDG ALNKSTVPTD FSSAKIEVSQ LLKGDASLKM DKSDAVSHTG NYTCEVTELT         120
REGETIIELK YRVVSWFSPN ENILIVIFPI FAILLFWGQF GIKTLKYRSG GMDEKTIALL         180
VAGLVITVIV IVGAILFVPG EYSLKNATGL GLIVTSTGIL ILLHYYVFST AIGLTSFVIA         240
ILVIQVIAYI LAVVGLSLCI AACIPMHGPL LISGLSILAL AQLLGLVYMK FVASNQKTIQ         300
PPRKAVEEPL NAFKESKGMM NDE                                                323
```